US006602914B2

(12) United States Patent
Meng

(10) Patent No.: US 6,602,914 B2
(45) Date of Patent: Aug. 5, 2003

(54) COMPOUNDS AND METHODS FOR THE INHIBITION OF THE EXPRESSION OF VCAM-1

(75) Inventor: Charles Q. Meng, Alpharetta, GA (US)

(73) Assignee: AtheroGenics, Inc., Alpharetta, GA (US)

(*) Notice: Subject to any disclaimer, the term of this patent is extended or adjusted under 35 U.S.C. 154(b) by 185 days.

(21) Appl. No.: 10/114,346

(22) Filed: Apr. 2, 2002

(65) Prior Publication Data
US 2002/0169215 A1 Nov. 14, 2002

Related U.S. Application Data

(63) Continuation of application No. 09/370,046, filed on Aug. 6, 1999, which is a continuation of application No. 09/079,213, filed on May 14, 1998, now Pat. No. 6,147,250.
(60) Provisional application No. 60/047,020, filed on May 14, 1997.

(51) Int. Cl.$^7$ .......................... A01N 31/00; A61K 31/10
(52) U.S. Cl. .......................................... 514/712; 568/50
(58) Field of Search .............................. 568/50; 514/712

(56) References Cited

U.S. PATENT DOCUMENTS

| 3,179,701 | A | 4/1965 | Rocklin |
| 4,029,812 | A | 6/1977 | Wagner et al. |
| 4,076,841 | A | 2/1978 | Wagner et al. |
| 4,078,084 | A | 3/1978 | Wagner et al. |
| 4,115,590 | A | 9/1978 | Lerner |
| 4,752,616 | A | 6/1988 | Hall et al. |
| 4,755,524 | A | 7/1988 | Mueller et al. |
| 4,954,514 | A | 9/1990 | Kita et al. |
| 4,968,710 | A | 11/1990 | Rustad |
| 4,975,467 | A | 12/1990 | Ku et al. |
| 5,043,330 | A | 8/1991 | Nguyen et al. |
| 5,061,734 | A | 10/1991 | Mao et al. |
| 5,066,822 | A | 11/1991 | Rustad |
| 5,084,214 | A | 1/1992 | Kita et al. |
| 5,112,870 | A | 5/1992 | Mao et al. |
| 5,206,247 | A | 4/1993 | Regnier et al. |
| 5,262,439 | A | 11/1993 | Parthasarathy |
| 5,294,724 | A | 3/1994 | Jendralla et al. |
| 5,310,949 | A | 5/1994 | Dufresne et al. |
| 5,411,741 | A | 5/1995 | Zaias |
| 5,426,196 | A | 6/1995 | Fang |
| 5,608,095 | A | 3/1997 | Parker et al. |
| 5,627,205 | A | 5/1997 | Regnier et al. |
| 5,693,337 | A | 12/1997 | Suzuki et al. |
| 5,739,374 | A | 4/1998 | Janssen et al. |
| 5,770,355 | A | 6/1998 | Brocia |
| 6,037,377 | A | 3/2000 | Anderskewitz et al. |
| 6,121,319 | A | 9/2000 | Somers |

FOREIGN PATENT DOCUMENTS

| DE | 27 16 125 A1 | 10/1977 |
| EP | 0 190 682 A2 | 8/1986 |
| EP | 0 212 310 A2 | 3/1987 |
| EP | 0 254 272 A2 | 1/1988 |
| EP | 0 290 660 A2 | 11/1988 |
| EP | 0 317 165 A1 | 5/1989 |
| EP | 0 348 203 A1 | 12/1989 |
| EP | 0 405 788 A2 | 1/1991 |
| EP | 0 621 255 A1 | 10/1994 |
| EP | 0 763 527 A1 | 3/1997 |
| EP | 0 866 049 A2 | 9/1998 |
| FR | 2.130.875 | 11/1972 |
| FR | 2.133.024 | 11/1972 |
| FR | 2.134.810 | 12/1972 |
| FR | 2.140.769 | 1/1973 |
| FR | 2.168.137 | 8/1973 |
| GB | 1136539 | 12/1968 |
| GB | 1148550 | 4/1969 |
| GB | 1199871 | 7/1970 |
| JP | 73-28425 | 12/1995 |
| WO | 93/02051 | 2/1993 |
| WO | 94/07869 | 4/1994 |
| WO | 95/09158 | 4/1995 |
| WO | 95/15760 | 6/1995 |
| WO | 95/17408 | 6/1995 |
| WO | 95/30415 | 11/1995 |
| WO | 96/12703 | 5/1996 |
| WO | 97/15546 | 5/1997 |
| WO | 97/26258 | 7/1997 |
| WO | 97/48694 | 12/1997 |
| WO | 98/22418 | 5/1998 |
| WO | 98/30255 | 7/1998 |
| WO | 98/42327 | 10/1998 |
| WO | 99/15159 | 4/1999 |
| WO | 99/24400 | 5/1999 |
| WO | 00/26167 | 5/2000 |
| WO | 00/26184 | 5/2000 |
| WO | 00/31053 | 6/2000 |
| WO | 00/53795 | 9/2000 |
| WO | 00/59509 | 10/2000 |

OTHER PUBLICATIONS

U.S. patent application Ser. No. 09/436,892, Medford et al., filed Nov. 9, 1999.

Barnhart, J.W., et al., The Synthesis, Metabolism, and Biological Activity of Probucol and its Analogs, *Pharmacochem. Libr. No. 17,* (1991), pp. 277–299.

BioCentury Extra (The Bernstein Report of BioBusiness), "AtheroGenics: Faster than Anticipated," (Reprint from May 28, 2001).

Chemical Abstracts Service, Columbus, Ohio, US; STN, *Chemical Abstracts,* 28–Heterocyclic Compounds (More Than One Hetero Atom), vol. 124, No. 1, 1996, p. 921.

(List continued on next page.)

Primary Examiner—Paul J. Killos
(74) Attorney, Agent, or Firm—Sherry M. Knowles; Clark G. Sullivan; King & Spalding

(57) ABSTRACT

This invention is in the area of methods and compositions for the inhibition of the expression of VCAM-1 and, in particular, for the treatment of diseases mediated by VCAM-1, including cardiovascular and inflammatory diseases.

26 Claims, No Drawings

OTHER PUBLICATIONS

Chemical Abstracts Service, Columbus, Ohio, US; STN, *Chemical Abstracts*, 28–Heterocyclic Compounds (More Than One Hetero Atom), vol. 124, No. 11, 1996, p. 1251.

Cominacini et al., Antioxidants Inhibit the Expression of Intercellular Cell Adhesion Molecule–1 and Vascular Cell Adhesion Molecule–1 Induced by Oxidized LDL on Human Umbilical Vein Endothelial Cells, *Free Radical Biology & Medicine*, vol. 22, Nos. 1/2, pp. 117–127, 1997.

DeMeglio, P. et al., Farmaco, Ed. Sci., 40(11), 833–844 (1985) (partial English language translation).

Feldman et al., The in vitro and ex vivo antioxidant properties, and hypolipidemic activity of CGP 2881, *Atherosclerosis*, vol. 144, No. 2 (Jun. 1999), pp. 343–355.

Press Release, Nov. 12, 2001, "AtheroGenics Announces Positive Phase II Results From Cart–1 Clinical Trial For Restenosis".

Fruebis et al., A Comparison of the Antiatherogenic Effects of Probucol and of a Structural Analogue of Probucol in Low Density Lipoprotein Receptor–deficient Rabbits, *J. Clin. Invest.*, vol. 94, Jul. 1994, pp. 392–398.

Gershbein et al., Ation of Drugs and Chemical Agents on Rat Liver Regeneration, *Drug and Cheical Toxicology*, 8(3), 125–143 (1985).

Chemical Abstracts Service, Columbus, Ohio, US; STN, accession No. 122:187387J, see abstract, Kobayashi et al., vol. 122, 1995.

Chemical Abstracts Service, Columbus, Ohio, US; STN, accession No. 94:30290c, see abstract, Mamedov et al., vol. 94, 1981.

Mao et al., Attenuation of Atherosclerosis in a Modified Strain of Hypercholesterolemic Watanabe Rabbits With Use of a Probucol Analogue (MDL 29,311) That Does Not Lower Serum Cholesterol, *Arteriosclerosis and Thrombosis*, vol. 11, No. 4, Jul./Aug. 1991.

Mao et al., Antioxidant Activity of Probucol and Its Analogues in Hypercholesterolemic Watanabe Rabbits, *Journal of Medicinal Chemistry*, 1991, vol. 34, pp. 298–302.

Chemical Abstracts Service, Columbus, Ohio, US; STN, accession No. 86:5066m, see abstract; Medvedev et al., vol. 86, 1997, p. 437.

Chemical Abstracts Service, Columbus, Ohio, US; STN, accession No. 1970:445047, XP002124423; see abstract; Neuworth et al., *J. Med. Chem.*, (1970), vol. 13, No. 4, 722–725.

Chemical Abstracts Service, Columbus, Ohio, US; STN, accession No. 110:212254a, see abstract; Pastor et al., vol. 110, 1989.

Ramasamy et al., Modulation of Expression of Endothelial Nitric Oxide Synthase by Nordihydroguaiaretic Acid, a Phenolic Antioxdant in Cultured Endothelial Cells, *Modlecular Pharmacology*, vol. 56, No. 1, Jul. 1999, pp. 116–123.

Roberts et al., Regulation of monocyte to macrophage differentiation by antiglucocorticoids and antioxidants, *American Journal of Obstetrics and Gynecology*, vol. 179, No. 2, Aug. 1998, pp. 354–362.

Chemical Abstracts Service, Columbus, Ohio, US; STN, see abstract; Tomich et al., vol. 127, No. 6, 1997.

Chemical Abstracts Service, Columbus, Ohio, US; STN, accession No. 126:277465v, see abstract; Toshiaki et al., vol. 126, No. 21, 1997, p. 669.

Chemical Abstracts Service, Columbus, Ohio, US; STN, accession No. 86189w, see abstract; Wagner, Jr. et al., vol. 82, 1975.

COMPOUNDS AND METHODS FOR THE INHIBITION OF THE EXPRESSION OF VCAM-1

This application claims priority to U.S. provisional application Ser. No. 60/047,020 filed on May 14, 1997 and is a continuation of Ser. Nos. 09/370,046 and 09/079,213 filed Aug. 6, 1999 and May 14, 1998, respectively. Now U.S. Pat. No. 6,147,250.

This invention is in the area of methods and compositions for the inhibition of the expression of VCAM-1 and, in particular, for the treatment of diseases mediated by VCAM-1, including cardiovascular and inflammatory diseases.

BACKGROUND OF THE INVENTION

Coronary heart disease (CHD) remains the leading cause of death in the industrialized countries. The primary cause of CHD is atherosclerosis, a disease characterized by the deposition of lipids in the arterial vessel wall, resulting in a narrowing of the vessel passages and ultimately hardening the vascular system.

Atherosclerosis as manifested in its major clinical complication, ischemic heart disease, continues to be a major cause of death in industrialized countries. It is now well accepted that atherosclerosis can begin with local injury to the arterial endothelium followed by proliferation of arterial smooth muscle cells from the medial layer to the intimal layer along the deposition of lipid and accumulation of foam cells in the lesion. As the atherosclerotic plaque develops it progressively occludes more and more of the affected blood vessel and can eventually lead to ischaemia or infarction. Therefore, it is desirable to provide methods of inhibiting the progression of atherosclerosis in patients in need thereof.

Cardiovascular disease has been linked to several causative factors, which include hypercholesterolemia, hyperlipidemia, and the expression of VCAM-1 in vascular endothelial cells.

Expression of VCAM-1

Adhesion of leukocytes to the endothelium represents a fundamental, early event in a wide variety of inflammatory conditions, including atherosclerosis, autoimmune disorders and bacterial and viral infections. Leukocyte recruitment to the endothelium is started when inducible adhesion molecule receptors on the surface of endothelial cells interact with counterreceptors on immune cells. Vascular endothelial cells determine which type of leukocytes (monocytes, lymphocytes, or neutrophils) are recruited, by selectively expressing specific adhesion molecules, such as vascular cell adhesion molecule-1 (VCAM-1), intracellular adhesion molecule-1 (ICAM-1), and E-selectin. In the earliest stage of the atherosclerotic lesion, there is a localized endothelial expression of VCAM-1 and selective recruitment of mononuclear leukocytes that express the integrin counterreceptor VLA-4. Because of the selective expression of VLA-4 on monocytes and lymphocytes, but not neutrophils, VCAM-1 is important in mediating the selective adhesion of mononuclear leukocytes. Subsequent conversion of leucocytes to foamy macrophages results in the synthesis of a wide variety of inflammatory cytokines, growth factors, and chemoattractants that help propagate the leukocyte and platelet recruitment, smooth muscle cell proliferation, endothelial cell activation, and extracellular matrix synthesis characteristic of maturing atherosclerotic plaque.

VCAM-1 is a mediator in chronic inflammatory disorders such as asthma, rheumatoid arthritis and autoimmune diabetes. For example, it is known that the expression of VCAM-1 and ICAM-1 are increased in asthmatics. Pilewski, J. M., et al. *Am. J. Respir. Cell Mol. Biol.* 12, 1–3 (1995); Ohkawara, Y., et al., *Am. J. Respir. Cell Mol. Biol.* 12, 4–12 (1995). Additionally, blocking the integrin receptors for VCAM-1 and ICAM-1 (VLA-4 and LFA-1, respectively) suppressed both early and late phase responses in an ovalbumin-sensitized rat model of allergic airway responses. Rabb, 11. A., et al., *Am. J. Respir. Care Med.* 149, 1186–1191 (1994). There is also increased expression of endothelial adhesion molecules, including VCAM-1, in the microvasculature of rheumatoid synovium. Koch, A. E. et al., *Lab. Invest.* 64, 313–322 (1991); Morales-Ducret, J. et al., *Immunol.* 149, 1421–1431 (1992). Neutralizing antibodies directed against VCAM-1 or its counter receptor, VLA-4, can delay the onset of diabetes in a mouse model (NOD mice) which spontaneously develop the disease. Yang, X. D. et al., *Proc. Natl. Acad. Sci. U.S.A.* 90, 10494–10498 (1993); Burkly, L. C. et al., *Diabetes* 43, 523–534 (1994); Baron, J. L. et al., *J. Clin. Invest.* 93, 1700–1708 (1994). Monoclonal antibodies to VCAM-1 can also have a beneficial effect in animal models of allograft rejection, suggesting that inhibitors of VCAM-1 expression may have utility in preventing transplant rejection. Oroez, C. G. et al., *Immunol. Lett.* 32, 7–12 (1992).

VCAM-1 is expressed by cells both as a membrane bound form and as a soluble form. The soluble form of VCAM-1 has been shown to induce chemotaxis of vascular endothelial cells in vitro and stimulate an angiogenic response in rat cornea. Koch, A. F. et al., *Nature* 376, 517–519 (1995). Inhibitors of the expression of soluble VCAM-1 have potential therapeutic value in treating diseases with a strong angiogenic component, including tumor growth and metastasis. Folkman, J., and Shing, Y., *Biol. Chem.* 10931–10934 (1992).

VCAM-1 is expressed in cultured human vascular endothelial cells after activation by lipopolysaccharide (LPS) and cytokines such as interleukin-1 (IL-1) and tumor necrosis factor (TNF-α). These factors are not selective for activation of cell adhesion molecule expression.

U.S. Pat. No. 5,380,747 to Medford, et al., teaches the use of dithiocarbamates such as pyrrolidine dithiocarbamate for the treatment of cardiovascular and other inflammatory diseases.

U.S. Pat. No. 5,750,351 to Medford, et al., and WO95/30415 to Emory University describe the discovery that polyunsaturated fatty acids ("PUFAs") and their hydroperoxides ("ox-PUFAs"), which are important components of oxidatively modified low density lipoprotein (LDL), induce the expression of VCAM-1, but not intracellular adhesion molecule-1 (ICAM-1) or E-selectin in human aortic endothelial cells, through a mechanism that is not mediated by cytokines or other noncytokine signals. This is a fundamental discovery of an important and previously unknown biological pathway in VCAM-1 mediated immune responses.

As non-limiting examples, linoleic acid, linolenic acid, arachidonic acid, linoleyl hydroperoxide (13-HPODE) and arachidonic hydroperoxide (15-HPETE) induce cell-surface gene expression of VCAM-1 but not ICAM-1 or E-selectin. Saturated fatty acids (such as stearic acid) and monounsaturated fatty acids (such as oleic acid) do not induce the expression of VCAM-1, ICAM-1 or E-selectin.

The induction of VCAM-1 by PUFAs and their fatty acid hydroperoxides is suppressed by dithiocarbamates, including pyrrolidine dithiocarbamate (PDTC). This indicates that the induction is mediated by an oxidized signal molecule, and that the induction is prevented when the oxidation of the molecule is blocked (i.e., the oxidation does not occur), reversed (i.e., the signal molecule is reduced), or when the redox modified signal is otherwise prevented from interacting with its regulatory target.

Cells that are chronically exposed to higher than normal levels of polyunsaturated fatty acids or their oxidized counterparts can initiate an immune response that is not normal and which is out of proportion to the threat presented, leading to a diseased state. The oversensitization of vascular endothelial cells to PUFAs and ox-PUFAs can accelerate the formation, for example, of atherosclerotic plaque.

Based on these discoveries, a method for the treatment of atherosclerosis, post-angioplasty restenosis, coronary artery diseases, angina, small artery disease and other cardiovascular diseases, as well as noncardiovascular inflammatory diseases that are mediated by VCAM-1, was described in WO95/30415 that includes the removal, decrease in the concentration of, or prevention of the formation of oxidized polyunsaturated fatty acids including but not limited to oxidized linoleic ($C_{18}\Delta^{9,12}$), linolenic ($C_{18}\Delta^{6,9,12}$), arachidonic ($C_{20}\Delta^{5,8,11,14}$) and eicosatrienoic ($C_{20}\Delta^{8,11,14}$) acids.

Nonlimiting examples of noncardiovascular inflammatory diseases that are mediated by VCAM-1 include rheumatoid and osteoarthritis, asthma, dermatitis, and multiple sclerosis.

Hypercholesterolemia and Hyperlipidemia

Hypercholesterolemia is an important risk factor associated with cardiovascular disease. Serum lipoproteins are the carriers for lipids in the circulation. Lipoproteins are classified according to their density: chylomicrons, very low-density lipoproteins (VLDL), low density lipoproteins (LDL) and high-density lipoproteins (HDL). Chylomicrons primarily participate in transporting dietary triglycerides and cholesterol from the intestine to adipose tissue and liver. VLDL deliver endogenously synthesized triglycerides from liver to adipose and other tissues. LDL transports cholesterol to peripheral tissues and regulate endogenous cholesterol levels in those tissues. HDL transports cholesterol from peripheral tissues to the liver. Arterial wall cholesterol is derived almost exclusively from LDL. Brown and Goldstein, Ann. Rev. Biochem. 52, 223 (1983); Miller, Ann. Rev. Med. 31, 97 (1980). In patients with low levels of LDL, the development of atherosclerosis is rare.

Steinberg, et al., (N. Eng. J. Med. 1989; 320:915–924) hypothesized that modification of low-density lipoprotein (LDL) into oxidatively modified LDL (ox-LDL) by reactive oxygen species is the central event that initiates and propagates atherosclerosis. Oxidized LDL is a complex structure consisting of at least several chemically distinct oxidized materials, each of which, alone or in combination, may modulate cytokine-activated adhesion molecule gene expression. R fatty acid hydroperoxides such as linoleyl hydroperoxide (13-HPODE) are produced from free fatty acids by lipoxygenases and are an important component of oxidized LDL.

It has been proposed that a generation of oxidized lipids is formed by the action of the cell lipoxygenase system and that the oxidized lipids are subsequently transferred to LDL. There is thereafter a propagation reaction within the LDL in the medium catalyzed by transition metals and/or sulfhydryl compounds. Previous investigations have demonstrated that fatty acid modification of cultured endothelial cells can alter their susceptibility to oxidant injury, whereas supplementation with polyunsaturated fatty acids (PUFA) enhances susceptibility to oxidant injury. Supplementation of saturated or monounsaturated fatty acids to cultured endothelial cells reduces their susceptibility to oxidant injury, whereas supplementation with polyunsaturated fatty acids (PUFA) enhances susceptibility to oxidant injury.

Using reverse-phase HPLC analysis of native and saponified liquid extracts of LDL, it has been demonstrated that 13-HPODE is the predominant oxidized fatty acid in LDL oxidized by activated human monocytes. Chronic exposure to oxidized LDL provides an oxidative signal to vascular endothelial cells, possible through a specific fatty acid hydroperoxide, that selectively augments cytokine-induced VCAM-1 gene expression.

Through a mechanism that is not well defined, areas of vessel wall predisposed to atherosclerosis preferentially sequester circulating LDL. Through a poorly understood pathway, endothelial, smooth muscle, and/or inflammatory cells then convert LDL to ox-LDL. In contrast to LDL, which is taken up through the LDL receptor, monocytes avidly take up ox-LDL through a "scavenger" receptor whose expression, unlike the LDL receptor, is not inhibited as the content of intracellular lipid rises. Thus, monocytes continue to take up ox-LDL and become lipid-engorged macrophage-foam cells that form the fatty streak.

There is now a large body of evidence demonstrating that hypercholesterolemia is an important risk factor associated with heart disease. For example, in December 1984, a National Institute of Health Consensus Development Conference Panel concluded that lowering definitely elevated blood cholesterol levels (specifically blood levels of low-density lipoprotein cholesterol) will reduce the risk of heart attacks due to coronary heart disease.

Typically, cholesterol is carried in the blood of warm-blooded animals in certain lipid-protein complexes such as chylomicrons, very low density lipoprotein (VLDL), low density lipoprotein (LDL), and high density lipoprotein (HAL). It is widely accepted that LDL functions in a way that directly results in deposition of the LDL cholesterol in the blood-vessel wall and that HDL functions in way that results in the HDL picking up cholesterol from the vessel wall and transporting it to the liver where it is metabolized [Brown and Goldstein, Ann. Rev. Biochem. 52, 223 (1983); Miller, Ann. Rev. Med. 31, 97 (1980)]. For example, in various epidemiologic studies the LDL cholesterol levels correlate well with the risk of coronary heart disease whereas the HDL cholesterol levels are inversely associated with coronary heart disease [Patton et al., Clin. Chem. 29, 1980 (1983)]. It is generally accepted by those skilled in the art that reduction of abnormally high LDL cholesterol levels is effective therapy not only in the treatment of hypercholesterolemia but also in the treatment of atherosclerosis.

Furthermore, there is evidence based on animal and laboratory findings that peroxidation of LDL lipid, such as the unsaturated fatty acid portions of LDL cholesteryl esters and phospholipids, facilitate the accumulation of cholesterol in monocyte/macrophages which eventually are transformed into foam cells and become deposited in the sub-endothelial space of the vessel wall. The accumulation of foam cells in the vessel wall is recognized as an early event in the formation of an atherosclerotic plaque. Thus it is believed that peroxidation of LDL lipid is an important prerequisite to the facilitated accumulation of cholesterol in the vessel wall and the subsequent formation of an atherosclerotic plaque. For example, it has been shown that monocyte/macrophages take up and degrade native LDL at relatively low rates and without marked accumulation of cholesterol. In contrast, oxidized LDL is taken up by these monocyte/macrophages at much higher rates and with marked accumulation of cholesterol [Parthasarathy et al., *J. Clin. Invest.* 77,641 (1986)]. It is therefore desirable to provide methods of inhibiting LDL lipid peroxidation in a patient in need thereof.

Elevated cholesterol levels are associated with a number of disease states, including restenosis, angina, cerebral atherosclerosis, and xanthoma. It is desirable to provide a method for reducing plasma cholesterol in patients with, or at risk of developing, restenosis, angina, cerebral arteriosclerosis, xanthoma, and other disease states associated with elevated cholesterol levels.

Since it has been determined that hypercholesterolemia is due to elevated LDL (hyperlipidemia), the lowering of LDL levels by dietary therapy is attempted. There are several drug classes that are commonly used to lower LDL levels, including bile acid sequestrants, nicotinic acid (niacin), and 3-hydroxy-3-methylglutaryl coenzyme A (HMG CoA) reductase inhibitors. Probucol and the fibrate derivatives are sometimes used as adjunctive therapy, usually in combination with other medications. The HMG CoA reductase inhibitors have been termed statins or vastatins. Statins are among the most effective agents currently on the market for hypercholesterolemia, and include pravastatin (Pravchol, Bristol Myers Squibb), atorvastatin (Warner Lambert/Pfizer), simvastatin (Zocor, Merck), lovastatin (Mevacor, Merck), and fluvastatin (Lescol).

Evidence suggests that the atherogenic effects of low density lipoprotein (LDL) may be in part mediated through its oxidative modification. Probucol has been shown to possess potent antioxidant properties and to block oxidative modification of LDL. Consistent with these findings, probucol has been shown to actually slow the progression of atherosclerosis in LDL receptor-deficient rabbits as discussed in Carew et al. *Proc. Natl. Acad. Sci. U.S.A.* 84:7725–7729 (1987). Most likely, probucol is effective because it is highly lipid soluble and is transported by lipoproteins, thus protecting them against oxidative damage.

Probucol is chemically related to the widely used food additives 2,[3]-tert-butyl-4-hydroxyanisole (BRA) and 2,6-di-tert-butyl-4-methyl phenol (3HT). Its full chemical name is 4,4'-(isopropylidenedithio) bis(2,6-di-tert-butylphenol).

Probucol is used primarily to lower serum cholesterol levels in hypercholesterolemic patients. Probucol is commonly administered in the form of tablets available under the trademark Lorelco™. Unfortunately, probucol is almost insoluble in water and therefore cannot be injected intravenously. In fact, probucol is difficult for cells to absorb in vitro because of its poor miscibility in buffers and media for cell culture. Solid probucol is poorly absorbed into the blood, and is excreted in substantially unchanged form. Further, the tablet form of probucol is absorbed at significantly different rates and in different amounts by different patients. In one study (Heeg et al., *Plasma Levels of Probucol in Man After Single and Repeated Oral Doses*, La Nouvelle Presse Medicale, 9:2990–2994 (1980)), peak levels of probucol in sera were found to differ by as much as a factor of 20 from patient to patient. In another study, Kazuya et al. J. Lipid Res. 32; 197–204 (1991) observed an incorporation of less than about 1 $\mu$g of probucol/$10^6$ cells when endothelial cells are incubated for 24 h with 50 $\mu$M probucol.

U.S. Pat. No. 5,262,439 to Parthasarathy discloses analogs of probucol with increased water solubility in which one or both of the hydroxyl groups are replaced with ester groups that increase the water solubility of the compound. In one embodiment, the derivative is selected from the group consisting of a mono- or di-probucol ester of succinic acid, glutaric acid, adipic acid, seberic acid, sebacic acid, azelaic acid, or maleic acid. In another embodiment, the probucol derivative is a mono- or di-ester in which the ester contains an alkyl or alkenyl group that contains a functionality selected from the group consisting of a carboxylic acid group, amine group, salt of an amine group, amide groups, amide groups, and aldehyde groups.

A series of French patents disclose that certain probucol derivatives are hypocholesterolemic and hypolipemic agents: Fr 2168137 (bis 4-hydroxyphenylthioalkane esters); Fr 2140771 (tetralinyl phenoxy alkanoic esters of probucol); Fr 2140769 (benzofuryloxyalkanoic acid derivatives of probucol); Fr 2134810 (bis-(3-allyl-5-t-alkyl-4-thiazole-5-carboxy)phenylthio)alkanes; FR 2133024 (bis-(4-nicotinoyloxyphenylthio)propanes; and Fr 2130975 (bis(4-(phenoxyalkanoyloxy)-phenylthio)alkanes).

U.S. Pat. No. 5,155,250 to Parker, et al. discloses that 2,6-dialkyl-4-silylphenols are antiatherosclerotic agents. The same compounds are disclosed as serum cholesterol lowering agents in PCT Publication No. WO 95/15760, published on Jun. 15, 1995. U.S. Pat. No. 5,608,095 to Parker, et al. discloses that alkylated-4-silyl-phenols inhibit the peroxidation of LDL, lower plasma cholesterol, and inhibit the expression of VCAM-1, and thus are useful in the treatment of atherosclerosis.

A series of European patent applications and to Shionogi Seiyaku Kabushiki Kaisha disclose phenolic thioethers for use in treating arteriosclerosis. European Patent Application No. 348 203 discloses phenolic thioethers which inhibit the denaturation of LDL and the incorporation of LDL by macrophages. The compounds are useful as anti-arteriosclerosis agents. Hydroxamic acid derivatives of these compounds are disclosed in European Patent Application No. 405 788 and are useful for the treatment of arteriosclerosis, ulcer, inflammation and allergy. Carbamoyl and cyano derivatives of the phenolic thioethers are disclosed in U.S. Pat. No. 4,954,514 to Kita, et al.

U.S. Pat. No. 4,752,616 to Hall, et al., disclose arylthio-alkylphenylcarboxylic acids for the treatment of thrombotic disease. The compounds disclosed are useful as platelet aggregation inhibitors for the treatment of coronary or cerebral thromboses and the inhibition of bronchoconstriction, among others.

A series of patents to Adir et Compagnie disclose substituted phenoxyisobutyric acids and esters useful as antioxidants and hypolipaemic agents. This series includes U.S. Pat. Nos. 5,206,247 and 5,627,205 to Regnier, et al. (which corresponds to European Patent Application No. 621 255) and European Patent Application No. 763 527.

WO97/15546 to Nippon Shinyaku Co. Ltd. discloses carboxylic acid derivatives for the treatment of arterial sclerosis, ischemic heart diseases, cerebral infarction and post PTCA restenosis.

The Dow Chemical Company is the assignee of patents to hypolipidemic2-(3,5-di-tert-butyl-4-hydroxyphenyl)thio carboxamides. For example, U.S. Pat. Nos. 4,029,812, 4,076,841 and 4,078,084 to Wagner, et al., disclose these compounds for reducing blood serum lipids, especially cholesterol and triglyceride levels.

Given that cardiovascular disease is currently the leading cause of death in the United States, and ninety percent of cardiovascular disease is presently diagnosed as atherosclerosis, there is a strong need to identify new methods and pharmaceutical agents for its treatment. Important to this goal is the identification and manipulation of the specific oxidized biological compounds that act as selective regulators of the expression of mediators of the inflammatory process, and in particular, VCAM-1. A more general goal is to identify selective methods for suppressing the expression of redox sensitive genes or activating redox sensitive genes that are suppressed.

It is therefore an object of the present invention to provide new compounds, compositions and methods for the treatment of cardiovascular and inflammatory diseases.

It is still another object of the present invention to provide new compounds and compositions which are useful as inhibitors of LDL lipid peroxidation.

It is still another object of the present invention to provide new compounds and compositions which are useful as antiatherosclerotic agents.

It is still another object of the present invention to provide new compounds and compositions which are useful as LDL lipid lowering agents.

It is still another object of the present invention to provide new compounds, compositions and methods for selectively inhibiting the expression of VCAM-1.

It is still another object of the present invention to provide a method for the treatment of a disease that is mediated by the expression or suppression of a redox sensitive gene, for example MCP-1, IL-6 and thrombin receptor.

SUMMARY OF THE INVENTION

The present invention provides a compound, composition and method for inhibiting the expression of VCAM-1, and thus can be used in the treatment of a disease mediated by VCAM-1, which includes administering a compound of formula (I) or (II), or a pharmaceutically acceptable salt thereof, optionally in a pharmaceutically acceptable carrier. The compounds of formula (I) are

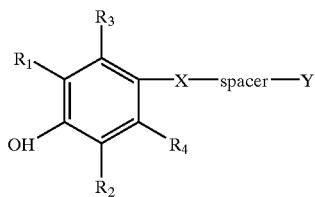

(I)

wherein

X is O, S, SO, $SO_2$, $CH_2$, or NH;

Spacer is a group selected from the group consisting of —$(CH_2)_n$—, —$(CH_2)_n$—CO—, —$(CH_2)_n$—N—, —$(CH_2)_n$—O—, —$(CH_2)_n$—S—, —$(CH_2O\ )_n$—, —$(OCH_2)$—, —$(SCH_2)$—, —$(CH_2S$—), —(aryl-O)—, —(O-aryl)—, -(alkyl-O)—, —(O-alkyl)-;

n is 0, 1, 2, 3, 4, 5, 6, 7, 8, 9, or 10;

Y is substituted or unsubstituted aryl, substituted or unsubstituted heteroaryl, substituted or unsubstituted alkyl, substituted or unsubstituted alkoxy, substituted or unsubstituted alkoxyalkyl, substituted or unsubstituted alkylthio, substituted or unsubstituted alkylthioalkyl, substituted or unsubstituted alkylsulfinyl, substituted or unsubstituted alkylsulfinylalkyl, substituted or unsubstituted alkylsulfonyl, substituted or unsubstituted alkylsulfonylalkyl, $NH_2$, NHR, $NR_2$, $SO_2$—OH, OC(O)R, C(O)OH, C(O)OR, C(O)$NH_2$, C(O)NHR, C(O)$NR_2$, $SO_2NH_2$, $SO_2$NHR, $SO_2NR_2$;

R is alkyl, substituted alkyl, alkenyl, substituted alkenyl, alkynyl, substituted alkynyl, aryl, substituted aryl, alkyl-COOH, alkyl-COOalkyl, alkyl-COOaryl, heteroaryl, substituted heteroaryl, or when attached to a nitrogen atom, two adjacent R groups may combine to form a ring of 5 to 7 members;

$R^1$ and $R^2$ are independently straight chained, branched, or cyclic alkyl which may be substituted, aryl, substituted aryl, heteroaryl, substituted heteroaryl, alkaryl, or aralkyl; and wherein substituents on the $R^1$ or $R^2$ groups are selected from the group consisting of hydrogen, halogen, alkyl, nitro, amino, alkylamino, dialkylamino, acyl, and acyloxy;

$R^3$ and $R^4$ are independently any group that does not otherwise adversely affect the desired properties of the molecule, including H, halogen, or $R^1$.

The compound of formula (II) has the following structure

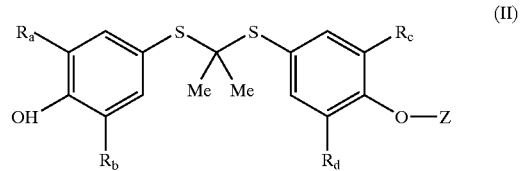

(II)

wherein $R_a$, $R_b$, $R_c$, and $R_d$ are independently any group that does not otherwise adversely affect the desired properties of the molecule, including hydrogen, straight chained, branched, or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —$(CH_2)$—$R_e$, —C(O)—$R_g$, and —C(O)—$(CH_2)_n$—$R_h$, wherein (a) when each of $R_a$, $R_b$, $R_c$, and $R_d$ are t-butyl, Z cannot be hydrogen and (b) when each of $R_a$, $R_b$, $R_c$, and $R_d$ are t-butyl, Z cannot be the residue of succinic acid;

$R_e$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, C(O)$NH_2$, C(O)NH, C(O)$NR_2$;

$R_g$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl;

$R_h$ is selected from the group consisting of alkyl, substituted alkyl, alkenyl, substituted alkenyl, alkynyl, substituted alkynyl, alkoxy, substituted alkyloxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)R$_f$, hydroxy, O-phosphate, C(O)NH$_2$, C(O)N, C(O)NR$_2$ and pharmaceutically acceptable salts thereof;

Or, in an alternative embodiment, R$_e$, R$_g$, and R$_h$ can independently be a substituent which improves the water solubility of the compound, including, but not limited to C(O)-spacer-SO$_3$H, wherein spacer is as defined above, C(O)-spacer-SO$_3$M, wherein M is a metal used to form a pharmaceutically acceptable salt, for example, sodium, C(O)-spacer-PO$_3$H$_2$, C(O)-spacer-PO$_3$M$_2$, C(O)-spacer-PO$_3$HM, C(O)-spacer-PO$_4$H, C(O)-spacer-PO$_4$M, SO$_3$M, —PO$_3$H$_2$, —PO$_3$M$_2$, —PO$_3$HM, cyclic phosphates, polyhydroxyalkyl, carbohydrate groups, C(O)-spacer-[O(C$_{1-3}$ alkyl)$_p$]$_n$, wherein n is as defined above and p is 1, 2, or 3, —[O(C$_{1-3}$ allyl)$_p$]$_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

The present invention generally provides a method for treating cardiovascular and inflammatory disorders in a patient in need thereof comprising administering to said patient an effective amount of a compound of formula (I) or formula (II).

The present invention further provides a method of inhibiting the peroxidation of LDL lipid in a patient in need thereof comprising administering to said patient an effective antioxidant amount of a compound of formula (I) or formula (II).

In an alternative embodiment, a method is provided for suppressing the expression of a redox-sensitive gene or activating a gene that is suppressed through a redox-sensitive pathway, that includes administering an effective amount to prevent the oxidation of the oxidized signal, and typically, the oxidation of a PUFA of a compound of formula (I) or formula (II). Representative redox-sensitive genes that are involved in the presentation of an immune response include, but are not limited to, those expressing cytokines involved in initiating the immune response (e.g., IL-1β), chemoattractants that promote the migration of inflammatory cells to a point of injury (e.g., MCP-1), growth factors (e.g., IL-6 and the thrombin receptor), and adhesion molecules (e.g., VCAM-1 and E-selectin).

DETAILED DESCRIPTION OF THE INVENTION

The term alkyl, as used herein, unless otherwise specified, refers to a saturated straight, branched, or cyclic, primary, secondary, or tertiary hydrocarbon of C$_1$ to C$_{10}$, and specifically includes methyl, ethyl, propyl, isopropyl, cyclopropyl, butyl, isobutyl, t-butyl, pentyl, cyclopentyl, isopentyl, neopentyl, hexyl, isohexyl, cyclohexyl, cyclohexylmethyl, 3-methylpentyl, 2,2-dimethylbutyl, and 2,3-dimethylbutyl. The alkyl group can be optionally substituted with one or more moieties selected from the group consisting of alkyl, halo, hydroxyl, carboxyl, acyl, acyloxy, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term lower alkyl, as used herein, and unless otherwise specified, refers to a C$_1$ to C$_5$ saturated straight, branched, or if appropriate, a cyclic (for example, cyclopropyl) alkyl group.

Likewise the term alkylene refers to a saturated hydrocarbyldiyl radical of straight or branched configuration made up of from one to ten carbon atoms. Included within the scope of this term are methylene, 1,2-ethane-diyl, 1,1-ethane-diyl, 1,3-propane-diyl, 1,2-propane-diyl, 1,3-butane-diyl, 1,4-butane-diyl and the like. The alkylene group can be optionally substituted with one or more moieties selected from the group consisting of alkyl, halo, hydroxyl, carboxyl, acyl, acyloxy, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991, hereby incorporated by reference.

The term "—(CH$_2$)$_n$—" represents a saturated hydrocarbyldiyl radical of straight chain configuration. The term "n" is defined as 0–10. The moiety "—(CH$_2$)$_n$—" thus represents a bond (i.e., when n=0), methylene, 1,2-ethanediyl or 1,3-propanediyl, etc.

The term aryl, as used herein, and unless otherwise specified, refers to phenyl, biphenyl, or naphthyl, and preferably phenyl. The term aralkyl, as used herein, and unless otherwise specified, refers to an aryl group as defined above linked to the molecule through an alkyl group as defined above. The term alkaryl, as used herein, and unless otherwise specified, refers to an alkyl group as defined above linked to the molecule through an aryl group as defined above. In each of these groups, the alkyl group can be optionally substituted as describe above and the aryl group can be optionally substituted with one or more moieties selected from the group consisting of alkyl, halo, hydroxyl, carboxyl, acyl, acyloxy, amino, alkylamino, arylamino, alkoxy, aryloxy, nitro, cyano, sulfonic acid, sulfate, phosphonic acid, phosphate, or phosphonate, either unprotected, or protected as necessary, as known to those skilled in the art, for example, as taught in Greene, et al., *Protective Groups in Organic Synthesis*, John Wiley and Sons, Second Edition, 1991. Specifically included within the scope of the term aryl are phenyl; naphthyl; phenylmethyl; phenylethyl; 3,4,5-trihydroxyphenyl; 3,4,5-trimethoxyphenyl; 3,4,5-triethoxyphenyl; 4-chlorophenyl; 4-methylphenyl; 3,5-di-tertiarybutyl-4-hydroxyphenyl; 4-fluorophenyl; 4-chloro-1-naphthyl; 2-methyl-1-naphthylmethyl; 2-naphthylmethyl; 4-chlorophenylmethyl; 4-tertiarybutylphenyl; 4-tertiarybutylphenylmethyl and the like.

The term "protected" as used herein and unless otherwise defined refers to a group that is added to an oxygen, nitrogen, or phosphorus atom to prevent its further reaction or for other purposes. A wide variety of oxygen and nitrogen protecting groups are known to those skilled in the art of organic synthesis.

The term halo, as used herein, includes chloro, bromo, iodo, and fluoro.

The term alkoxy, as used herein, and unless otherwise specified, refers to a moiety of the structure —O-alkyl, wherein alkyl is as defined above.

The term acyl, as used herein, refers to a group of the formula C(O)R', wherein R' is an alkyl, aryl, alkaryl or aralkyl group, or substituted alkyl, aryl, aralkyl or alkaryl, wherein these groups are as defined above.

As used herein, the term polyunsaturated fatty acid (PUFA) refers to a fatty acid (typically $C_8$ to $C_{24}$) that has at least two alkenyl bonds, and includes but is not limited to linoleic ($C_{18}\Delta^{9,12}$), linolenic ($C_{18}\Delta^{6,9,12}$), arachidonic ($C_{20}\Delta^{8,11,14}$) acids.

The term oxidized polyunsaturated fatty acid (ox-PUFA) refers to an unsaturated fatty acid in which at least on of the alkenyl bonds has been converted to a hydroperoxide Nonlimiting examples are 13-HPODE and 15-HPETE.

The term pharmaceutically acceptable salts or complexes refers to salts or complexes that retain the desired biological activity of the compounds of the present invention and exhibit minimal undesired toxicological effects. Nonlimiting examples of such salts are (a) acid addition salts formed with inorganic acids (for example, hydrochloric acid, hydrobromic acid, sulfuric acid, phosphoric acid, nitric acid, and the like), and salts formed with organic acids such as acetic acid, oxalic acid, tartaric acid, succinic acid, malic acid, ascorbic acid, benzoic acid, tannic acid, pamoic acid, alginic acid, polyglutamic acid, naphthalenesulfonic acid, naphthalenedisulfonic acid, and polygalcturonic acid; (b) base addition salts formed with metal cations such as zinc, calcium, bismuth, barium, magnesium, aluminum, copper, cobalt, nickel, cadmium, sodium, potassium, and the like, or with a cation formed from ammonia, N,N-dibenzylethylenediamine, D-glucosamine, tetraethylammonium, or ethylenediamine; or (c) combinations of (a) and (b); e.g., a zinc tannate salt or the like. Also included in this definition are pharmaceutically acceptable quaternary salts known by those skilled in the art, which specifically include the quaternary ammonium salt of the formula —$NR^+A^-$, wherein R is as defined above and A is a counterion, including chloride, bromide, iodide, —O-alkyl, toluenesulfonate, methylsulfonate, sulfonate, phosphate, or carboxylate (such as benzoate, succinate, acetate, glycolate, maleate, malate, citrate, tartrate, ascorbate, benzoate, cinnamoate, mandeloate, benzyloate, and diphenylacetate).

Diseases mediated by the VCAM-1 include, but are not limited to atherosclerosis, post-angioplasty restenosis, coronary artery disease, angina, small artery disease, and other cardiovascular diseases, as well as noncardiovascular inflammatory diseases such as rheumatoid arthritis, osteoarthritis, asthma, dermatitis, multiple sclerosis and psoriasis.

In one embodiment, the invention is a method for treating a disease mediated by the expression of VCAM-1 comprising administering a compound of the formula

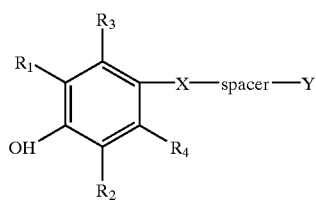

(I)

wherein

X is O, S, SO, $SO_2$, $CH_2$, or NH;

Spacer is a group selected from the group consisting of —$(CH_2)_n$—, —$(CH_2)_n$—CO—, —$(CH_2)_n$—N—, —$(CH_2)_n$—O—, —$(CH_2)_n$—S—, —$(CH_2O)$—, —$(OCH_2)$—, —$(SCH_2)$—, —$(CH_2S)$—, -(aryl-O)—, —(O-aryl), -(alkyl-O)—, —(O-alkyl)-;

n is 0, 1, 2, 3, 4, 5, 6, 7, 8, 9, or 10;

Y is substituted or unsubstituted aryl, substituted or unsubstituted heteroaryl, substituted or unsubstituted alkyl, $NH_2$, NHR, $NR_2$, $SO_2$—OH, OC(O)R, C(O)OH, C(O)OR, C(O)$NH_2$, C(O)NHR, C(O)$NR_2$;

R is alkyl, substituted alkyl, alkenyl, substituted alkenyl, alkynyl, substituted alkynyl, aryl, substituted aryl, alkyl-COOH, alkyl-COOalkyl, alkyl-COOaryl, heteroaryl, substituted heteroaryl, or when attached to a nitrogen atom, two adjacent R groups may combine to form a ring of 5 to 7 members;

$R^1$ and $R^2$ are independently straight chained, branched, or cyclic alkyl which may be substituted, aryl, substituted aryl, heteroaryl, substituted heteroaryl, alkaryl, or aralkyl; and wherein substituents on the $R^1$ or $R^2$ groups are selected from the group consisting of hydrogen, halogen, alkyl, nitro, amino, alkylamino, dialkylamino, acyl, and acyloxy;

$R^3$ and $R^4$ are independently any group that does not otherwise adversely affect the desired properties of the molecule, including H, halogen, or $R^1$.

Preferred compounds of the present invention include compounds of formula (I) wherein X is S, SO or $SO_2$; Spacer is —$(CH_2)_n$— or —$(CH_2)_n$CO—; n is 0–10; Y is aryl, substituted aryl, heteroaryl, substituted heteroaryl, $NH_2$, NHR, $NR_2$, alkyl, substituted alkyl, acyloxy, and substituted acyloxy; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently straight chained, branched or cyclic $C_{1-10}$ alkyl; $R^3$ and $R^4$ are independently hydrogen, halogen or $R^1$.

Another preferred embodiment of the present invention includes compounds of formula (I) wherein X is S, SO, or $SO_2$; Spacer is —$(CH_2)_n$— or —$(CH_2)_n$—CO—; n is 0–10; Y is aryl, substituted aryl, heteroaryl, substituted heteroaryl, $NH_2$, NHR, $NR_2$, alkyl, substituted alkyl, acyloxy, and substituted acyloxy; R is alkyl, alkenyl, alkynyl, aryl, alkyl-COOH, alkyl-COalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently straight chained, branched or cyclic $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is aryl; aryl which is mono- or polysubstituted by alkyl, alkenyl, alkynyl, halo, nitro, hydroxy, COOH, COOR, CONH$_2$, CONHR, CONR$_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; heteroaryl; heteroaryl which is mono- or polysubstituted by alkyl, alkenyl, alkynyl, $CH_2NH_2$, $CH_2NHR$, $CH_2NR_2$, COOH, COOR; $NH_2$; NHR; $NR_2$; straight chained, branched or cyclic alkyl; straight chained, branched, or cyclic alkyl substituted by OCOR, $SO_2OH$, COOH or COOR; and OCOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is aryl; aryl which is mono- or polysubstituted by alkyl, alkenyl, alkynyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is phenyl; phenyl which is mono- or polysubstituted by alkyl, alkenyl, alkynyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkenyl, alkynyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—; n is 0–10; Y is phenyl; phenyl which is mono- or polysubstituted by alkyl, alkenyl, alkynyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkenyl, alkynyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; the R group may be further substituted by alkyl, alkyl-COOH, alkyl-COOalkyl, or alkyl-COOaryl; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—CO—; n is 0–10; Y is phenyl; phenyl which is mono- or polysubstituted by alkyl, alkenyl, alkynyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is phenyl; phenyl which is mono- or polysubstituted by alkyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkyl-COOH, alkyl-COOalkyl, alkyl-COOaryl, aryl, heteroaryl or nitro-substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is phenyl; phenyl which is mono- or polysubstituted by alkyl, halo, nitro, hydroxy, COOH, COOR, $CONH_2$, CONHR, $CONR_2$, —$(CH_2)_m$—OH wherein m is 0–10, haloalkyl, mono- or poly-hydroxysubstituted branched alkyl, a carbohydrate group, $SO_2OH$, $SO_2NH_2$, $SO_2NHR$, $SO_2NR_2$, or OCOR; R is alkyl, alkyl-COOH, alkyl-COOalkyl, alkyl-COOaryl, or nitro-substituted furanyl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is heteroaryl; heteroaryl which is mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—; n is 0–10; Y is heteroaryl; heteroaryl which is mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—CO—; n is 0–10; Y is heteroaryl; heteroaryl which is mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is isoxazolyl or furanyl which may be optionally substituted by mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is isoxazolyl which may be optionally substituted by mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is furanyl which may be optionally substituted by mono- or polysubstituted by alkyl, alkenyl, alkynyl, $CH_2NH_2$, $CH_2NHR$, $CH_2NR_2$, COOH, COOR; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is $NH_2$, NHR or $NR_2$; R is alkyl, alkenyl, alkynyl, aryl, alkyl-COOH, alkyl-COOalkyl, alkyl-COOaryl, heteroaryl, or nitro substituted heteroaryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is $NH_2$, NHR or $NR_2$; R is alkyl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—; n is 0–10; Y is $NH_2$, NHR or $NR_2$; R is alkyl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—CO—; n is 0–10; Y is $NH_2$, NHR or $NR_2$; R is alkyl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is selected from the group consisting of straight chained, branched or cyclic alkyl; straight chained, branched, or cyclic alkyl substituted by OCOR, $SO_2OH$, COOH or COOR; and OCOR; R is alkyl, alkenyl, alkynyl, and aryl, or when attached to a nitrogen atom, two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is selected from the group consisting of straight chained, branched or cyclic alkyl; straight chained, branched, or cyclic alkyl substituted by OCOR, $SO_2OH$, COOH or COOR; and OCOR; R is alkyl or two adjacent R groups may combine to form a ring of 5 to 7 members; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—; n is 0–10; Y is selected from the group consisting of straight chained, branched or cyclic alkyl; straight chained, branched, or cyclic alkyl substituted by OCOR, $SO_2OH$, COOH; or COOR; R is alkyl; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—CO—; n is 0–10; Y is selected from the group consisting of straight chained, branched or cyclic alkyl; straight chained, branched, or cyclic alkyl substituted by OCOR; R is alkyl; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$— or —$(CH_2)_n$—CO—; n is 0–10; Y is OCOR; R is alkyl; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—; n is 0–10; Y is OCOR; R is alkyl; $R^1$ and $R^2$ are independently $C_{1-5}$ alkyl; $R^3$ and $R^4$ are independently H.

Another preferred embodiment of the present invention includes compounds of formula (I) wherein X is S, SO, or $SO_2$; Spacer is —$(CH_2)_n$—CO—; n is 0–10; Y is OCOR; R is alkyl; $R^1$ and $R^2$ are independently $C_{1-5}$ alkyl; $R^3$ and $R^4$ are independently H.

Examples of the present invention include compounds of formula (I) defined as follows:

X=S; $R^1$=t-butyl; $R^2$=t-butyl; $R^3$=H; $R^4$=H; Space=—$CH_2$—; Y=4-carboxymethylphenyl;

X=S; $R^1$=t-butyl; $R^2$=t-butyl; $R^3$=H; $R^4$=H; Spacer=—$CH_2$—; Y=4-nitrophenyl;

X=S; $R^1$=t-butyl; $R^2$=t-butyl; $R^3$=H; $R^4$=H; Spacer=—$(CH_2)_2$—; Y=4-nitrophenyl;

X=S; $R^1$=t-butyl; $R^2$t-butyl; $R^3$=H; $R^4$=H; Spacer=—$CH_2$—; Y=2-carboxyethyl;

X=S; $R^1$=t-butyl; $R^2$-t-butyl; $R^3$=H; $R^4$=H; Spacer=—$CH_2$—; Y=3,5-di-t-butyl-4-carboxypropanoyloxy;

X=S; $R^1$=t-butyl; $R^2$=t-butyl; $R^3$=H; $R^4$=H; Spacer=—$CH_2$—; Y=4-carboxyphenyl;

X=S; $R^1$=t-butyl; $R^2$=t-butyl; $R^3$=H; $R^4$=H; Spacer=—$CH_2$—; Y=1-acetyloxy-1-methylethyl;

X=S; $R^1$=t-butyl; $R^2$=t-butyl; $R^3$=H; $R^4$=H; Spacer=—$CH_2$—; Y=3-nitrophenyl;

X=S; $R^1$=t-butyl; $R^2$=t-butyl; $R^3$=H; $R^4$=H; Spacer=—$CH_2$—; Y=2,4-dinitrophenyl;

X=S; $R^1$=t-butyl; $R^2$=t-butyl; $R^3$=H; $R^4$=H; Spacer=—$CH_2$—; Y=4-trifluoromethylphenyl;

X=S; $R^1$=t-butyl; $R^2$=t-butyl; $R^3$=H; $R^4$=H; Spacer=—$CH_2$—; Y=2-carboxyfuranyl;

X=S; $R^1$=t-butyl; $R^2$=t-butyl; $R^3$=H; $R^4$=H; Spacer=—$CH_2$—; Y=4-(N,N-dimethyl)sulfonamidophenyl;

X=SO; $R^1$=t-butyl; $R^2$=t-butyl; $R^3$=H; $R^4$=H; Spacer=—$CH_2$—; Y=4-nitrophenyl;

X=$SO_2$; $R^1$=t-butyl; $R^2$=t-butyl; $R^3$=H; $R^4$=H; Spacer=—$CH_2$—; Y=4-nitrophenyl;

X=S; $R^1$=t-butyl; $R^2$=t-butyl; $R^3$=H; $R^4$=H; Spacer=—$CH_2$—; Y=4-acetyloxyphenyl;

X=S; $R^1$=t-butyl; $R^2$=t-butyl; $R^3$=H; $R^4$=H; Spacer=—$CH_2$—; Y=4-methylphenyl;

X=S; $R^1$=t-butyl; $R^2$=t-butyl; $R^3$=H; $R^4$=H; Spacer=—$CH_2$—; Y=4-fluorophenyl;

X=S; $R^1$=t-butyl; $R^2$=t-butyl; $R^3$=H; $R^4$=H; Spacer=—$CH_2$—; Y=ethylsulfonic acid;

X=S; $R^1$=t-butyl; $R^2$=t-butyl; $R^3$=H; $R^4$=H; Spacer=—$CH_2$—; Y=2-dimethylaminomethyl;

X=S; $R^1$=t-butyl; $R^2$=t-butyl; $R^3$=H; $R^4$=H; Spacer=—$(CH_2)_3$—; Y=dimethylamino;

X=S; $R^1$=t-butyl; $R^2$=t-butyl; $R^3$=H; $R^4$=H; Spacer=—$(CH_2)_5$—; Y=acetyloxy;

X=S; $R^1$=t-butyl; $R^2$=t-butyl; $R^3$=H; $R^4$=H; Spacer=—$CH_2$—; Y=4-(2-hydroxy)ethylphenyl.

In another embodiment of the invention, there is provided a compound of formula (II) and a method for treating a disease mediated by the expression of VCAM-1 comprising administering an effective amount of a compound of formula (II):

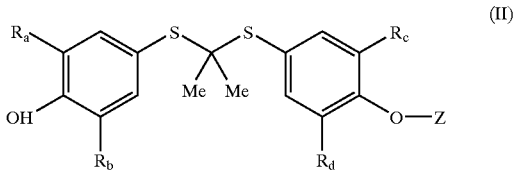

(II)

wherein $R_a$, $R_b$, $R_c$, and $R_d$ are independently hydrogen, straight chained, branched (for example, tert-butyl), or cyclic alkyl which may be substituted, aryl, substituted aryl, heteroaryl, substituted heteroaryl, alkaryl, substituted alkaryl, aralkyl or substituted aralkyl; substituents on the $R_a$, $R_b$, $R_c$ and $R_d$ groups are selected from the group consisting of hydrogen, halogen, alkyl, nitro, amino, haloalkyl, alkylamino, dialkylamino, acyl, and acyloxy;

Z is selected from the group consisting of hydrogen, alkyl, substituted alkyl, alkenyl, substituted alkenyl, alkynyl, substituted alkynyl, aryl, aralkyl, alkaryl, heteroaryl, heteroaralkyl, a carbohydrate group, —$(CH_2)$—$R_e$, —C(O)—$R_g$, and —C(O)—$(CH_2)_n$—$R_h$, wherein (a) when each of $R_a$, $R_b$, $R_c$, and $R_d$ are t-butyl, Z cannot be hydrogen and (b) when each of $R_a$, $R_b$, $R_c$, and $R_d$ are t-butyl, Z cannot be the residue of succinic acid;

$R_e$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, C(O)$NH_2$, C(O)NHR, C(O)$NR_2$;

$R_g$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl;

$R_h$ is selected from the group consisting of alkyl, substituted alkyl, alkenyl, substituted alkenyl, alkynyl, substituted alkynyl, alkoxy, substituted alkoxy, alkoxyalkyl, substituted alkoxyalkyl, $NH_2$, NHR, $NR_2$, mono- or polyhydroxy-substituted alkyl, aryl, substituted aryl, heteroaryl, substituted heteroaryl, acyloxy, substituted acyloxy, COOH, COOR, —CH(OH)$R_k$, hydroxy, O-phosphate, C(O)$NH_2$, C(O)NHR, C(O)$NR_2$ and pharmaceutically acceptable salts thereof;

or, in an alternative embodiment, $R_e$, $R_g$, and $R_h$ can independently be a substituent which improves the water solubility of the compound, including, but not limited to C(O)-spacer-$SO_3H$, wherein spacer is as defined above, C(O)-spacer-$SO_3M$, wherein M is a metal used to form a pharmaceutically acceptable salt, for example, sodium, C(O)-spacer-$PO_3H_2$, C(O)-spacer-$PO_3M_2$, C(O)-spacer-$PO_3HM$, C(O)-spacer-$PO_4H$, C(O)-spacer-$PO_4M$, $SO_3M$, —$PO_3H_2$, —$PO_3M_2$, —$PO_3HM$, cyclic phosphates, polyhydroxyalkyl, carbohydrate groups, C(O)-spacer-[O($C_{1-3}$ alkyl)$_p$]$_n$, wherein n is as defined above and p is 1, 2, or 3, —[O($C_{1-3}$ alkyl)$_p$]$_n$, carboxy lower alkyl, lower alkylcarbonyl lower alkyl, N,N-dialkyl amino lower alkyl, pyridyl lower alkyl, imidazolyl lower alkyl, morpholinyl lower alkyl, pyrrolidinyl lower alkyl, thiazolinyl lower alkyl, piperidinyl lower alkyl, morpholinyl lower hydroxyalkyl, N-pyrryl, piperazinyl lower alkyl, N-alkyl piperazinyl lower alkyl, triazolyl lower alkyl, tetrazolyl lower alkyl, tetrazolylamino lower alkyl, or thiazolyl lower alkyl.

Substitutents on the groups defined above are selected from the group consisting of alkyl, alkenyl, alkynyl, hydroxy, halo, nitro, amino, alkylamino, dialkylamino, carboxy, aryl, heteroaryl, COOR, CONH$_2$, CONHR, CONR$_2$, haloalkyl, alkoxyalkyl, mono- or polyhydroxyalkyl, CH$_2$—OR, CH$_2$—OH, OCOR, O-phosphate, SO$_2$—NH$_2$, SO$_2$—NHR, SO$_2$—NR$_2$.

A preferred embodiment of the present invention includes compounds of formula (II) wherein $R_a$, $R_b$, $R_c$, and $R_d$ are independently hydrogen or straight chained, branched, or cyclic $C_{1-10}$ alkyl; Z is selected from the group consisting of hydrogen, alkyl, substituted alkyl, alkenyl, substituted alkenyl, alkynyl, substituted alkynyl, a carbohydrate group, —$(CH_2)$—$R_e$, —C(O)—$R_g$, and —C(O)—$(CH_2)_n$—$R_h$, and pharmaceutically acceptable salts thereof Another preferred embodiment of the present invention includes compounds of formula (II) wherein $R_a$, $R_b$, $R_c$, and $R_d$ are independently hydrogen or straight chained, branched, or cyclic $C_{1-5}$ alkyl; Z is selected from the group consisting of hydrogen, alkyl, substituted alkyl, alkenyl, substituted alkenyl, alkynyl, substituted alkynyl, a carbohydrate group, —$(CH_2)$—$R_e$, —C(O)—$R_g$, and —C(O)—$(CH_2)_n$—$R_h$, and pharmaceutically acceptable salts thereof.

Another preferred embodiment of the present invention includes compounds of formula (II) wherein $R_a$, $R_b$, $R_c$, and $R_d$ are independently hydrogen or straight chained, branched, or cyclic $C_{1-5}$ alkyl; Z is selected from the group consisting of hydrogen, alkyl, substituted alkyl, alkenyl, substituted alkenyl, alkynyl, —$CH_2$-aryl substituted alkynyl, a carbohydrate group, —$CH_2$—$NR_2$, —$CH_2$-alkoxy, —$CH_2$—CHOH, —$CH_2$-substituted aryl, —$CH_2$-alkyl, —$CH_2$-substituted alkyl, —$CH_2$—OCO-alkyl, —$CH_2$—OCO-substituted alkyl, —$CH_2$—COOR, —$CH_2$—CH(OH)CH$_2$NHCH$_2$COOR, —$CH_2$—CH(OH)-substituted oxiranyl (wherein the substituent is selected from the group consisting of hydrogen, CH$_2$OH, CH$_2$CHOH-oxiranyl), —CO-aryl, —CO-substituted aryl, —CO-heteroaryl, —CO-substituted heteroaryl, —CO—(CH$_2$)$_n$—COOR, —CO—(CH$_2$)$_n$—OH, —CO—(CH$_2$)$_n$—O-phosphate, —CO—(CH$_2$)$_n$—CO—NR$_2$, —CO—(CH$_2$)$_n$-aryl, —CO—(CH$_2$)$_n$— substituted aryl, —CO—(CH$_2$)$_n$-heteroaryl, —CO—(CH$_2$)$_n$-substituted heteroaryl, —CO—(CH$_2$)$_n$—CONH (CH$_2$)COOR, —CO—(CH$_2$)$_n$—CON((CH$_2$)COOR)$_2$, monosaccharides, and cyclic monosaccharides, and pharmaceutically acceptable salts thereof.

Another preferred embodiment of the present invention includes compounds of formula (II) wherein R$_a$, R$_b$, R$_c$, and R$_d$ are independently hydrogen or straight chained, branched, or cyclic C$_{1-5}$ alkyl; Z is selected from the group consisting of hydrogen, alkyl, hydroxy alkyl, polyhydroxy alkyl, alkenyl, hydroxy alkenyl, acyl-substituted alkenyl, alkoxy alkyl, nitrophenylalkyl, aminophenylalkyl, alkylaminophenylalkyl, dialkylaminophenylalkyl, aminoalkyl, alkylaminoalkyl, dialkylaminoalkyl, carboxyalkyl, acyloxyalkyl, oxiranyl-substituted hydroxyalkyl, hydroxyalkyl-substituted oxiranylmethylene, oxiranyl-substituted hydroxyalkoxyalkyl oxiranylmethylene, oxiranylmethylene, carboxyalkylaminohydroxyalkyl, alkoxyhydroxyalkyl, glucopyranosyl, galactopyranosyl, N,N-diacylalkylaminohydroxyalkyl, carboxyalkylaminopolyhydroxyalkyl, (amino)(carboxy) alkylaminohydroxyalkyl, acyloxyhydroxyalkyl, polyhydroxyalkylaminohydroxyalkyl, CO-carboxyalkyl, CO-nitrofuranyl, CO-hydroxyalkyl, CO-polyhydroxyalkyl, CO-amidoalkyl, CO-aminoalkyl, CO-alkylaminoalkyl, CO-dialkylaminoalkyl, CO-acylalkyl, CO-alkoxycarbonylalkyl, CO-tetrazolylalkyl, CO-(acyl)(amino)alkylamino, dialkoxycarbonylalkylamidoalkyl, CO-hydroxyphenyloxyphosphonoxyalkyl, or pharmaceutically acceptable salts thereof Examples of the present invention include compounds of formula (II) wherein:

R$_a$=t-butyl, R$_b$=t-butyl, R$_c$=t-butyl, and R$_d$=t-butyl; Z=4-nitrophenyl;

R$_a$=t-butyl, R$_b$=t-butyl, R$_c$=t-butyl, and R$_d$=t-butyl; Z=CO—(CH$_2$)$_2$—COOH;

R$_a$=t-butyl, R$_b$=t-butyl, RF=t-butyl, and R$_d$=t-butyl; Z=CO—(5-nitrofuran-2-yl);

R$_a$=t-butyl, R$_b$=t-butyl, R=t-butyl, and R$_d$=t-butyl; Z=3-carboxypropyl;

R$_a$=1-methylethyl, R$_b$=t-butyl, R$_c$=methyl, and R$_d$=methyl; Z=4-aminobutyl;

R$_a$=t-butyl, R$_b$=t-butyl, R$_c$=t-butyl, and R$_d$=t-butyl; Z=4-aminobutyl;

R$_a$=t-butyl, R$_b$=t-butyl, R$_c$=t-butyl, and R$_d$=t-butyl; Z=3-hydroxypropanoyl;

R$_a$=t-butyl, R$_b$=t-butyl, R$_c$=t-butyl, and R$_d$ t-butyl; Z=t-butylcarbonyloxymethyl;

R$_a$=t-butyl, R$_b$=t-butyl, R$_c$=H, and R$_d$=H; Z=4-aminobutyl;

R$_a$=t-butyl, R$_b$=t-butyl, R$_c$=H, and R$_d$=H; Z=3-carboxypropyl;

R$_a$=t-butyl, R$_b$=t-butyl, R$_c$=t-butyl, and R$_d$=t-butyl; Z=carboxymethyl;

R$_a$=t-butyl, R$_b$=t-butyl, R$_c$=t-butyl, and R$_d$=t-butyl; Z=2—(CONH$_2$)ethanoyl;

R$_a$=t-butyl, R$_b$=t-butyl, R$_c$=t-butyl, and R$_d$=t-butyl; Z=CO-aminomethyl;

R$_a$=t-butyl, R$_b$=t-butyl, R$_c$=t-butyl, and R$_d$=t-butyl; Z=CO—(2-carboxyethyl);

R$_a$=t-butyl, R$_b$=t-butyl, R$_c$=t-butyl, and R$_d$=t-butyl; Z=CO—(2-methoxycarbonylethyl);

R$_a$=t-butyl, R$_b$=t-butyl, R$_c$=t-butyl, and R$_d$t-butyl; Z=CO-aminomethyl;

R$_a$=t-butyl, R$_b$=t-butyl, R$_c$=t-butyl, and R$_d$=t-butyl; Z=CO-3-carboxypropyl;

R$_a$=t-butyl, R$_b$=t-butyl, R$_c$=t-butyl, and R$_d$=t-butyl; Z=3-carboxypropyl;

R$_a$=t-butyl, R$_b$=t-butyl, R$_c$=t-butyl, and R$_d$=t-butyl; Z=CO-2-carboxyethyl;

R$_a$=t-butyl, R$_b$=t-butyl, R$_c$=t-butyl, and R$_d$=t-butyl; Z=CO-ammonium methyl (chloride)

R$_a$=t-butyl, R$_b$=t-butyl, R$_c$=t-butyl, and R$_d$=t-butyl; Z=2-hydroxy-2-oxiranyl-ethyl;

R$_a$=t-butyl, R$_b$=t-butyl, R$_c$=t-butyl, and R$_d$=t-butyl; Z=3-hydroxymethyloxirany-2-ylmethyl;

R$_a$=t-butyl, R$_b$=t-butyl, R$_c$=t-butyl, and R$_d$=t-butyl; Z=3-(2-hydroxy-2-oxiranyl)ethoxyoxiran-2-ylmethyl;

R$_a$=t-butyl, R$_b$=t-butyl, R$_c$=t-butyl, and R$_d$=t-butyl; Z=-oxiranylmethyl;

R$_a$=t-butyl, R$_b$=t-butyl, R$_c$=t-butyl, and R$_d$=t-butyl; Z=2-hydroxy-3-carboxymethylaminopropyl;

R$_a$=t-butyl, R$_b$=t-butyl, R$_c$=t-butyl, and R$_d$=t-butyl; Z=2,3,4-trihydroxybutyl;

R$_a$=t-butyl, R$_b$=t-butyl, R$_c$=t-butyl, and R$_d$=t-butyl; Z=2-hydroxy-3-ethoxypropyl;

R$_a$=t-butyl, R$_b$=t-butyl, R$_c$=t-butyl, and R$_d$=t-butyl; Z=2,3-dihydroxypropyl;

R$_a$=t-butyl, R$_b$=t-butyl, R$_c$=t-butyl, and R$_d$=t-butyl; Z=ethyl;

R$_a$=t-butyl, R$_b$=t-butyl, R$_c$=t-butyl, and R$_d$=t-butyl; Z=2-ethoxycarbonylethenyl;

R$_a$=t-butyl, R$_b$=t-butyl, R$_c$=t-butyl, and R$_d$=t-butyl; Z=4-N,N-dimethylaminophenethyl;

R$_a$=t-butyl, R$_b$=t-butyl, R$_c$=t-butyl, and R$_d$=t-butyl; Z=CO-2-carboxyethyl;

R$_a$=t-butyl, R$_b$=t-butyl, R$_c$=t-butyl, and R$_d$=t-butyl; Z=CO-2-carboxyethyl (L-arginine ester)

R$_a$=t-butyl, R$_b$=t-butyl, R$_c$=t-butyl, and R$_d$=t-butyl; Z=3-methoxycarbonylpropyl;

R$_a$=t-butyl, R$_b$=t-butyl, R$_c$=t-butyl, and R$_d$=t-butyl; Z=2-carboxyethenyl;

R$_a$=t-butyl, R$_b$=t-butyl, R$_c$=t-butyl, and R$_d$=t-butyl; Z=galactopyranosylmethyl;

R$_a$=t-butyl, R$_b$=t-butyl, R$_c$=t-butyl, and R$_d$=t-butyl; Z=3-(N-N-diethylamino)propyl;

R$_a$=t-butyl, R$_b$=t-butyl, R$_c$=t-butyl, and R$_d$=t-butyl; Z=2-ethoxycarbonylethenyl;

R$_a$=t-butyl, R$_b$=t-butyl, R$_c$=t-butyl, and R$_d$=t-butyl; Z=carboxymethylaminocarbonylmethyl;

R$_a$=t-butyl, R$_b$=t-butyl, R$_c$=t-butyl, and R$_d$=t-butyl; Z=1,3-dicarboxypropylaminocarbonylmethyl;

R$_a$=t-butyl, R$_b$=t-butyl, R$_c$=t-butyl, and R$_d$=t-butyl; Z=2-hydroxy-3-(1,3-diethoxycarbonyl)propylaminopropyl;

R$_a$=t-butyl, R$_b$=t-butyl, R$_c$=t-butyl, and R$_d$=t-butyl; Z=2,3-dihydroxy4-carboxymethylaminobutyl;

R$_a$=t-butyl, R$_b$=t-butyl, R$_c$=t-butyl, and R$_d$=t-butyl; Z=2-hydroxy-3-(5-amino-5-carboxy)propylaminopropyl;

R$_a$=t-butyl, R$_b$=t-butyl, R$_c$=t-butyl, and R$_d$=t-butyl; Z=4-ethylcarbonyloxybutyl;

R$_a$=t-butyl, R$_b$=t-butyl, R$_c$=t-butyl, and R$_d$=t-butyl; Z=4-hydroxybutyl;

R$_a$=t-butyl, R$_b$=t-butyl, R$_c$=t-butyl, and R$_d$=t-butyl; Z=glucopyranosylmethyl;

R$_a$=t-butyl, R$_b$=t-butyl, R$_c$=t-butyl, and R$_d$=t-butyl; Z=CO-3-tetrazolylpropyl;

R$_a$=t-butyl, R$_b$=t-butyl, R$_c$=t-butyl, and R$_d$=t-butyl; Z=3-hydroxypropenyl;

R$_a$=t-butyl, R$_b$=t-butyl, R$_c$=t-butyl, and R$_d$=t-butyl; Z=CH$_2$CONH—(CH$_2$) CH(NH$_2$)COOH;

R$_a$=t-butyl, R$_b$=t-butyl, R$_c$=t-butyl, and R$_d$=t-butyl; Z=CH$_2$CONHCH(COOet)CH$_2$CH$_2$(COOet);

R$_a$=t-butyl, R$_b$=t-butyl, R$_c$=t-butyl, and R$_d$=t-butyl; Z=glucopyranosylmethyl;

R$_a$=t-butyl, R$_b$=t-butyl, R$_c$=t-butyl, and R$_d$=t-butyl; Z=2,3,4,5,6-pentahydroxyhexane;

$R_a$=t-butyl, $R_b$=t-butyl, $R_c$=t-butyl, and $R_d$=t-butyl; Z=CO-3-(2-hydroxyphenyloxyphosphoxy)propyl;

$R_a$=t-butyl, $R_b$=t-butyl, $R_c$=t-butyl, and $R_d$=t-butyl; Z=CO-2,2-dimethyl-3-hydroxypropyl;

$R_a$=t-butyl, $R_b$=t-butyl, $R_c$=t-butyl, and $R_d$=t-butyl; Z=2-hydroxy-3-acetoxypropyl;

$R_a$=t-butyl, $R_b$=t-butyl, $R_c$=t-butyl, and $R_d$=t-butyl; Z=2-acetoxy-3-hydroxypropyl;

$R_a$=t-butyl, $R_b$=t-butyl, $R_c$=t-butyl, and $R_d$=t-butyl; Z=CH$_2$CH(OH)CH$_2$NH(2,3,4,5,6-pentahydroxyhexane.

The compounds of formula (I) can be prepared by utilizing known procedures and techniques, or routine modifications thereof. A general synthetic scheme for preparing compounds of formula (I) is set forth in Scheme A, wherein all substituents, unless otherwise indicated, are previously defined.

Scheme A

The synthesis of the starting thiol, 4-mercapto-2,6-di-t-butylphenol, is described in the literature (U.S. Pat. No. 3,129,262 to Laufer, incorporated herein by reference in its entirety). The starting alkyl halides are commercially available or made from commercially available starting materials by methods known to one of ordinary skill in the art.

A quantity of the 4-mercapto-2,6-di-t-butylphenol is dissolved in ethanol to make a 0.5 M solution and treated with 1.2 equivalents of sodium hydroxide (5 N aqueous solution). After 5 minutes 1.2 equivalents of alkyl halide is added and the reaction mixture stirred at room temperature for 24 hours. The reaction is quenched with 1 N HCl to pH 7, diluted with water, extracted with ether and dried over magnesium sulfate. The product is purified by silica gel chromatography.

Starting materials for use in the general synthetic procedure outlined in Scheme A are readily available to one of ordinary skill in the art. For example, certain phenol starting materials for various compounds of formula (I), such as 2,6-di-tertiarybutyl-4-mercaptophenol, are described in U.S. Pat. No. 3,576,883, U.S. Pat. No. 3,952,064, U.S. Pat. No. 3,479,407 and in Japanese Patent Application 73–28425.

In general, a phenol of structure (I) can be prepared by dissolving the appropriate 2,6-dialkyl-4-thiophenol (or suitably protected derivatives) in alcohol, preferably in ethanol, followed by addition of a halogenated aryl compound.

The starting material, a 2,6-dialkyl-substituted thiophenol, may be protected by any of the many protecting groups known to one of ordinary skill in the art. Examples of suitable phenol protecting groups are ethers, such as methoxymethyl, 2-methoxyethoxymethyl, tetrahydropyranyl, t-butyl and benzyl; silyl ethers, such as trimethylsilyl and 1-butyldimethylsilyl; esters, such as acetate and benzoate; carbonates, such as methylcarbonate and benzyl carbonate; as well as sulfonates, such as methane sulfonate and toluene sulfonate.

The following examples present typical syntheses as described in Scheme A. These examples are understood to be illustrative only and are not intended to limit the scope of the present invention in any way. As used herein, the following terms have the indicated meanings "g" refers to grams; "mmol" refers to millimoles; "mL" refers to milliliters; "bp" refers to boiling point; "° C." refers to degrees Celsius; "mm Hg" refers to millimeters of mercury; "mp" refers to melting point; "mg" refers to milligrams; "$\mu$M" refers to micromolar; "$\mu$g" refers to micrograms.

EXAMPLE 1

2,6-di-tert-butyl-4-thio(4'(methyl)phenylacetic acid))phenol

Reaction Description 2,6-di-t-butyl-4-thiophenol (238 mg, 1 mmol) was dissolved in ethanol (0.7 mL) and cooled to 0° C. 5 N NaOH (0.6 mL, 3 mmol) was added followed by addition of 4-(bromomethyl)phenyl acetic acid (229 mg, 1 mmol). The reaction was warmed to room temperature and after 0.5 h the reaction was complete. The reaction was quenched with 1 N HCl (3.5 mL) and diluted with ether (25 mL). The ether layer was separated and washed with water (1×5 mL) and brine (1×5 mL), dried over MgSO$_4$, filtered and concentrated. Chromatography over silica gel and eluting with 50:50 ether/hexane provided 170 mg of (2,6-di-tert-butyl-4-thio(4' (methyl)phenylacetic acid))phenol). $^1$H NMR (CDCl$_3$, 400 MHZ): δ7.24 (s, 2 H), 7.17 (d, J=8.4 Hz, 2 H), 7.11 (d, J=8.4 Hz, 2 H), 5.20 (s, 1H), 3.91 (s, 2 H), 3.59 (s, 2 H), 1.33 (s, 18 H).

EXAMPLE 2

2,6-di-tert-butyl4-thio(4'-nitrobenzyl)phenol

Reaction Description

A solution of 0.28 mmol (68 mg) of 2,6-di-tert-butyl-4-thiophenol in 0.5 mL of EtOH (denatured) was stirred and treated with 0.3 mmol (0.06 mL) of NaOH (5 N in de-ionized water) at 0° C. After stirring for 5 min., 0.29 mmol (62 mg) of 4-nitrobenzyl bromide was added to give an orange solution. The progress of the reaction was monitored by TLC (1:1 hexanes-hexanes-CH$_2$Cl$_2$; visualized by UV and PMA/char). The bromide was consumed over a 2 h period. The mixture was then quenched with sat. NaCl-EtOAc. The aqueous layer was back-extracted with 2×2 mL of EtOAc; the combined organic layers were dried over anhydrous MgSO$_4$. The drying agent was removed by filtration; solvent was removed by rotary evaporation to give a crude oil. The oil was purified by preparative thin-layer chromatography (pTLC) using 2×500$\mu$ plates and 1:1 hexanes-CH$_2$Cl$_2$ as eluant. The desired product (2,6-di-tert-butyl-4-thio(4'-nitrobenzyl)phenol) was obtained in 86% yield (90 mg). $^1$H NMR (CDCl$_3$, 400 MHZ): δ8.10 (d, J=8.8 Hz, 2 H), 7.25 (d, J=8.8 Hz, 2 H), 7.04 (s, 2 H), 5.28 (s, 1H), 3.98 (s, 2 H), 1.34 (H).

EXAMPLE 3

2,6-di-tert-butyl-4-thio(4'-nitrophenethyl)phenol

Reaction Description 0.48 mmol (115 mg) of 2,6-di-tert-butyl-4-thiophenol was taken up and stirred in 2 mL of dry THF. The mixture was treated with 0.67 mmol (27 mg) of sodium hydride (60% suspension in mineral oil) to give a clear, dark yellow solution. 4-Nitrophenethyl iodide (0.49 mmol; 135 mg) was added to give a dark brown mixture which was stirred overnight. The progress of the reaction was monitored by TLC (3×10:1 hexanes-CH$_2$Cl$_2$; visualized by UV and PMA/char), and the reaction was quenched (with sat. NaCl-EtOAc) when only traces of the starting iodide remained. The aqueous layer was back-extracted with 2×5 mL of EtOAc; the combined organic layers were dried over anhydrous MgSO$_4$. Filtration to remove the drying agent followed by solvent removal by rotary evaporation gave a dark brown oil. Purification of the crude material using radial chromatography (10:1 hexanes-CH$_2$Cl$_2$; 4 mm plate) gave 93 mg (50% yield) of 2,6-di-tert-butyl-4-thio(4'-nitrophenethyl)phenol. $^1$H NMR (CDCl$_3$, 400 MHZ): δ8.15 (d, J=8.8 Hz, 2 H), 7.34 (d, J=8.4 Hz, 2 H), 7.24 (s, 2 H), 5.26 (s, 1H), 3.11 (t, J=7.2 Hz, 2 H), 3.09 (t, J=7.6 Hz, 2 H), 1.43 (s, 18 H).

EXAMPLE 4

2,6-di-tert-butyl-4-thio(3'-nitrobenzyl)phenol

Reaction Description

3-Nitrobenzyl chloride (0.42 mmol; 72 mg) and 2,6di-tert-butylthiophenol (0.42 mmol; 100 mg) were dissolved in 0.7 mL of EtOH and treated with 92 μL of NaOH (5 N solution). The reaction mixture was stirred for 19.5 h then quenched with sat. NaCl and extracted with EtOAc. The aqueous layer was back-extracted with EtOAc (2×10 mL). The organic portions were collected, dried over $Na_2SO_4$, and concentrated in to a yellow oil. The crude material was placed under vacuum for 2 h. Purification was performed via radial chromatography using 2 mm ($SiO_2$) plates and 4:1 hexanes-EtOAc. 2,6-di-tert-butyl-4-thio(3'-nitrobenzyl) phenol was obtained as a yellow oil (108 mg; 69% yield). 8.07 (app d, J=7.6 Hz, 1 H), 7.87 (s, 1 H), 7.48 (AB d, J=7.6 Hz, 1 H), 7.42 (AB m, J=7.6, 8.0 Hz, 1 H), 7.05 (s, 2 H), 5.27 (s, 1 H), 3.99 (s, 2 H), 1.34 (s, 18 H).

EXAMPLE 5

2,6-di-tert-butyl4-thio(2',4'-dinitrobenzyl)phenol

Reaction Description 2,4-dinitrobenzyl chloride (0.42 mmol; 91 mg) and 2,6-di-tert-butylthiophenol (0.42 mmol; 100 mg) were dissolved in 0.7 mL of EtOH and treated with 92 μL of NaOH (5 N solution). The reaction mixture was stirred for 19.5 h then quenched with sat. NaCl and extracted with EtOAc (25 mL). The aqueous layer was back-extracted with EtOAc (2×10 mL). The organic layers were collected, dried over $Na_2SO_4$, and concentrated to a brown oil. Purification of the oil via radial chromatography using 2 mm plate ($SiO_2$) and 4:1 hexanes-EtOAc as eluant gave 2,6-di-tert-butyl4-thio(2',4'-dinitrobenzyl)phenol as a yellow oil (37 mg; 21% yield). $^1$H NMR ($CDCl_3$, 400 MHZ): δ8.74 (app d, J=2.4 Hz, 1 H), 8.24 (dd, J=8.8, 2.4 Hz, 1 H), 7.29 (d, J=8.8 Hz, 1 H), 6.98 (s, 2 H), 5.35 (s, 1 H), 4.36 (s, 2 H), 1.34 (s, 18 H).

EXAMPLE 6

(2,6-di-tert-butyl4-thio(4'-(trifluoromethyl)benzyl) phenol

Reaction Description 4-(Trifluoromethyl)benzyl bromide (0.42 mmol; 100 mg) and 2,6di-tert-butylthiophenol (0.42 mmol; 100 mg) were dissolved in 0.7 mL of EtOH and treated with 92 μL of NaOH (5 N solution). The reaction mixture turned brown within 30 min., and precipitation was observed. The mixture was stirred for 22 h then quenched with sat. NaCl and EtOAc. The aqueous layers were back-extracted with 2×10 mL of EtOAc. The combined organic layers were dried over $Na_2SO_4$ then concentrated to give a brownish orange solid. Purification of the solid via radial chromatography using 4 mm plate ($SiO_2$) and 4:1 hexanes-EtOAc as eluant gave (2,6-di-tert-butyl4-thio(4'-(trifluoromethyl)benzyl)phenol as a yellow solid (140 mg; 84% yield). $^1$H NMR ($CDCl_3$, 400 MHZ): δ7.48 (AB d, J=8.0 Hz, 2 H), 7.20 (AB d, J 8.0 Hz, 2 H), 7.01 (s, 2 H), 5.24 (s, 1 H), 3.93 (s, 2 H), 1.33 (s, 18 H).

EXAMPLE 7

2,6-di-tert-butyn4-thio((2'-furancarboxylic acid)-5-methyl)phenol

Reaction Description 2,6-di-tert-butyl-4-thiophenol (0.49 mmol; 116 mg) was dissolved in dry ThF (2 mL), stirred, and treated with sodium hydride (0.58 mmol; 23 mg; 60% dispersion in mineral oil). The resulting yellow solution was treated with methyl 5-(chloromethyl)-2-furoate (0.54 mmol; 95 mg). The brown mixture was stirred for 22 h then quenched with brine. Extraction with EtOAc (3×3 mL), combination of the organic layers and drying over $MgSO_4$ then solvent removal by rotary evaporation gave a crude oil. The crude product was eluted on 2×500μ preparative thin-layer chromatography plates ($SiO_2$; 1:1 hexanes-$CH_2Cl_2$ as eluant) to give the expected intermediate (132 mg; 72% yield). The intermediate (0.35 mmol; 132 mg) was taken up in 4:1:1 MeOH-THF-$H_2O$ (3 mL), stirred, and treated with LiOH monohydrate (1.2 mmol; 50 mg). The mixture was stirred at room temperature for 18 h then solvent was removed to give 2,6-di-tert-butyl-4-thio((2'-furancarboxylic acid)-5-methyl) phenol (94 mg; 74% yield) as a tan solid. $^1$H NMR ($CDCl_3$, 400 MHZ): δ7.21 (d, J=3.2 Hz, 1 H), 7.19 (s, 2 H), 6.17 (d, J=3.2 Hz, 1 H), 5.30 (br s, 1 H), 4.00 (s, 2 H), 1.40 (s, 18 H).

EXAMPLE 8

2,6-di-tert-butyl-4-thio(4'-methyl-N,N-dimethylbenzenesulfonamide)phenol

Reaction Description 2,6 di-t-butyl-4-thiophenol (180 mg, 0.755 mmol) was dissolved in ethanol (1.5 mL) and then treated with 5 N NaOH (0.15 mL, 0.75 mmol). After 5 min, 4-(N,N-dimethylsulfonamide)benzyl bromide (210 mg, 0.755) in ethanol (1.5 mL) was added to the reaction. The resulting mixture was stirred at room temperature for 3 h. The reaction was quenched with 1N HCl to pH 7, diluted with water (3 mL), extracted with ether (10 mL), separated and dried over $MgSO_4$. The crude reaction mixture was purified by column chromatography over silica gel and eluting with 30:70 ether/hexane followed by 40:60 ether/hexane. The appropriate fractions were collected to give 160 mg of the desired product. $^1$H NMR ($CDCl_3$, 400 MHZ): δ7.67 (d, J=8.4 Hz, 2 H), 7.32 (d, J=8.4 Hz, 2 H), 7.08 (s, 2 H), 5.27 (s, 1 H), 2.69 (s, 6 H), 1.36 (s, 18 H).

EXAMPLE 9

2,6-di-tert-butyl-4-sulfinyl(4'-nitrobenzyl)phenol

Reaction Description 2,6-di-tert-butyl4-thio(3'-nitrobenzyl)phenol (157 mg, 0.42 mmol) was taken up in methylene chloride (4.2 mL) and mCPBA was added. After 15 min the reaction was diluted with ether (15 mL) and washed with saturated aqueous sodium bicarbonate (2×5 mL), followed by water (1×5 mL) and brine (1×5 mL). The ether layer was dried over $MgSO_4$, filtered, and concentrated. The resulting oil was chromatographed by radial silica gel chrolmatography eluting with a concentration gradient of 30:70 ether/hexane to 80:20 ether/hexane. The appropriate fractions were collected (Rf=0.2, 80:20 ether/hexane) and concentrated to give 50 mg of 2,6-di-tert-butyl4-thio(3'-nitrobenzyl)phenol sulfoxide. $^1$H NMR ($CDCl_3$, 400 MHz): δ8.11 (d, J=8.8 Hz, 2 H), 7.07 (br s, 4 H), 5.57 (br s, 1 H), 4.13 (d, J=12.4 Hz, 2 H), 4.01 (d, J=12.4 Hz, 2 H), 1.36 (s, 18 H).

EXAMPLE 10

2,6-di-tert-butyl4-(sulfonyl-(4'-nitrobenzyl))phenol

Reaction Description 2,6-di-tert-butyl-4-thio(3'-nitrobenzyl)phenol (157 mg, 0.42 mmol) was taken up in methylene chloride (4.2 mL)

and mCPBA was added. After 15 minutes, the reaction was diluted with ether (15 mL) and washed with saturated aqueous sodium bicarbonate (2×5 mL), followed by water (1×5 mL) and brine (1×5 mL). The ether layer was dried over MgSO$_4$, filtered, and concentrated. The resulting oil was chromatographed by radial silica gel chromatography eluting with a concentration gradient of 30:70 ether/hexane to 80:20 ether/hexane. The appropriate fractions were collected (Rf=0.5, 80:20 ether/hexane) and concentrated to give 72 mg of product. 8.16 (d, J=8.4 Hz, 2 H), 7.38 (s, 2 H), 7.29 (d, J=8.4 Hz, 2 H), 5,84 (s, 1 H), 4.35 (s, 18 H).

EXAMPLE 11

2,6-di-tert-butyl-4-thio(4'-acetoxybenzyl)phenol

Reaction Description

A solution of 2,6-di-tert-butylthiophenol (0.46 mmol; 110 mg) in dry DMF (4.2 mL) was treated with sodium hydride (0.63 mmol; 25 mg; 60% dispersion in mineral oil) and allowed to stir at room temperature for 15 min. The orange mixture was treated with 4-(chloromethyl)phenyl acetate (0.42 mmol; 77 mg) resulting in a rust-brown color. The mixture was stirred for 6.5 h then diluted with EtOAc (20 mL) and washed with de-ionized H$_2$O (25 mL). The organic layer was washed with sat. NaCl then concentrated to give a crude oil. Purification by column chromatography (SiO$_2$) using 4:1 hexanes-EtOAc gave 2,6di-tert-butyl-4-thio(4'-acetoxybenzyl)phenol as an oil (38 mg; 21% yield). $^1$H NMR (CDCl$_3$, 400 MHZ): δ7.17 (AB d, J=8.8 Hz, 2 H), 7.10 (s, 2 H), 6.97 (AB d, J=8.8 Hz, 2 H), 5.23 (s, 1 H), 3.94 (s, 2 H), 2.29 (s, 3 H), 1.37 (s, 18 H).

EXAMPLE 12

2,6-di-tert-butyl-4-thio(4'-methylbenzyl)phenol

Reaction Description

A solution of 0.64 mmol (153 mg) of 2,6-di-tert-butylthiophenol in 1.6 mL of dry THF was stirred and treated with 0.85 mmol (34 mg) of sodium hydride (60% suspension in mineral oil) to give a dark orange-brown mixture. 4-Methylbenzyl bromide (0.66 mmol; 122 mg) was added. The mixture was stirred overnight. The progress of the reaction was monitored by TLC (hexanes; visualization by UV and PMA/char). After approx. 24 h, the appearance of product was detected by TLC (PMA staining gave a blue-black spot). The reaction was quenched using sat. NaCl-EtOAc. The aqueous layer was back-extracted with 2×5 mL of EtOAc; the combined organic layers were dried over anhydrous MgSO$_4$ then filtered to remove the drying agent. Removal of solvent by rotary evaporation gave a crude oil that was eluted twice on 2×500μ preparative TLC (SiO$_2$) plates using hexanes. The product (2,6-di-tert-butyl-4-thio(4'-methylbenzyl)phenol) was isolated as a yellow solid in 32% yield (70 mg). $^1$H NMR (CDCl$_3$, 400 MHZ): δ7.10 (s, 2 H), 7.07 (s, 4 H), 5.22 (s, 1 H), 3.94 (s, 2 H), 2.33 (s, 3 H), 1.38 (s, 18 H).

EXAMPLE 13

2,6-di-tert-butyl-4-thio(4'-fluorobenzyl)phenol

Reaction Description

A solution of 2,6-di-tert-butylthiophenol (0.46 mmol; 110 mg) in 0.7 mL of EtOH was treated with 92 μL of NaOH (5 N solution). The brown mixture was then treated with 4-fluorobenzyl bromide (0.42 mmol; 52 μL) then stirred for 24 h. The mixture was quenched with sat. NaCl and extracted with EtOAc (20 mL). The aqueous layer was back extracted with 2×10 mL of EtOAc. The combined organic layers were dried over Na$_2$SO$_4$ then concentrated to give the crude product. Purification by MPLC (SiO$_2$) using a solvent gradient of 100% hexanes to 19:1 hexanes-EtOAc gave 119 mg of product that was contaminated with starting thiol. Further purification via preparative thin-layer chromatography (pTLC) using 2×500μ SiO$_2$ plates and 19:1 hexanes-EtOAc as eluant gave 2,6-di-tert-butyl-4-thio(4'-fluorobenzyl)phenol (34 mg; 34% yield). $^1$H NMR (CDCl$_3$, 400 MHZ): δ7.09 (AB t, J=8.8 Hz, 2 H), 7.07 (s, 2 H), 6.92 (AB t, J=8.8 Hz, 2 H), 5.23 (s, 1 H), 3.91 (s, 2 H), 1.36 (s, 18 H).

EXAMPLE 14

2,6-di-tert-butyl-4-thio(3'-propanesulfonic acid) phenol

Reaction Description 2,6-di-tert-butylthiophenol (0.84 mmol; 200 mg) and 3-bromopropanesulfonic acid (0.92 mmol; 207 mg) were taken up in EtOH and treated with 0.18 mL of NaOH (5 N solution). The reaction was allowed to stir for 90 h then quenched with 1 mL of 0.3 N HCl and extracted with 10 mL of EtOAc. The organic layer was dried over MgSO$_4$, concentrated on SiO$_2$ (rotary evaporation), and purified via MPLC using the following solvent gradient: 100% CH$_2$Cl$_2$ followed by 4:1 CH$_2$Cl$_2$—MeOH (100 mL) followed by 4:1 CH$_2$Cl$_2$—MeOH containing 0.4 mL AcOH. 2,6-di-tert-butyl-4-thio(3'-propanesulfonic acid)phenol was obtained as an off-white solid (126 mg; 42% yield). $^1$H NMR ((CD$_3$)$_2$SO, 400 MHz): δ7.06 (s, 2 H), 2.88 (app t, J=7.2, 7.6 Hz, 2 H), 2.52–2.48 (m, 2 H), 1.88 (s, 2 H), 1.80 (pent, J=7.2, 7.6 Hz, 2 H), 1.35 (s, 18 H). LRMS: Neg. Ion ES 359 (M-H).

EXAMPLE 15

2,6-di-tert-butyl-4-thio(5'-methyl-2'-((dimethylamino)methyl)furan)phenol

Reaction Description

A solution of 2,6-di-tert-butyl-4-thiophenol disulfide (0.24 mmol; 112 mg) and 2-((dimethylamino)methyl)-5-(hydroxymethyl)furan (0.13 mmol; 25 mg) in 2.4 mL of dry THF was treated with 0.13 mmol (32 mg) of tributylphosphine. The reaction was stirred for over 60 h then solvent was removed by rotary evaporation to give a light yellow oil. The crude oil was purified by radial chromatography (2 mm SiO$_2$ plate; 95:5 CH$_2$Cl$_2$—MeOH as eluant) to give 7.3 mg (7.5% yield) of the title compound as a light yellow amorphous solid. $^1$H NMR (CDCl$_3$, 400 MHZ): δ7.17 (s, 2 H), 6.22 (d, J=3.2 Hz, 1 H), 5.97 (d, J=3.2 Hz, 1 H), 5.22 (br s H), 3.95 (s, 2 H), 3.72 (s, 2 H), 2.37 (s, 6 H), 1.40 (s, 18 H).

EXAMPLE 16

2,6-di-tert-butyl-4-thio(3'-(dimethylamino)propyl)) phenol

Reaction Description

A solution of 0.5 mmol (119 mg) of 2,6-di-tert-butylthiophenol in 1.5 mL of dry DMF was stirred and treated with 0.55 mmol (22 mg) of sodium hydride (60% dispersion in mineral oil). 3-(Dimethylamino)propyl chloride hydrochloride (0.5 mmol; 79 mg) was added, and the brown mixture was stirred for 2 days. TLC (1:1 hexanes-$CH_2Cl_2$; visualization by UV and PMA/char) showed mostly starting materials. The mixture was treated with 0.5 mmol NaOH (5 N solution) then stirred overnight. TLC analysis showed the appearance of a new UV-active material (low Rf; streaks). The reaction was quenched with sat. NaCl-EtOAc. The aqueous layer was back-extracted with EtOAc, and the combined organic layers were dried over anhydrous $MgSO_4$. Drying agent was removed by filtration. Solvent removal by rotary evaporation gave a brown oil. Purification by preparative thin-layer chromatography (pTLC) using 2×500μ plates ($SiO_2$) and EtOH as eluant provided 2,6-di-tert-butyl-4-thio(3'-(dimethylamino) propyl))phenol as a pale yellow solid (61 mg; 37% yield) $^1H$ NMR ($CDCl_3$, 400 MHZ): δ7.24 (s, 2 H), 5.20 (s, 1 H), 2.85 (t, J=7.6, 7.2 Hz, 2 H), 2.37 (t, J=7.6, 7.2 Hz, 2 H), 2.20 (s, 6 H), 1.77 (q, J=7.6, 7.0 Hz, 2 H), 1.42 (s, 18 H).

EXAMPLE 17

2,6-di-tert-butylthio((1'-(acetoxy))pentyl)phenol

Reaction Description 2,6-di-tert-butyl-4-thiophenol (0.84 mmol; 200 mg) was dissolved in 7.6 mL of DMF and treated with 1.1 mmol (46 mg) of NaH (60% dispersion in mineral oil) to give an orange mixture. After 15 min., 0.76 mmol (0.12 mL) of 5-chloropentyl acetate was added. The mixture was stirred for 25 h then diluted with 20 mL of EtOAc and washed with $H_2O$ (25 mL). The organic layer was washed with brine then concentrated by rotary evaporation. The crude material was purified by radial chromatography (2 mm $SiO_2$ plate; 85:15 hexanes-EtOAc as eluant) to give 2,6-di-tert-butyl-4-thio ((1'-(acetoxy))pentyl)phenol (93 mg; 30% yield) as a light yellow, amorphous solid. $^1H$ NMR ($CDCl_3$, 400 MHZ): δ7.23 (s, 2 H), 5.20 (s, 1 H), 4.05 (app t, J=6.4, 7.2 Hz, 2 H), 2.83 (app t, J=6.8, 7.2 Hz, 2 H), 2.04 (s, 3 H), 1.66–1.58 (br m, 4 H), 1.50–1.42 (br m, 2 H), 1.43 (s, 18 H).

EXAMPLE 18

2,6-di-tert-butyl-1-methoxy-4-thio(4'-trifluoromethyl)benzyl)benzene

Reaction Description (2,6-di-tert-butyl-4-thio(4'-(trifluoromethyl)benzyl) phenol (60 mg, 0.15 mmol) was taken up in dimethylformamide (0.75 mL), 60% sodium hydride in mineral oil (9 mg, 0.225 mmol) was added followed by methyl iodide (0.014 mL, 0.225 mmol). After 0.5 h the reaction was quenched with 1 N HCl (1 mL) and diluted with ether (10 mL). The ether layer was washed with water (1×3 mL) and brine (1×3 mL), dried over $MgSO_4$, filtered, and concentrated. The resulting oil was purified by radial silica gel chromatography eluting with hexane followed by 1:99 ether/ hexane to give 20 mg of the product. $^1H$ NMR ($CDCl_3$, 400 MHz): δ7.48 (d, J=8.0 Hz, 2 H), 7.20 (d, J=8.0 Hz, 2 H), 7.01 (s, 2 H), 3.93 (s, 2 H), 3.60 (s, 3 H), 1.33 (s, 18 H).

EXAMPLE 19

2,6-di-tert-butyl-4-thio(4'-(methyl)phenylethyl alcohol))phenol

Reaction Description

The compound of Example 1 (300 mg, 0.86 mmol) was dissolved in THF (17.2 mL) and cooled to −78° C. Borane-dimethyl sulfide (2M in THF, 1.72 mL, 1.72 mmol) was added and stirred overnight under nitrogen while cooling bath was allowed to warm to room temperature. The reaction was cooled to 0° C., and concentrated HCl was added (0.5 mL) and stirred overnight. The solvents in the reaction mixture were removed in vaccuo and the residue dissolved in ethyl acetate (25 mL), washed with brine (1×5 mL), IN NaOH (1×5 mL), and brine (1×5 mL). The ethyl acetate layer was dried over $MgSO_4$, filtered, concentrated and chromatographed over silica gel with 40:60 ether/hexanes to yield 198 mg of product. $^1H$ NMR ($CDCl_3$, 400 MHz): δ7.12 (s, 4 H), 7.09 (s, 2 H), 5.21 (s, 1 H), 3.94 (s, 2 H), 3.84 (br s, 2 H), 2.84 (t, J=6.8 Hz, 2 H), 1.36 (s, 18 H).

The compounds of formula (II) wherein Z forms an ether group can be prepared by known procedures and techniques, or routine modifications thereof. A general synthetic scheme for preparing compounds of formula (II) wherein Z forms an ether group is set forth in Scheme B, wherein all substituents, unless otherwise indicated, are previously defined.

Scheme B

A quantity of probucol (commercially available from Sigma Chemicals) in a 0.1 M solution of tetrahydrofuran is treated with 2 equivalents of sodium hydride and stirred at room temperature for 30 minutes. To the reaction mixture is added 3 equivalents of a primary alkyl bromide or iodide and the reaction stirred at room temperature for 16 hours. The reaction is quenched with 1 N aqueous HCl and diluted with ethyl acetate. The aqueous layer is removed and the ehtyl acetate layer is washed with water and then with an aqueous saturated sodium chloride solution. The ethyl acetate solution is dried over magnesium sulfate, gravity or vacuum filtered, and then concentrated. The product is purified by silica gel chromatography.

An alternative method for the preparation of compounds of formula (II) wherein Z forms an ether group is the treatment of probucol with a primary alcohol according to the method of Mitsunobu (*Synthesis*, 1981, 1).

A second alternative method for the preparation of compounds of formula (II) wherein Z forms an ether group is the treatment of probucol with a primary alkyl bromide or iodide in acetonitrile in the presence of potassium fluoride absorbed on alumina according to the method of Ando et al. (*Bull. Chem. Soc. Jpn.*, 55, 1982, 2504–2507).

The compounds of formula (II) wherein Z forms an ester group can be prepared by utilizing procedures and techniques well known and appreciated by one of ordinary skill in the art. A general synthetic scheme for preparing compounds of formula (II) wherein Z forms an ester group is set forth in Scheme C, wherein all substituents, unless otherwise indicated, are previously defined.

Scheme C

A quantity of probucol in a 0.1 M solution of tetrahydrofuran is treated with 2 equivalents of sodium hydride and stirred at room temperature for 30 minutes. To the reaction mixture is added 3 equivalents of an acid chloride or acid anhydride and the reaction stirred at room temperature for 16 hours. The reaction is quenched with 1 N aqueous HCl and diluted with ethyl acetate. The aqueous layer is removed and the ethyl acetate layer is washed with water and then with an aqueous saturated sodium chloride solution. The ethyl acetate solution is dried over magnesium sulfate, gravity or vacuum filtered, and then concentrated. The product is purified by silica gel chromatography.

Starting materials for use in the general synthetic procedures outlined in the above reaction schemes are readily available or can readily be prepared according to standard techniques and procedures. Probucol is readily available from Sigma Chemicals.

The following examples present typical syntheses as described in Schemes B and C. These examples are understood to be illustrative only and are not intended to limit the scope of the present invention in any way.

EXAMPLE 20

Pentanedioic acid, 4-[[1-[[3,5-bis(1,1-dimethylethyl) 4-hydroxyphenyl]thio]-1-methylethyl]thio]-,6-bis(1, 1-dimethylethyl)phenyl methyl ester Reaction Description Probucol (2.8 g, 5.5 mmol) was taken up in THF (25 mL), 60% sodium hydride in mineral oil (528 mg, 13.2 mmol) was added followed by the addition of methyl chloroformyl butyrate (0.751 mL, 6.6 mmol). After 2 h the reaction was quenched with methanol (3 mL), followed by water (10 mL). The reaction mixture was extracted with ether (50 mL), concentrated and chromatographed on silica gel eluting with a concentration gradient of 0:100 ether/hexanes to 20:80 ether/hexanes. The reaction yielded 500 mg of the product. 7.63 (s, 2 H), 7.45 (s, 2 H), 5.82 (s, 1 H), 3.71 (s, 3 H), 2.73 (t, J=7.6 Hz, 2 H), 2.50 (t, J=7.2 Hz, 2 H), 2.07 (pent, J=7.6 Hz, 2 H), 1.47 (s, 6 H), 1.44 (s, 18 H), 1.34 (s, 18 H).

EXAMPLE 21

Phenol, 4-[[1-[3,5-bis(1,1-dimethylethyl)-4-[(4-nitrophenyl)methoxy]phenyl]thio]-1-methylethyl] thio]2,6-bis(1,1-dimethylethyl)-

Reaction Description

A solution of probucol (0.19 mmol; 100 mg) in dry DMF (1 mL) was stirred and treated with sodium hydride (0.28 mmol; 11 mg; 60% dispersion in mineral oil) followed by 4-nitrobenzyl iodide (0.24 mmol; 63 mg). The mixture was stirred for 18 h during which it turned yellow-green. The mixture was quenched with brine then extracted with 3×2 mL of $Et_2O$. The combined organic layers were dried over $MgSO_4$, filtered, and concentrated by rotary evaporation to give a brown oil. Purification by radial chromatography (2 mm plate; 1:1 hexanes-$CH_2Cl_2$ as eluant) gave the product as a yellow solid (53 mg; 43% yield). $^1H$ NMR ($CDCl_3$, 400 MHz): δ8.06 (d, J=7.6 Hz, 2 H), 7.35 (s, 2 H), 7.14 (d, J=7.2 Hz, 2 H), 6.79 (s, 2 H), 5.41 (s, 1 H), 3.13 (s, 2 H), 1.45–1.43 (overlapping s, 21 H), 1.14(s, 21 H).

EXAMPLE 22

Butanedioic acid, mono [4-[[1-[[3,5-bis(1,1-dimethylethyl)-4-hydroxyphenyl]thio]-1-methylethyl]thio]2,6-bis(1,1-dimethylethyl)phenyl] ester Reaction Description To a 50 mL recovery flask was added probucol (1.0 g, 1.93 mmol) and tetrahydrofuran (16 mL). To the solution was added 60% sodium hydride in mineral oil (0.23 g, 5.75 mmol). To the cloudy white mixture was added succinic anhydride (0.58 g, 5.8 mmol) in THF(12 mL). The reaction dark purple and was stirred at room temperature for 3 h. The dark purple reaction mixture was made acidic with 1 N HCl (25 mL) and extracted twice with ethyl acetate (50 mL). The organic extracts were dried over $MgSO_4$, filtered and concentrated affording an orange solid. The orange solid was dissolved in ether and chromatographed on silica gel with a concentration gradient of 70:30 hexane/ether to 0:100 hexane/ether. The appropriate fractions were combined and concentrated affording a white solid. (170 mgm 0.276 mmol, 14%). TLC (silica gel, 60:40 ether/hexane+10 drops HOAc, $R_f$=0.35); $^1H$ NMR ($CDCl_3$, 400 MHZ): δ7.61 (s, 2 H), 7.43 (s, 2 H), 5.38 (s, 1 H), 2.97 (t, J=6.8 Hz, 2 H), 2.76 (t, J=6.8 Hz, 2 H), 1.45 (s, 8 H), 1.42 (s, 16 H), 1.32 (s, 18 H).

EXAMPLE 23

2-Furancarboxylic acid, 5-nitro-, 4-[[1-[[3,5-bis(1,1-dimethylethyl)-4-hydroxyphenyl]thio]-1-methylethyl]thio]-2,6-bis(1,1-dimethylethyl)phenyl ester Reaction Description A solution of 0.39 mmol (200 mg) of probucol in dry THF (3.9 mL) was treated with sodium hydride (0.58 mmol; 23 mg; 60% dispersion in mineral oil) and stirred for 10 min. at room temperature. The clear mixture turned purple upon the addition of 4-nitrofuroyl chloride (0.77 mmol; 136 mg). The mixture was stirred for 47 h during which it turned brown, and precipitation was observed. The reaction mixture was diluted with $Et_2O$ (40 mL), washed with $H_2O$ (15 mL) then dried over $Na_2SO_4$ and concentrated by rotary evaporation to give a crude, yellow-orange solid. Purification by radial chromatography (2 mm $SiO_2$ plate; 1:1 hexanes-$CH_2Cl_2$ as eluant) gave 4,4'-(isopropylidenedithio)[O-(5"-nitro-2"-furoyl)-2',6'-di-tert-butylphenol]-[2,6-di-tert-butylphenol] (83 mg; 33% yield). $^1H$ NMR ($CDCl_3$, 400 MHz): δ7.70 (s, 2 H), 7.50 (d, J=4.0 Hz, 1 H), 7.45 (d, J=3.6 Hz, 1 H), 7.45 (s, 2 H), 5.39 (s, 1 H), 1.50 (s, 6 H), 1.45 (s, 14 H), 1.35 (s, 22 H).

EXAMPLE 24

Butanoic acid, 4-[4-[[1-[[3,5-bis(1,1-dimethylethyl)-4-hydroxyphenyl]thio]-1-methylethyl]thio]2,6-dimethylphenoxy]-

Reaction Description 4,4'-(isopropylidenedithio)[2',6'-di-methylphenol][2,6-di-tert-butylphenol] (0.55 mmol; 0.24 g) was dissolved in dry DMF (5.5 mL). Sodium hydride (1.38 mmol; 33 mg) was added to the mixture followed by methyl 4-iodobutyrate (0.83 mmol; 188 mg). The resulting mixture was stirred at room temperature for 4.5 h during which it turned green. The reaction was quenched with 0.3 N HCl (ca. 6 mL) causing the mixture to turn yellow. Dilution with $Et_2O$ (25 mL) was followed by washing with $H_2O$ (10 mL) and brine (10 mL). The solution was dried over $MgSO_4$ then concentrated by rotary evaporation. Purification by MPLC (($SiO_2$; solvent gradient: 100% hexanes then 95:5 hexanes-$Et_2O$ then 90:10 hexanes-$Et_2O$ then 80:20 hexanes-$Et_2O$) gave the desired intermediate as a yellow oil (197 mg; 67% yield). The oil (0.35 mmol; 187 mg) was taken up in 4:1:1 MeOH-THF-$H_2O$ (3.5 mL). LiOH monohydrate (1.05 mmol; 44 mg) was added, and the mixture was stirred for 1.75 h at room temperature. The reaction mixture was then acidified with 0.1 N HCl to pH 4. Extraction with 3×15 mL of EtOAc then drying the combined extracts over $MgSO_4$ and concentration by rotary evaporation gave the crude product. Purification by MPLC (SiO$_2$; solvent gradient: 100% hexanes to 60:40 Et$_2$O-hexanes (acidified with trace of acetic acid)) gave 4,4'-(isopropylidenedithio)[O-(γ-butyric acid)-2',6'-dimethylphenol][2,6-di-tert-butylphenol] as a yellow foam (100 mg; 55% yield). $^1$H NMR (CDCl$_3$, 400 MHz): δ7.44 (s, 2 H), 7.25 (s, 2 H), 5.38 (s, 1 H), 3.83 (app t, J=6.0 Hz, 2 H), 2.68 (app t, J=8.0 Hz, 2 H), 2.25 (s, 6 H), 2.14 (m, 2 H), 1.47 (s, 6 H), 1.45 (s, 18 H).

EXAMPLE 25

Phenol, 4-[[1-[[4-(4-aminobutoxy)-3,5-bis(1,1-dimethylethyl)phenyl]thio]-1-methylethyl]thio]2,6-bis(1,1-dimethylethyl)-

Reaction Description 4,4'-(isopropylidenedithio)[2',6'-di-methylphenol][2,6-di-tert-butylphenol] (1.44 mmol; 622 mg) was dissolved in dry DMF (14.4 mL) and treated with sodium hydride (3.6 mmol; 144 mg). Tetrabutylammonium iodide (0.72 mmol; 266 mg) was added followed by (N-bromobutyl)phthalimide (2.2 mmol; 608 mg). The mixture was stirred at room temperature for 17 h during which it turned dark green. The mixture was quenched with 0.3 N HCl (6 mL) then diluted with Et2O (100 mL). Washing was done with H$_2$O (50 mL) and brine (50 mL). The aqueous layer was treated with NaCl then back-extracted with Et$_2$O. The combined organic layers were dried over MgSO$_4$ then concentrated by rotary evaporation. Purification by MPLC (SiO$_2$; solvent gradient: 100% hexanes to 75:25 hexanes-Et$_2$O) gave the desired intermediate as a yellow-brown oil (750 mg; 82% yield). The intermediate (0.89 mmol; 563 mg) was dissolved in dry DMF (8.9 mL) and treated with hydrazine hydrate ((27 mmol; 0.83 mL). The mixture was stirred at room temperature for 42 h. The reaction mixture was treated with 1 N HCl (8.9 mL) and stirred for 1.5 h; NaHCO$_3$ was added to adjust to pH 7 then extracted with EtOAc (2×15 mL) and dried over MgSO$_4$. Solvent removal by rotary evaporation followed by purification by MPLC (SiO$_2$; solvent gradient: 50:50 MeOH—CH$_2$Cl$_2$ to 49.5:49.5:1 MeOH—CH$_2$Cl$_2$—NH$_4$OH) gave 4,4'-(isopropylidenedithio)[O-(aminobutyl)-2',6'-di-methylphenol][2,6-di-tert-butylphenol] (93 mg; 21% yield). $^1$H NMR (CDCl$_3$, 400 MHz): δ7.42 (s, 2 H), 7.22 (s, 2 H), 5.55 (s, 1 H), 3.76 (app t, J=6.8 Hz, 2 H), 2.78 (app t, J=6.8 Hz, 2 H), 2.24 (s, 6 H), 1.83 (m, 2 H), 1.66 (m, 2 H), 1.45 (s, 6 H), 1.42 (s, 18 H).

EXAMPLE 26

Phenol, 4-[[1-[[4-(4-aminobutoxy)-3,5-bis(1,1-dimethylethyl)phenyl]thio]-1-methylethyl]thio]2,6-bis(1,1-dimethylethyl)-

Reaction Description

Probucol (9.7 mmol; 5 g) was dissolved in dry DMF (14.5 mL) and treated with (N-bromobutyl)phthalimide (13.6 mmol; 3.82 g) and KF on alumina (48.4 mmol; 7.03 g). The reaction mixture was stirred at room temperature for 18 h then at 80° C. for 4 h. The mixture was filtered through a fritted funnel, and the residue was washed with H$_2$O (10 mL) and Et$_2$O (10 mL). The filtrate was diluted with Et$_2$O (200 mL) then washed with H$_2$O (50 mL and brine (50 mL). The combined organic layers were dried over MgSO$_4$ and concentrated by rotary evaporation. Purification by MPLC (SiO$_2$; solvent gradient: 100% hexanes to 80:20 hexanes-Et$_2$O) gave the desired intermediate as a brown foam (346 mg; 5% yield). The intermediate (0.44 mmol; 314 mg) was taken up in DMF (4.4 mL) and treated with hydrazine hydrate (13 mmol; 0.41 mL) to give a green color. The mixture was stirred at room temperature for 16 h then treated with 1 N HCl (4.7 mL) and stirred for another 1.5 h. NaHCO$_3$ was added to adjust the mixture to pH 7. Extraction with 2×30 mL of EtOAc followed by washing the organic extracts with brine (20 mL), drying over MgSO$_4$, and solvent removal by rotary evaporation gave a green liquid. Purification by MPLC (SiO$_2$; solvent gradient: 100% CH$_2$Cl$_2$ to 90:10 CH$_2$Cl$_2$—MeOH) gave 4,4'-(isopropylidenedithio)[O-(aminobutyl)-2',6'-di-tert-butylphenol][2,6-di-tert-butylphenol] as a yellow solid (182 mg; 71% yield). $^1$H NMR (CDCl$_3$, 400 MHz): 8 7.52 (s, 2 H), 7.44 (s, 2 H), 5.28 (s, 1 H), 5.25 (br s, 2 H), 3.72–3.69 (m, 2 H), 2.92–2.88 (m, 2 H), 1.94–1.90 (m, 2 H), 1.73–1.69 (m, 2 H), 1.43 (s, 22 H), 1.40 (s, 20 H).

EXAMPLE 27

Butanoic acid, 4-hydorxy-, 4-[[1-[[3,5-bis(1,1-dimethylethyl)-4-hydroxyphenyl]thio]-1-methylethyl]thio]-2,6-bis(1,1-dimethylethyl)phenyl ester

Reaction Description

To a solution of the compound of example 22 (6.17 g, 10 mmol) in THF (200 ml) cooled to −78° C. was slowly added borane-methyl sulfide (10 ml, 2 M solution in THF). The resultant mixture was stirred overnight under nitrogen while the cooling bath was allowed to warm to room temperature. Then it was cooled to 0° C., hydrogen chloride (37%, 4 ml) was added and the mixture was stirred at room temperature overnight. The mixture was evaporated to a residue and distributed between ethyl acetate (100 ml) and brine (100 ml). The organic phase was washed with 1 N sodium hydroxide solution (100 ml) and then brine (100 ml), dried over magnesium sulfate and evaporated. Silica gel chromatography (dichloromethane) gave the title compound as a viscous residue. Crystalyzation from hexanes/dichloromethane gave white crystals (5.5 g). MP: 138–139° C. $^1$H-NMR (400 MHz, CDCl$_3$): 7.63 (s, 2 H), 7.45 (s, 2 H), 5.38 (s, 1 H), 3.76 (t, 2 H), 2.79 (t, 2 H), 2.01 (m, 2 H), 1.47 (s, 6 H), 1.44 (s, 18 H), 1.34 (s, 18 H).

EXAMPLE 28

Propanoic acid, 2,2-dimethyl-, [4-[[1-[[3,5-bis(1,1-dimethylethyl)-4 hydroxyphenyl]thio]-1-methylethyl]thio]-2,6-bis(1,1-dimethylethyl) phenoxymethyl ester To a suspension of probucol (5.17 g, 10 mmol) in acetonitrile (30 ml) were added chloromethyl pivalate (6.0 g, 40 mmol) and potassium fluoride (8.0 g, 40% on alumina). The resultant mixture was stirred under nitrogen at reflux for 18 hours. After cooled to room temperature it was filtered and rinsed with dichloromethane (100 ml). The filtrate was washed with brine (100 ml), dried over magnesium sulfate and evaporated. Silica gel chromatography (hexanes/dichloromethane 4:1) gave the title compound as a yellow oil (0.39 g). $^1$H-NMR (400 MHz, CDCl$_3$): 7.59 (s, 2 H), 7.45 (s, 2 H), 5.49 (s, 2 H), 5.38 (s, 1 H), 1.464 (s, 6 H), 1.457 (s, 18 H), 1.445 (s, 18 H), 1.28 (s, 9 H).

EXAMPLE 29

Phenol, 4-[[1-[[4-(4-aminobutoxy)phenyl]thio]-1-methylethyl]thio]-2,6-bis(1,1-dimethylethyl)-

Reaction Description

A solution of: 4,4'-(isopropylidenedithio)[phenol][2,6-di-tert-butylphenol] (0.18 mmol; 75 mg) in 2 mL of dry DMF was stirred and treated with 0.23 mmol (9 mg) of sodium hydride (60% dispersion in mineral oil) to give a yellow mixture. N-(4-bromobutyl)phthalimide (0.22 mmol; 63 mg) was added followed by 0.22 mmol (33 mg) of NaI. The mixture was heated to 120° C., turning a dark green color. After 24 h, TLC ($SiO_2$; $CH_2Cl_2$ as eluant; visualization by UV, PMA/char) showed only traces of starting material present. The reaction mixture was cooled to room temperature then quenched with 3 mL each of $Et_2O$ and sat. NaCl. The aqueous layer was back-extracted with 3 mL of $Et_2O$; the combined organic layers were dried over $MgSO_4$, filtered, and concentrated by rotary evaporation to give a dark brown oil. Purification by column chromatography ($SiO_2$; 20×170 mm column; $CH_2Cl_2$ as eluant) gave the desired intermediate in 69% yield (69 mg). The intermediate (0.11 mmol; 69 mg) was taken up in 1 mL of DMF and stirred. Hydrazine hydrate (0.16 mmol; 8 µL) was added, causing a color change from yellow to deep blue-green. The reaction mixture was stirred at room temperature for 1 week by which time it had turned a clear yellow. TLC showed the presence of starting material. Additional hydrazine hydrate (10.3 mmol; 0.5 mL) was added; the mixture was stirred for another 24 h, after which starting material was completely consumed. The mixture was quenched with 12 N HCl to adjust the pH to 3. After stirring for 5 min., sat. $NaHCO_3$ was added to neutralize the acid (final pH=7). EtOAC was added, and the aqueous layer was back-extracted with 2×2 mL of EtOAc. The combined organic layers were dried over $MgSO_4$, filtered and concentrated by rotary evaporation. The crude product was purified by column chromatography ($SiO_2$; 15×110 mm column; EtOH as eluant) to give 4,4'-(isopropylidenedithio)[O-(aminobutyl)phenol][2,6-di-tert-butylphenol] (25 mg; 48% yield) as a yellow solid. $^1$H NMR ($CDCl_3$, 400 MHZ): δ7.50 (d, J=8.4 Hz, 2 H), 7.42 (s, 2 H), 6.83 (d, J=8.4 Hz, 2 H), 5.36 (br s, 1 H), 3.97 (br m, 2 H), 3.10 (br m, 2 H), 2.01–1.86 (overlapping m, 4 H), 1.43 (s, 24 H).

EXAMPLE 30

Butanoic acid, 4-[4-[[1-[[3,5-bis(1,1-dimethylethyl)-4-hydroxyphenyl]thio]-1-methylethyl]thio]phenoxy]-

Reaction Description

A solution of: 4,4'-(isopropylidenedithio)[phenol][2,6-di-tert-butylphenol] (0.6 mmol; 242 mg) in 6 mL of dry DMF was stirred and treated with 1.3 mmol (53 mg) of sodium hydride (60% dispersion in mineral oil) to give a brown solution. The reaction mixture was treated with 0.9 mmol (131 µL) of methyl 4-iodobutyrate. The progress of the reaction was monitored by TLC using $CH_2Cl_2$ as eluant (visualization by UV, PMA/char). After 24 h, TLC of the dark green mixture showed predominantly product. The mixture was quenched with sat. NaCl and $Et_2O$. The aqueous layer was back-extracted with 2×6 mL of $Et_2O$; the combined organic layers were dried over $MgSO_4$, filtered, and concentrated by rotary evaporation to give a crude oil. Column chromatography ($SiO_2$; 20×185 mm column) using $CH_2Cl_2$ gave 232 mg (77% yield) of the desired intermediate which was taken up and stirred in 3 mL of 4:1:1 MeOH-THF-$H_2O$. The pale yellow solution was treated with 0.92 mmol (39 mg) of LiOH monohydrate to give a greenish-yellow solution. The mixture was stirred at room temperature until all starting material was consumed (ca. 18 h) then treated with 12 N HCl to adjust the pH to 2 (yellow mixture). $Et_2O$ (5 mL) was added; the aqueous layer was back-extracted with 2×5 mL of $Et_2O$. The combined organic layers were dried over $MgSO_4$, filtered then concentrated by rotary evaporation to give a crude solid. Purification by column chromatography ($SiO_2$; 15×180 mm column; 3:1 hexanes-EtOH as eluant) gave 4,4'-(isopropylidenedithio)[O-(γ-butyric acid)phenol][2,6di-tert-butylphenol] as an oil (62 mg; 40% yield). $^1$H NMR ($CDCl_3$, 400 MHZ): δ7.47 (d, J=8.0 Hz, 2 H), 7.40 (s, 2 H), 6.80 (d, J=7.6 Hz, 2 H), 5.35 (s, 1 H), 3.93 (br m, 2 H), 2.51 (br m, 2 H), 2.07 (br m, 2 H), 1.42 (s, 18 H), 1.25 (s, 6 H).

EXAMPLE 31

Acetic acid, [4-[[1-[[3,5-bis(1,1-dimethylethyl)-4-hydroxyphenyl]thio]-1-methylethyl]thio]2,6-bis(1,1-dimethylethyl)phenoxy]-

Reaction Description

To dimethylformamide (1.5 mL) was added probucol(0.5 g, 0.967 mmol) and ethyl-2-iodo acetate (0.31 g, 1.45 mmol) and 40% potassium fluoride on alumina (0.7 g) and the reaction was stirred for 24 hours. The reaction mixture was diluted with ether (25 mL), filtered and washed with water (2×5 mL). The ether layer was dried over $MgSO_4$, filtered and concentrated. The resulting oil was purified by radial silica gel chromatography by elution with 5:95 ether/hexanes to yield 160 mg of the ethyl ester of the product. The ethyl ester dissolved in THF:$H_2$0:MeOH(4:1:1)(4 mL) and LiOH—$H_2O$ (50 mg) was added and the reaction stirred for 1 h. The reaction was neutralized with 1N HCl and extracted with ether (2×10 mL), dried over $MgSO_4$, filtered, and concentrated. Silica gel chromatography and elution with 50:50 ether/hexanes gave 90 mg of the product. $^1$H NMR ($CDCl_3$, 400 MHZ): δ7.55 (s, 2 H), 7.40 (s, 2 H), 5.35 (s, 1 H), 4.40 (s, 2 H), 1.43 (s, 6 H), 1.41 (s, 9 H), 1.39 (s, 9 H).

EXAMPLE 32

Glycine, 4-[[1-[[3,5-bis(1,1-dimethylethyl)-4-hydroxyphenyl]thio]-1-methylethyl]thio]-2,6-bis(1,1-dimethylethyl)phenyl ester Reaction Description To a solution of probucol (3.0 g, 5.8 mmol) in THF (58 mL) was added 60% sodium hydride (1.16 g, 29.0 mmol) and the reaction stirred for 0.5 h at room temperature. The acid chloride of phthaloyl glycine was added and the reaction stirred an additional 0.5 h. The reaction was then diluted with ethyl acetate (150 mL), quenched with water (5 mL), then washed with water (2×50 mL) and brine (1×50 mL). The organic layer was dried over $MgSO_4$, filtered and concentrated. The resulting oil was chromatographed on silica gel eluting with 10% ethyl acetate/hexane followed by 20% ethyl acetate/hexane to yield 610 mg of the phthaloyl glycine ester. The phthaloyl glycine ester was taken up in DMF(8.6 mL) and hydrazine hydrate was added (0.136 mL, 2.34 mmol) and the reaction stirred overnight. 1 N HCl was added (5 mL) and the reaction stirred an additional 1 h. The reaction was diluted with ethyl acetate (25 mL) and washed with NaHCO3 (aq) (1×10 mL). The ethyl acetate layer was dried over $MgSO_4$, filtered, concentrated, and chromatographed on silica gel, eluting with 1% methanol/methylene chloride followed by 1.5% methanol/methylene chloride to yield 334 mg of product. 7.64 (s, 2 H), 7.45 (s, 2 H), 5.39 (br s, 1 H), 3.76 (s, 2 H), 1.48 (s, 6 H), 1.44 (s, 18 H), 1.33 (s, 18 H).

EXAMPLE 33

Pentanedioic acid, mono[4-[[1-[[3,5-bis(1,1-dimethylethyl)-4-hydroxyphenyl]thio]-1-methylethyl]thio]-2,6-bis(1,1-dimethylethyl)phenyl] ester

Reaction Description

To a 50 mL recovery flask was added probucol(1.0 g, 1.93 mmol) and tetrahydrofuran (20 mL). To the solution was added 60% sodium hydride in mineral oil (0.16 g, 4 mmol). To the cloudy white mixture was added glutaric anhydride (0.170 g, 3 mmol) in THF(12 mL). The reaction was stirred at room temperature for 3 h. The reaction mixture was made acidic with 1N HCl (25 mL) and extracted twice with ethyl acetate (50 mL). The organic extracts were dried over $MgSO_4$, filtered and concentrated affording a yellow oil. The yellow oil was dissolved in ether and chromatographed on silica gel with a concentration gradient of 70:30 hexane/ether to 0:100 hexane/ether. The appropriate fractions were combined and concentrated affording a white solid. 7.62 (s, 2 H), 7.45 (s, 2 H), 5.37 (s, 1 H), 2.75 (t, J=7.2 Hz, 2 H), 2.55 (t, J=7.2 Hz, 2 H), 2.09 (m, 2 H), 1.47 (s, 6 H), 1.44 (s, 18 H), 1.43 (H).

EXAMPLE 34

Butanoic acid, 4-[4-[[1-[[3,5-bis(1,1-dimethylethyl) 4-hydroxyphenyl]thio]-1-methylethyl]thio]-2,6-bis(1,1-dimethylethyl)phenoxy]-

Reaction Description

Probucol (5 g, 9.7 mmol) was stirred together with methyl 4-iodobutyrate (3.1 g, 13.6 mmol) in DMF (15 mL). To the reaction mixture was added 40% potassium flouride on alumina (7 g, 48 mmol) and stirring continued at room temperature overnight. The green reaction mixture was filtered into a separatory funnel, diluted with ethyl acetate (50 mL) and washed with water (2×20 mL) and saturated aqueous sodium chloride (1×20 mL). The ethyl acetate layer was dried over $MgSO_4$, fileterd, concentrated and chromatographed on silia gel by elution with a concentration gradient of 10:90 methylene chloride/hexane to 60:40 methylene chloride hexane. The appropriate fractions were collected and concentrated to afford 442 mg of a white solid. The methyl ester was taken up in $THF:MeOH:H_2O$ (4:1:1)(5 mL) and lithium hydroxide (63 mg, 1.5 mmol) was added. After 2.5 h the reaction was complete and quenched with 1 N HCl (3 mL) and extracted with ethyl acetate (15 mL). The ethyl acetate solution was washed with saturated aqueous sodium chloride (3 mL), dried over $MgSO_4$, filtered and concentrated. Chromatography over silica gel, eluting with a solvent gradient of 10:90 ether/hexanes to 50:50 ether/hexanes afforded 308 mg of product. 7.53 (s, 2 H), 7.45 (s, 2 H), 5.37 (s, 1 H), 3.77 (t, J=6.8 Hz, 2 H), 2.55 (t, J=7.6 Hz, 2 H), 2.16 (m, 2 H), 1.44 (s, 24 H), 1.41 (s, 18 H).

EXAMPLE 35

Oxiranemethanol, α-[[4-[[1-[[3,5-bis(1,1-dimethylethyl)-4hydroxyphenyl]thio]-1-methylethyl] thio]-2,6-bis(1,1-dimethylethyl)phenoxy]methyl]-

Oxiranemethanol, 3-[[4-[[1-[[3,5-bis(1,1-dimethylethyl)-4-hydroxyphenyl]thio]-1-methylethyl]thio]-2,6-bis(1,1-dimethylethyl) phenoxy]methyl]-

Oxiranemethanol, α-[[[3-[[4-[[1-[[3,5-bis(1,1-dimethylethyl)-4-hydroxyphenyl]thio]-1-methylethyl]thio]-2,6-bis(1,1-dimethylethyl) phenoxy]methyl]oxiranyl]methoxy]methyl]-

To a solution of probucol (5.16 g, 10 mmol) in acetonitrile (50 ml) were added 1,3-butadiene diepoxide (1.6 ml, 20 mmol) and potassium fluoride (2.9 g, 20 mmol, 40% on alumina). The resultant mixture was stirred under nitrogen at reflux for 18 hours. After cooled to room temperature it was poured into dichloromethane (150 ml), washed with water (2×100 ml), dried over magnesium and evaporated. Silica gel chromatography (hexanes/dichloromethane 2:1, 1:1, 1:2 and then dichloromethane) gave Oxiranemethanol, α-[[4-[[1-[[3,5-bis(1,1-dimethylethyl)-4-hydroxyphenyl]thio]-1-methylethyl]thio]-2,6-bis(1,1-dimethylethyl)phenoxy] methyl]- (0.47 g), Oxiranemethanol, 3-[[4-[[1-[[3,5-bis(1,1-dimethylethyl)-4-hydroxyphenyl]thio]-1-methylethyl]thio]-2,6-bis(1,1-dimethylethyl)phenoxy]methyl]- (0.15 g) and Oxiranemethanol, α-[[[3-[[4-[[1-[[3,5-bis(1,1-dimethylethyl)-4-hydroxyphenyl]thio]-1-methylethyl]thio]-2,6-bis(1,1-dimethylethyl)phenoxy]methyl]oxiranyl] methoxy]methyl]- (0.05 g).

Oxiranemethanol, α-[[4-[[1-[[3,5-bis(1,1-dimethylethyl)-4-hydroxyphenyl]thio]-1-methylethyl]thio]-2,6-bis(1,1-dimethylethyl) phenoxy]methyl]-

$^1$H-NMR (400 MHz, $CDCl_3$): 7.56 (s, 2 H), 7.45 (s, 2 H), 5.38 (s, 1 H), 4.10–4.17 (m, 1 H), 3.83–3.97 (m, 2 H), 3.27–3.32 (m, 1 H), 2.83–2.94 (m, 2 H), 2.18 (br. s, 1 H), 1.46 (s, 6 H), 1.45 (s, 18 H), 1.44 (s, 18 H).

Oxiranemethanol, 3-[[4-[[1-[[3,5-bis(1,1-dimethylethyl)-4hydroxyphenyl]thio]-1-methylethyl] thio]-2,6-bis(1,1-dimethylethyl)phenoxy]methyl]-

$^1$H-NMR (400 MHz, $CDCl_3$): 7.56 (s, 2 H), 7.45 (s, 2 H), 5.39 (s, 1 H), 4.38 (m, 2 H), 4.00 (m, 2 H), 3.89 (m, 2 H), 1.34–1.41 (m, 42 H).

Oxiranemethanol, α-[[[3-[[4-[[1-[[3,5-bis(1,1-dimethylethyl)-4-hydroxyphenyl]thio]-1-methylethyl]thio]-2,6-bis(1,1-dimethylethyl) phenoxy]methyl]oxiranyl]methoxy]methyl]-

$^1$H-NMR (400 MHz, $CDCl_3$): 7.54 (s, 2 H), 7.45 (s, 2 H), 5.39 (s, 1 H), 4.24 (br. m, 1 H), 3.93 (m, 1 H), 3.81 (m, 1 H), 3.77 (br. m, 1 H), 3.16 (m, 1 H), 3.06 (m, 1 H), 2.91 (m, 1 H), 2.85 (m, 2 H), 2.84 (m, 1 H), 2.75 (m, 2 H), 1.41–1.44 (m, 42 H).

EXAMPLE 36

Phenol, 4-[[1-[[3,5-bis(1,1-dimethylethyl)-4 (oxiranylmethoxy)phenyl]thio]-1-methylethyl]thio]-2,6-bis(1,1-dimethylethyl)-

To a solution of probucol (2,58 g, 5 mmol) in THF (50 ml) cooled to 0° C. were added glycidol (0.66 ml, 10 mmol), triphenyl phosphine (2.62 g, 10 mmol), and diethyl azodicarboxylate (1.57 ml, 10 mmol). The resultant mixture was stirred under nitrogen at reflux for 48 hours and then evaporated. Silica gel chromatography (hexanes/dichloromethane 4:1, 2:1) gave the title compound as a viscous residue (1.01 g). $^1$H-NMR (400 MHz, $CDCl_3$): 7.56 (s, 2 H), 7.44 (s, 2 H), 5.39 (s, 1 H), 4.40 (m, 1 H), 3.75 (m, 1 H), 3.39 (m, 1 H), 2.91 (m, 1 H), 2.77 (m, 1 H), 1.40–1.49 (m, 42 H).

EXAMPLE 37

Glycine, N-[3-[4-[[1-[(3,5-bis(1,1-dimethylethyl)-4-hydroxyphenyl]thio]-1-methylethyl]thio]-2,6-bis(1,1-dimethylethyl)phenoxy]2-hydroxypropyl]-

To suspension of Phenol, 4-[[1-[[3,5-bis(1,1-dimethylethyl)-4-(oxiranylmethoxy)phenyl]thio]-1-methylethyl]thio]-2,6-bis(1,1-dimethylethyl)- (0.17 g, 0.28 mmol) in ethanol (10 ml) were added glycine (43 mg, 0.57 mmol) and triethylamine (1 ml). The resultant mixture was stirred under nitrogen at reflux overnight. The mixture became a solution upon heating. It was then evaporated. Silica gel chromatography (dichloromethane/methanol 10:1 to 1:1) give the title compound (99 mg). $^1$H-NMR (400 MHz, CDCl$_3$): 7.52 (s, 2 H), 7.43 (s, 2 H), 5.37 (s, 1 H), 4.58 (br. s, 1 H), 3.79 (br. m, 2 H), 3.67 (m, 1 H), 3.30 (m, 1 H), 3.21 (m, 1 H), 3.13 (m, 1 H), 1.43 (s, 18 H), 1.41 (s, 6 H), 1.38 (s, 18 H).

EXAMPLE 38

1,2,3-Butanetriol, 4-[4-[[1-[[3,5-bis(1,1-dimethylethyl)-4-hydroxyphenyl]thio]=1-methylethyl]thio]-2,6-bis(1,1-dimethylethyl)phenoxy]-2-hydroxypropyl]-

To a solution of Oxiranemethanol, α-[[4-[[1-[[3,5-bis(1,1-dimethylethyl)-4-hydroxyphenyl]thio]-1-methylethyl]thio]-2,6-bis(1,1-dimethylethyl)phenoxy]methyl]-(0.15 g) in actonitrile (5 ml) were added water (1 ml) and concetrated sulfuric acid (10 drops). The resultant mixture was stirred at room temperature for 48 hours and then poured into brine (50 ml), extracted with dichloromethane (3×50 ml), dried over magnesium sulfate and evaporated. Silica gel chromatography (dichloromethane/ethyl acetate 3:1) gave the title compound as a colorless viscous residue (26 mg). $^1$H-NMR (400 MHz, CDCl$_3$): 7.54 (s, 2 H), 7.43 (s, 2 H), 5.36 (s, 1 H), 4.27 (m, 2 H), 3.98 (m, 2 H), 3.75 (m, 2 H), 1.36–1.44 (m, 42 H).

EXAMPLE 39

Phenol, 4-[[1-[[3,5-bis(1,1-dimethylethyl)-4(3-ethoxy-2-hydroxypropoxy)phenyl]thio]-1-methylethyl]thiol-2,6-bis(1,1-dimethylethyl)-

1,2-Propanediol, 3-[4-[[1-[[3,5-bis(1,1-dimethylethyl)-4-hydroxyphenyl]thio]-1-methylethyl]thio]-2,6-bis(1,1-dimethylethyl)phenoxy]-

To a suspension of Oxiranemethanol, α-[[[3-[[4-[[1-[[3,5-bis(1,1-dimethylethyl)-4-hydroxyphenyl]thio]-1-methylethyl]thio]-2,6-bis(1,1-dimethylethyl)phenoxy]methyl]oxiranyl]methoxy]methyl]- (0.32 g) in ethanol (10 ml) was added 1 N sodium hydroxide solution (1.5 ml). The resultant mixture was stirred at reflux for three days and then evaporated. The residue was distributed between ethyl acetate (50 ml) and brine (50 ml). The organic phase was washed with brine (50 ml), dried over magnesium sulfate and evaporated. Silica gel chromatography (hexanes/dichloromethane 1:1, dichloromethane and then dichloromethane/ethyl acetate 4:1) afforded 1,2-Propanediol, 3-[4-[[1-[[3,5-bis(1,1-dimethylethyl)-4-hydroxyphenyl]thio]-1-methylethyl]thio]-2,6-bis(1,1-dimethylethyl)phenoxy]- (58 mg) and a mixture that contained the Phenol, 4-[[1-[[3,5-bis(1,1-dimethylethyl)-4-(3-ethoxy-2-hydroxypropoxy)phenyl]thio]-1-methylethyl]thio]-2,6-bis(1,1-dimethylethyl)-, which was re-columned (hexanes/ethyl acetate 5:1) and Phenol, 4-[[1-[[3,5-bis(1,1-dimethylethyl)-4-(3-ethoxy-2-hydroxypropoxy)phenyl]thio]-1-methylethyl]thio]-2,6-bis(1,1-dimethylethyl)- was obtained in pure form (52 mg).

Phenol, 4-[[1-[[3,5-bis(1,1-dimethylethyl)-4-(3-ethoxy-2-hydroxypropoxy)phenyl]thio]-1-methylethyl]thio]-2,6-bis(1,1-dimethylethyl)-

$^1$H-NMR (400 MHz, CDCl$_3$): 7.55 (s, 2 H), 7.45 (s, 2 H), 5.38 (s, 1 H), 4.35 (m, 1 H), 4.11 (m, 1 H), 3.83 (m, 2 H), 3.62 (m, 1H), 3.57 (m, 2 H), 1.43–1.46 (m, 42 H), 1.22 (t, 3 H).

1,2-Propanediol, 3-[4-[[1-[[3,5-bis(1,1-dimethylethyl)-4-hydroxyphenyl]thio]-1-methylethyl]thio]-2,6-bis(1,1-dimethylethyl)phenoxyl- $^1$H-NMR (400 MHz, CDCl$_3$): 7.56 (s, 2 H), 7.45 (s, 2 H), 5.38 (s, 1 H), 4.32 (m, 1 H), 3.94 (dd, 1 H), 3.85 (m, 1 H), 3.77 (m, 1 H), 3.66 (m, 1 H), 1.40–1.44 (m, 42 H).

EXAMPLE 40

Phenol, 4-[[1-[[3,5-bis(1,1-dimethylethyl)-4ethoxyphenyl]thio]-1-methylethyl]thio]-2,6-bis(1,1-dimethylethyl)-

2-Propenoic acid, 3-[4-[[1-[[3,5-bis(1,1-dimethylethyl)-4hydroxyphenyl]thio]-1-methylethyl]thio]-2,6-bis(1,1-dimethylethyl)phenoxy]-, ethyl ester, (E)-

2-Propenoic acid, 3-[4-[[1-[[3,5-bis(1,1-dimethylethyl)-4ethoxyphenyl]thio]-1-methylethyl]thio]-2,6-bis(1,1-dimethylethyl)phenoxy]-, ethyl ester, (E)-

To a solution of probucol (5.16 g, 10 mmol) in THF (50 ml) were added ethyl propiolate (1.2 ml, 12 mmol) and triethylamine (7 ml, 50 mmol). The resultant mixture was stirred under nitrogen at reflux over weekend. After cooled to room temperature it was poured into brine (100 ml), extracted with dichloromethame (3×100 ml), dried over magnesium sulfate and evaporated. Silica gel chromatography (hexanes/dichloromethane 9:1 to straight dichloromethane) gave Phenol, 4-[[1-[[3,5-bis(1,1-dimethylethyl)-4-ethoxyphenyl]thio]-1-methylethyl]thio]-2,6-bis(1,1-dimethylethyl)-; (0.51 g), 2-Propenoic acid, 3-[4-[[1-[[3,5-bis(1,1-dimethylethyl)-4-ethoxyphenyl]thio]-1-methylethyl]thio]-2,6-bis(1,1-dimethylethyl)phenoxy]-, ethyl ester, (E)-; (0.37 g) and 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, ethyl ester, (E)- (0.54 g).

Phenol, 4-[[1-[[3,5-bis(1,1-dimethylethyl)-4-ethoxyphenyl]thio]-1-methylethyl]thio]-2,6-bis(1,1-dimethylethyl)-

$^1$H-NMR (400 MHz, CDCl$_3$): 7.52 (s, 2 H), 7.45 (s, 2 H), 5.37 (s, 1 H), 3.76 (quad., 2 H), 1.39–1.45 (m, 45 H).

2-Propenoic acid, 3-[4-[[1-[[3,5-bis(1,1-dimethylethyl)-4-hydroxyphenyl]thio)-1-methylethyl]thio]-2,6-bis(1,1-dimethylethyl)phenoxy]-, ethyl ester, (E)-

$^1$H-NMR (400 MHz, CDCl$_3$): 7.62 (s, 2 H), 7.44 (s, 2 H), 6.40 (d, 1 H), 5.38 (s, 1 H), 5.02 (d, 1 H), 4.23 (quad., 2 H), 1.47 (s, 6 H), 1.44 (s, 18 H), 1.42 (s, 18 H), 1.30 (t, 3 H).

2-Propenoic acid, 3-[4-[[1-[[3,5-bis(1,1-dimethylethyl)-4ethoxyphenyl]thio]-1-methylethyl]thio]-2,6-bis(1,1-dimethylethyl)phenoxy]-, ethyl ester, (E)-

$^1$H-NMR (400 MHz, CDCl3): 7.62 (s, 2 H), 7.51 (s, 2 H), 6.40 (d, 1 H), 5.03 (d, 1 H), 4.23 (quad., 2 H), 3.76 (quad., 2 H), 1.25–1.48 (m, 48 H).

EXAMPLE 41

Butanedioic acid, mono[4-[[1-[[3,5-bis(1,1-dimethylethyl)-4-methoxyphenyl]thiol]1-methylethyl]thiol-2,6-bis(1,1-dimethylethyl)phenyl] ester Reaction Description The compound of Example 22 (1.13 g, 1.83 mmol) was taken up in DMF (3.6 mL) and 60% sodium hydride (183 mg, 4.6 mmol) was added followed 0.25 h later by methyl iodide (0.342 mL, 5.5 mmol). The reaction was allowed to stir overnight. The reaction was quenched with water (2 mL), diluted with ether (50 mL). The ether layer was washed with water (2×10 mL) and saturated aqueous sodium chloride (1×10 mL), dried over MgSO$_4$, filtere, and concentrated. Column chromatography over silica gel and elution with a concentration gradient of 0:100 ether/hexane to 40:60 ether/hexane gave 556 mg of dimethylated product. The product was taken up in THF:MeOH:H$_2$O (4:1:1)(5 mL) and lithium hydroxide (63 mg, 1.5 mmol) was added. After 2.5 h the reaction was complete and quenched with 1 N HCl (3 mL) and extracted with ethyl acetate (15 mL). The ethyl acetate solution was washed with saturated aqueous sodium chloride (3 mL), dried over MgSO$_4$, filtered and concentrated. Chromatography over silica gel, eluting with a solvent gradient of 10:90 ether/hexanes to 50:50 ether/hexanes afforded 400 mg of product. $^1$H NMR (CDCl$_3$, 400 MHZ): δ7.62 (s, 2 H), 7.45 (s, 2 H), 5.37 (s, 1 H), 3.71 (s, 3 H), 2.75 (t, J=7.2 Hz, 2 H), 2.55 (t, J=7.2 Hz, 2 H), 2.09 (m, 2 H), 1.46 (s, 6 H), 1.44 (s, 18 H), 1.42 (s, 18 H).

EXAMPLE 42

Phenol, 4-[[1-[[4-[2-[4-(dimethylamino)phenyl]ethoxy]-3,5-bis(1,1-dimethylethyl)phenyl]thio)-1-methylethyl]thio]-2,6-bis(1,1-dimethylethyl)-

Reaction Description

Probucol (1.16 mmol; 600 mg) was dissolved in THF (11.6 mL) and treated with triphenylphosphine (2.3 mmol; 608 mg), diethyl azodicarboxylate (2.3 mmol; 0.37 mL), and 4-(dimethylamino)phenethyl alcohol (2.3 mmol; 383 mg). The brown mixture was stirred under reflux for 41.5 h. Solvent was removed by rotary evaporation to give a brown oil. Purification by chromatography gave 4,4'-(isopropylidenedithio)[O-(4"-(dimethylamino)phenethyl)-2',6'-di-tert-butylphenol][2,6di-tert-butylphenol] as an oil (256 mg; 33% yield) $^1$H NMR (CDCl$_3$, 400 MHz): δ7.52 (s, 2 H), 7.45 (s, 2 H), 7.12 (d, J=8.4 Hz, 2 H), 6.74 (br d, J=8.0 Hz, 2 H), 5.38 (s, 1 H), 3.84 (app t, J=8.0, 8.8 Hz, 2 H), 3.09 (app t, J=7.6, 8.8 Hz, 2 H), 2.93 (s, 6 H), 1.45–1.44 (overlapping s, 42 H).

EXAMPLE 43

Benzenamine, 4,4'-[(1-methylethylidene)bis[thio[2,6-bis(1,1-dimethylethyl)-4,1-phenylene]oxy-2,1-ethanediyl)]]bis[N,N-dimethyl- Reaction Description Probucol (1.16 mmol; 600 mg) was dissolved in THF (11.6 mL) and treated with triphenylphosphine (2.3 mmol; 608 mg), diethyl azodicarboxylate (2.3 mmol; 0.37 mL), and 4-(dimethylamino)phenethyl alcohol (2.3 mmol; 383 mg). The brown mixture was stirred under reflux for 41.5 h. Solvent was removed by rotary evaporation to give a brown oil. Purification by chromatography gave 4,4'-(isopropylidenedithio)bis[(4"-(dimethylamino)phenethyl)-2,6-di-tert-butylphenol] as a light pink solid (155 mg; 16% yield) $^1$H NMR (CDCl$_3$, 400MHz): δ7.50 (s, 4 H), 7.12 (d, J=8.8 Hz, 4 H), 6.74 (br d, J=8.0 Hz, 4 H), 3.84 (app t, J=7.6, 8.8 Hz, 4 H), 3.09 (app t, J=8.0, 8.8 Hz, 4 H), 2.93 (s, 12 H), 1.43–1.42 (overlapping s, 42 H).

EXAMPLE 44

L-Arginine, mono[4-[[1-[[3,5-bis(1,1-dimethylethyl)-4-hydroxyphenyl]thio]-1-methylethyl]thio]-2,6-bis(1,1-dimethylethyl)phenyl butanedioate]

Reaction Description

To a solution of the compound of Example 22 (1.67 g, 2.7 mmol) in methanol (30 ml) was added L-arginine (0.47 g, 2.7 mmol). The resultant mixture was stirred at room temperature for 2 hours and then filtered. The filtrate was evaporated and the residue was dissolved in minimum amount of ether. Then hexanes was added to precipitate out the title compound. It was filtered and dried on vacuum to afford a off-white solid (1.75 g). MP: 185–190° C. $^1$H-NMR (400 MHz, CDCl3): 7.60 (s, 2 H), 7.42 (s, 2 H), 5.37 (s, 1 H), 3.64 (br. s, 1 H), 3.11 (br. s, 2 H), 2.96 (br. s, 2 H), 2.58 (br. s, 2 H), 1.41–1.44 (m, 26 H), 1.23–1.31 (m, 20 H).

EXAMPLE 45

2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, (E)-

To a solution of 2-Propenoic acid, 3-[4-[[1-[[3,5-bis(1,1-dimethylethyl)-4-hydroxyphenyl]thiol-1-methylethyl]thio]-2,6-bis(1,1-dimethylethyl)phenoxy]-, ethyl ester, (E)- (0.16 g, 0.26 mmol) in THF (5 ml) were added water (2 ml) and lithium hydroxide monohydrate (42 mg, 1 mmol). The resultant mixture was stirred at reflux overnight. After cooled to room temperature it was poured into dichloromethane (50 ml), washed with brine, dried over magnesium sulfate and evaporated. Silica gel chromatography (hexanes/ethyl acetate 4:1) gave the title compound as a viscous residue (22 mg). $^1$H-NMR (400 MHz, CDCl3): 7.63 (s, 2 H), 7.44 (s, 2 H), 6.52 (d, 1 H), 5.39 (s, 1 H), 5.08 (d, 1 H), 1.47 (s, 6 H), 1.44 (s, 18 H), 1.42 (s, 18 H).

EXAMPLE 46

α-D-Galactopyranose, 60-[4-[[1-[[3,5-bis(1,1-dimethylethyl)-4-hydroxyphenyl]thio]-1-methylethyl]thio]-2,6-bis(1,1-dimethylethyl)phenyl]-1,2:3,4-bis-O-(1-methylethylidene)

To a solution of probucol (2.58 g, 5 mmol) and 1,2,3,4-di-O-isopropylidene-D-galactopyranose (1.8 ml, 10 mmol) in THF (100 ML) were added triphenylphosphine (2.62 g, 10 mmol) and diethyl azodicarboxylate (1.57 ml, 10 mmol). The resultant mixture was stirred under nitrogen at reflux 72 hours. It was evaporated. Silica gel chromatography (cyclohexane/ethyl acetate 30:1) gave the title compound (0.16 g). $^1$H-NMR (400 MHz, CDCl3): 7.53 (s, 2 H), 7.45

(s, 2 H), 5.60 (s, 1 H), 4.65 (m, 2 H), 4.35 (m, 4 H), 1.59 (s, 6 H), 1.44 (s, 18 H), 1.43 (s, 18 H), 1.37 (s, 6 H), 1.33 (s, 6 H).

EXAMPLE 47

Phenol, 4-[[1-[[4-[3-(dimethylamino)propoxy]-3,5-bis(1,1-dimethylethyl)phenyl]thio]-1-methylethyl]thio]-2,6-bis(1,1-dimethylethyl)-

Reaction Description

Probucol (0.5 g, 0.97 mmol) was dissolved in THF, cooled to 0° C., and 3-hydroxypropyldiethyl amine (0.287 mL, 1.94 mmol) was added followed by the addition of triphenylphosphine (0.508 g, 1.94 mmol) and diethyl azodicarboxylate (0.31 mL, 1.94 mmol). The reaction was heated to reflux and reflux continued for 30 h. The reaction mixture was concentrated and purified by silica gel chromatography eluting with 20:80 methanol/ether to give the product. $^1$H NMR (CDCl$_3$, 400 MHz): δ7.52 (s, 2 H), 7.27 (s, 2 H), 3.74 (t, J=1.6 Hz, 2 H), 2.56 (q, J=7.2 Hz, 2 H), 2.03 (pent, J=7.6 Hz, 2 H), 1.44 (q, J=3.2 Hz, 4 H), 1.42 (s, 24 H), 1.25 (t, J=3.3 Hz, 6 H).

EXAMPLE 48

Glycine, N-[[4-[[1-[[3,5-bis(1,1-dimethylethyl)-4-hydroxyphenyl]thio]-1,methylethyl]thio]-2,6-bis(1,1-dimethylethyl)phenoxyl acetyl]-

Reaction Description

To Acetic acid, [4-[[1-3,5-bis(1,1-dimethylethyl)-4-hydrocyphenyl]thio]-1-methylethyl]thio]2,6-bis-(1,1-dimethylethylphenoxy)- (50 mg, 0.087 mmol) in methylene chloride (0.87 mL) was added glycine ethyl ester hydrochloride (15.8 mg, 0.11 mmol), 1-(3-dimethylaminopropyl-3-ethyl carbodiimide hydrochloride(22 mg, 0.11 mmol) and dimethylaminopyridine (28 mg, 0.23 mmol). The reaction mixture was stirred overnight and the methylene chloride evaporated. The reaction was diluted with ether (10 mL) and washed with water (2×3 mL), dried over MgSO$_4$, filtered, and concentrated. The crude mixture was purified by silica gel chromatography and elution with 50:50 ether/hexane to give 50 mg of the ethyl ester of the product. The ethyl ester dissolved in THF:H$_2$O: MeOH (2:1:1)(1 mL) and LiOH—H20 (15 mg) was added and the reaction stirred for 1 h. The reaction was neutralized with 1N HCl and extracted with ether (2×10 mL), dried over MgSO$_4$, filtered, and concentrated to give 25 mg of product. $^1$H NMR (CDCl$_3$, 400 MHz): δ7.56 (s, 2 H), 7.42 (s, 2 H), 5.39 (br s, 1 H), 4.31 (s, 2 H), 4.22 (d, J=5.2 Hz, 2 H), 1.44 (s, 6 H), 1.42 (s, 9 H), 1.39 (s, 9 H).

EXAMPLE 49

Glutamic acid, N-[[4-[[1-[[3,5-bis(1,1-dimethylethyl)-4-hydroxyphenyl]thio]-1-methylethyl]thio]-2,6-bis(1,1-dimethylethyl)phenoxy]acetyl]-

Reaction Description

To Acetic acid, [4-[[1-3,5-bis(1,1-dimethylethyl)-4-hydrocyphenyl]thio]-1-methylethyl]thio]2,6-bis-(1,1-dimethylethylphenoxy)- (100 mg, 0.174 mmol) in methylene chloride (1.8 mL) was added glutamic acid diethylester hydrochloride (54 mg, 0.22 mmol), 1-(3-dimethylaminopropyl-3-ethyl carbodiimide hydrochloride (44 mg, 0.22 mmol) and dimethylaminopyridine(55 mg, 0.45 mmol). The reaction mixture was stirred overnight and the methylene chloride evaporated. The reaction was diluted with ether(10 mL) and washed with water(2×3 mL), dried over MgSO$_4$, filtered, and concentrated. The crude mixture was purified by silica gel chromatography and elution with 50:50 ether/hexane to give 130 mg of the diethyl ester of the desired product. The diethyl ester was dissolved in THF:H$_2$O: MeOH(2:1:1)(3 mL) and LiOH—H$_2$O (100 mg) was added and the reaction stirred for 1 h. The reaction was neutralized with 1 N HCl and extracted with ether (2×10 mL), dried over MgSO$_4$, filtered, and concentrated to give 45 mg of product. $^1$H NMR (CDCl$_3$, 400 MHz): δ7.57 (s, 2 H), 7.42 (s, 2 H), 5.37 (s, 1 H), 4.83 (m, 1 H), 4.28 (s, 2 H), 2.56 (m, 2 H), 1.44 (s, 6 H), 1.43 (s, 9 H), 1.41 (s, 9 H).

EXAMPLE 50

L-Glutamic acid, N-[3-[4-[[1-[[3,5-bis(1,1-dimethylethyl)-4hydroxyphenyl]thio]-1-methylethyl]thio]-2,6-bis(1,1-dimethylethyl)phenoxy]-2-hydroxypropyl]-di-, diethyl ester Reaction Description To a suspension of Phenol, 4-[[1-[[3,5-bis(1,1-dimethylethyl)-4-(oxiranylmethoxy)phenyl]thio]-1-methylethyl]thio]-2,6-bis(1,1-dimethylethyl)- (0.12 g, 0.20 mmol) and L-glutamic acid diethyl ester hydrochloride (0.24 g, 1 mmol) in ethanol (15 ml) was added triethylamine (2 ml). The resultant mixture was stirred under nitrogen at reflux for 18 hours. It was evaporated. Silica gel chromatography (dichloromethane/methanol 5:1) gave a yellow oil which was re-columned (dichloromethane/methanol 10:1) to give the title compound as a white viscous residue (16 mg). $^1$H-NMR (400 MHz, CDCl$_3$): 7.53 (s, 2 H), 7.42 (s, 2 H), 5.36 (s, 1 H), 4.90 (m, 1 H), 3.85 (m, 2 H), 3.55–3.75 (m, 7H), 2.01 (m, 2 H), 1.39–1.42 (m, 48 H), 1.23 (m, 2 H).

EXAMPLE 51

2-Propenoic acid, 4-[4-[[1-[[3,5-bis(1,1-dimethylethyl)-4-hydroxyphenyl]thio]-1-methylethyl]thio]-2,6-bis(1,1-dimethylethyl)phenoxy]butyl ester To a solution of probucol (2.58 g, 5 mmol) in THF (50 ML) were added 4-hydroxybutyl acrylate (1.0 ml, 10 mmol), triphenylphosphine (2.62 g, 10 mmol) and diethyl azodicarboxylate (1.57 ml, 10 mmol). The resultant mixture was stirred under nitrogen at reflux over weekend. It was evaporated. Silica gel chromatography (hexanes/dichloromethane 4:1) gave the title compound as a brown oil (0.92 g). $^1$H-NMR (400 MHz, CDCl$_3$): 7.54 (s, 2 H), 7.46 (s, 2 H), 6.42 (dd, 1 H), 6.14 (dd, 1 H), 5.84 (dd, 1 H), 5.38 (s, 1 H), 4.23 (t, 2 H), 3.75 (t, 2 H), 1.97 (m, 2 H), 1.82 (m, 2 H), 1.46 (s, 6 H), 1.45 (s, 18 H), 1.42 (s, 18 H).

EXAMPLE 52

Phenol, 4-[[1-[[3,5-bis(1,1-dimethylethyl)-4 (4hydroxybutoxy)phenyl]thio]-1-methylethyl]thio]-2,6-bis(1,1-dimethylethyl)-

To a suspension of 2-Propenoic acid, 4-[4-[[1-[[3,5-bis(1,1-dimethylethyl)-4-hydroxyphenyl]thio]-1-methylethyl]thio]-2,6-bis(1,1-dimethylethyl)phenoxy]butyl ester (0.82 g) in methanol (20 ml) was added potassium carbonate (0.5 g). The resultant mixture was stirred under nitrogen at room temperature overnight. It was poured into water (50 ml), extracted with dichloromethane (2×50 ml), dried over magnesium fulfate and evaporated. Silica gel chromatography (hexanes/ethyl acetate 4:1) gave the title compound as a colorless oil (0.52 g). $^1$H-NMR (400 MHz, CDCl$_3$): 7.54 (s, 2 H), 7.46 (s, 2 H), 3.71–3.77 (m, 4 H), 1.96 (m, 2 H), 1.72 (m, 2 H), 1.46 (s, 6 H), 1.45 (s, 18 H), 1.43 (s, 18 H).

EXAMPLE 53

β-D-Glucopyranose, 6-O-[[1-[[3,5-bis(1,1-dimethylethyl)-4-hydroxyphenyl]thio]-1-methylethyl]thio]-2,6-bis(1,1-dimethylethyl)phenyl]-

To a solution of probucol (1.8 g, 3.5 mmol) in THF (20 ML) were added 1,2,3,4-tetra-O-actyl-β-D-glucopyranose (1.0 g, 2.9 mmol), triphenylphosphine (0.92 g, 3.5 mmol) and diethyl azodicarboxylate (0.55 ml, 3.5 mmol). The resultant mixture was stirred under nitrogen at reflux for two hours. It was evaporated. Silica gel chromatography (hexanes/ethyl acetate 4:1) gave the title compound as an off-white solid (0.92 g). $^1$H-NMR (400 MHz, CDCl3): 7.53 (s, 2 H), 7.45 (s, 2 H), 5.80 (d, 1 H), 5.38 (s, 1 H), 5.33 (dd, 1 H), 5.16 (dd, 1 H), 4.90 (dd, 1 H), 4.19 (m, 1 H), 3.88 (m, 1 H), 3.74 (m, 1 H), 2.14 (s, 3 H), 2.06 (s, 3 H), 2.03 (s, 3 H), 2.02 (s, 3 H), 1.45 (s, 18+6 H), 1.38 (s, 18 H).

EXAMPLE 54

1-H-Tetrazole-1-butanoic acid, 4-[[1-[[3,5-bis(1,1-dimethylethyl)-4-hydroxyphenyl]thio]-1-methylethyl]thio]-2,6-bis(1,1-dimethylethyl)phenyl ester To a solution of Butanoic acid, 4-hydorxy-, 4-[[1-[[3,5-bis(1,1-dimethylethyl)-4-hydroxyphenyl]thio]-1-methylethyl]thio]-2,6-bis(1,1-dimethylethyl)phenyl ester (60 mg, 0.1 mmol) in THF (10 ML) were added 1H-tetrazole 14 mg, 0.2 mmol), triphenylphosphine (52 mg, 0.2 mmol) and diethyl azodicarboxylate (0.03 ml, 0.2 mmol). The resultant mixture was stirred under nitrogen at reflux for 2 hours. It was evaporated. Silica gel chromatography (hexanes/ethyl acetate 4:1) gave the title compound as an oil (57 mg). $^1$H-NMR (400 MHz, CDCl$_3$): 8.56 (s, 1 H), 7.64 (s, 2 H), 7.45 (s, 2 H), 5.39 (s, 1 H), 4.84 (t, 2 H), 2.74 (t, 2 H), 2.47 (m, 2 H), 1.47 (s, 6 H), 1.45 (s, 18 H), 1.33 (s, 18 H).

EXAMPLE 55

Phenol, 4-[[1-[[3,5-bis(1,1-dimethylethyl)-4-[[3-hydroxy-1-propenyl)oxy]phenyl]thio]-1-methylethyl]thio]-2,6-bis(1,1-dimethylethyl)-

To a solution of 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, ethyl ester, (E)- (65 mg, 0.1 mmol) in THF (15 ml) was added lithium aluminum hydride (1 ml, 1 M solution in THF). The resultant mixture was stirred under nitrogen at room temperature overnight. Saturated ammonium chloride solution (20 ml) was added and the mixture was stirred for 0.5 hour. It was extracted with dichloromethane (3×50 ml) and the organic phase was dried over magnesium sulfate and evaporated. Silica gel chromatography (hexanes/ethyl acetate 4:1) gave the title compound as an oil (46 mg). $^1$H-NMR (400 MHz, CDCl3): 7.61 (s, 2 H), 7.45 (s, 2 H), 5.99 (d, 1 H), 5.39 (s, 1 H), 4.84 (m, 1 H), 4.46 (m, 2 H), 1.47 (s, 6 H), 1.45 (s, 18 H), 1.42

EXAMPLE 56

L-Lysine, N$^6$-[[4-[[3,5-bis(1,1-dimethylethyl)-4-hydroxyphenyl]thio]-1-methylethyl]thio]-2,6-bis(1,1-dimethylethyl)phenoxy]acetyl]-

Reaction Description

To Acetic acid, [4-[[1-[[3,5-bis(1,1-dimethylethyl)-4-hydroxyphenyl]thio]-1-methylethyl]thio]2,6-bis(1,1-dimethylethyl)phenoxy]- (150 mg, 0.26 mmol) in methylene chloride (1.8 mL) was added lysine methyl ester hydrochloride (79 mg, 0.34 mmol), 1-(3-dimethylaminopropyl-3-ethyl carbodiimide hydrochloride(130 mg, 0.67 mmol) and dimethylaminopyridine(82 mg, 0.67 mmol). The reaction mixture was stirred overnight and the methylene chloride evaporated. The reaction was diluted with ether(10 mL) and washed with water(2×3 mL), dried over MgSO$_4$, filtered, and concentrated. The crude mixture was purified by silica gel chromatography and elution with 50:50 ether/hexane followed by 70:30 ether/hexane to give 128 mg of the methyl ester of product. The methyl ester was dissolved in THF:H$_2$O: MeOH(2:1:1)(3 mL) and LiOH—H$_2$O (50 mg) was added and the reaction stirred for 1 h. The reaction was concentrated and purified over silica gel eluting with 20:80 methanol/hexane to give 67 mg of product. 7.58 (s, 2 H), 7.44 (s, 2 H), 6.86 (m, 1 H), 5.39 (s, 1 H), 4.75 (m, 1 H), 4.29 (d, J=7.2 Hz, 2 H), 3.44 (m, 2 H), 2.10 (m, 2 H), 1.95 (m, 2 H), 1.82 (m, 2 H), 1.46 (s, 6 H), 1.44 (s, 9 H), 1.42 (s, 9 H).

EXAMPLE 57

D-Glucopyranose, 6-O-[4-[[1-[[3,5-bis(1,1-dimethylethyl)-4-hydroxyphenyl]thio]-1-methylethyl]thio]-2,6-bis(1,1-dimethylethyl)phenyl]-

To a suspension of β-D-Glucopyranose, 6-O-[4-[[1-[[3,5-bis(1,1-dimethylethyl)-4-hydroxyphenyl]thio]-1-methylethyl]thio]-2,6-bis(1,1-dimethylethyl)phenyl]- (0.68 g) in methanol (50 ml) was added potassium carbonate (1 g) and the mixture was stirred under nitrogen at room temperature overnight. It was poured into water (200 ml), extracted with ethyl acetate (3×150 ml), washed with brine (100 ml), dried over magnesium and evaporated. Silica gel chromatography (dichloromethane/methanol 10:1 to 5:1) gave the title compound as an off-white solid (0.26 g). $^1$H-NMR (400 MHz, CDCl$_3$): 7.52 (s, 2 H), 7.44 (s, 2 H), 5.36 (s, 1 H), 5.31 (s) and 4.78 (br. s, 1 H), 3.30–4.38 (br. m, 6 H), 1.38–1.43 (m, 42 H).

EXAMPLE 58

D-Glucitol, 6-O-[4-[[1-[[3,5-bis(1,1-dimethylethyl)-4-hydroxyphenyl]thio]-1-methylethyl]thio]-2,6-bis(1,1-dimethylethyl)phenyl]-

To a solution of D-Glucopyranose, 6—O-[4-[[1-[[3,5-bis(1,1-dimethylethyl)-4-hydroxyphenyl]thio]-1-methylethyl]thio]-2,6-bis(1,1-dimethylethyl)phenyl]- (70 mg) in THF (5 ml) was added sodium borohydride and the mixture was stirred under nitrogen at room temperature for 2 hours. Then saturated ammonium chloride (2 ml) was added and the mixture stirred for another hour. It was poured into water (50 ml) and extracted with dichloromethane (3×50 ml). The organic phase was dried over magnesium and evaporated. Silica gel chromatography (dichloromethane/methanol 100:12) gave the title compound as a white solid (19 mg). $^1$H-NMR (400 MHz, CDCl$_3$): 7.54 (s, 2 H), 7.44 (s, 2 H), 5.36 (s, 1 H), 4.35 (m 1 H), 3.30–4.10 (m, 7 H), 1.40–1.44 (m, 42 H).

EXAMPLE 59

Butanoic acid, 4-[[hydroxy(2-hydroxyphenoxy) phosphinyl]oxy]-4-[[1-[[3,5-bis(1,1-dimethylethyl)-4-hydroxyphenyl]thio]-1-methylethyl]thio]-2,6-bis (1,1-dimethylethyl)phenyl ester To a solution of Butanoic acid, 4-hydorxy-, 4-[[1-[[3,5-bis(1,1-dimethylethyl)-4-hydroxyphenyl]thio]-1- methylethyl]thio]-2,6-bis(1,1-dimethylethyl)phenyl ester (60 mg, 0.1 mmol) in pyridine (1 ml) was added 1,2-phenylene phosphorochloridate (21 mg, 0.11 mmol) and the mixture was stirred under nitrogen at room temperature for 1 hour. It was evaporated and the residue was dissolved in dichloromethane (10 ml). Water (1 ml) and acetic acid (0.5 ml) were added and the mixture was stirred for 0.5 hour. It was poured into water (50 ml) and extracted with dichloromethane (2×50 ml). The organic phase was dried over magnesium and evaporated. Silica gel chromatography (dichloromethane/methanol 5:1) gave the title compound as a white solid (21 mg). $^1$H-NMR (400 MHz, CDCl$_3$): 7.58 (s, 2 H), 7.44 (s, 2 H), 7.15 (br. s, 1 H), 6.87 (br. s, 2 H), 6.71 (br. s, 1 H), 5.37 (s, 1 H), 3.97 (br. s, 2 H), 2.48 (br. s, 2 H), 1.83 (br. s, 2 H), 1.45 (s, 6 H), 1.43 (s, 18 H), 1.24 (s, 18 H).

EXAMPLE 60

Butanoic acid, 4-hydroxy-3,3-dimethyl-, 4-[[1-[[3,5-bis(1,1-dimethylethyl)-4-hydroxyphenyl]thio]-1-methylethyl]thio]-2,6-bis(1,1-dimethylethyl)phenyl ester Reaction Description To a flask was added probucol (2.3 g, 4.46 mmol) and tetrahydrofuran (23 mL). To the solution was added 60% sodium hydride in mineral oil (0.23 g, 5.75 mmol). to the cloudy white mixture was added 2,2 dimethyl succinic anhydride (1 g, 7.6 mmol). The reaction was stirred at room temperature for 3 h. The dark purple reaction mixture was made acidic with 1N HCl (25 mL) and extracted twice with ethyl acetate (50 mL). The organic extracts were dried over MgSO$_4$, filtered and concentrated. The crude product mixture was dissolved in ether and chromatographed on silica gel with a concentration gradient of 70:30 hexane/ether to 0:100 hexane/ether. The appropriate fractions were combined and concentrated affording 700 mg of a white solid. The white solid (214 mg, 0.332 mmol)) was taken up in THF (6 mL) and borane-dimethylsulfide (2M in THF, 0.665 mL, 0.664 mmol) was added and the reaction stirred for 6 h. The reaction was quenched with concentrated HCl (0.100 mL) and the reaction stirred overnight. The reaction was diluted with ether (25 mL), washed with water(×5 mL), NaHCO$_3$ (1×5 mL), and brine (1×5 mL). The ether layer was dried over MgSO$_4$, filtered, and concentrated. Radial silica gel chromatography and elution with a concentration gradient from 100:0 hexane/ether to 50:50 hexane/ether gave 85 mg of product. $^1$H NMR (CDCl$_3$, 400 MHz): δ7.64 (s, 2 H), 7.46 (s, 2 H), 5.39 (s, 1 H), 3.48 (d, J=6.8 Hz, 2 H), 2.73 (s, 2 H), 1.47 (s, 6 H), 1.45 (s, 9 H), 1.35 (s, 9 H), 1.11 (s, 6 H).

EXAMPLE 61

Butanoic acid, 4-(sulfoxy)-, 1-[4-[[3,5-bis(1,1-dimethylethyl)-4-hydroxyphenyl]thio]-1-methylethyl]thio]-2,6-bis(1,1-dimethylethyl)phenyl] ester Reaction Butanoic acid, 4-hydorxy-, 4-[[1-[[3,5-bis(1,1-dimethylethyl)-4-hydroxyphenyl]thio]-1-methylethyl]thio]-2,6-bis(1,1-dimethylethyl)phenyl ester (12.5 g, 20.75 mmol) was dissolved in DMF (150 ml) and sulfur trioxide trimethylamine complex (12.5 g, 87.5 mmol) was added. The mixture was stirred at room temperature overnight. It was evaporated and the residue was dissolved in dichloromethane (100 ml), washed with water (2×50 ml). The aqueous phase was extracted with dichloromethane (75 ml). The combined organic phase was dried over magnesium sulfate and evaporated. Silica gel chromatography (dichloromethane/methanol 10:1, 5:1) gave a residue which was used for the next step of reaction.

The above product was dissolved in THF (200 ml). NaOH (0.8 g, 20 mmol) in water (5 ml) was added. The mixture was stirred at room temperature for 2 h and then evaporated. 1 N NaOH solution (200 ml) was added to the residue and stirred for 0.5 h. It was filtered and a yellowish solid was collected, which was dried to a constant weight (9.23 g).

The present invention also includes the use of compounds of the formulas (I) and (II) in inhibiting the peroxidation of LDL lipid and in inhibiting the progression of atherosclerosis in patients in need thereof.

As used herein, the term "patient" refers to warm-blooded animals or mammals, and in particular humans, who are in need of the therapy described herein.

The following examples illustrate the use of compounds of formula (I) according to the present invention. These examples are illustrative only and are not intended to limit the scope of the invention in any way.

EXAMPLE 62

Lipid Screen & IC$_{50}$ Determination Protocol

Preparation of HEPG2

HEPG2 cell was started in 10 ml of MEM, 10% FBS, 1 mM Sodium Pyruvate. The cells were incubated in a tissue culture incubator. The cells were split into 4×96-wells plate in MEM, 10% FBS, 1 mM Sodium Pyruvate and allowed to grow to about 50% confluency and then removed.

Day 1 Treatment

The cells were treated with the desired concentration of compounds in 100 μl DMEM, 1% RSA for 24 hours. The compounds are dissolved in DMSO. For IC$_{50}$, the range of concentration is 10 uM–40 uM, with each concentration being done in triples.

On the same day, 4×96-wells NuncImmunoSorb plate is coated with 100 μl of mouse anti-human ApoB monoclonal 1D1 (1:1000 dilution in 1×PBS, pH 7.4). The coating is allowed overnight.

Day 2 ApoB ELISA

The coated plate is washed 3 times with 1×PBS, pH 7.4, –0.05% Tween 20. 100 μl of the standards is added to the selected wells. ApoB standards are prepared at 6.25, 3.12, 1.56, 0.78, 0.39 ng, and each concentration is done in triplicates. For samples:

90 μl of 1×PBS, pH 7.4, –0.05% Tween 20 is added to each well corresponding to the sample. 10 μl of media is transferred from the treated HEPG2 plates to the ApoB ELISA plate. The plate is incubated at room temperature for 2 hours, rocking gently.

Wash the coated plate 3× with 1×PBS, pH 7.4, –0.05% Tween 20. Add 100 μl of sheep anti-human ApoB polyclonal from Boehringer Mannheim. (1:2000 dilution in 1×PBS, pH 7.4, –0.05% Tween 20) from Boehringer Mannheim. Incubate at room temperature for 1 hour, rocking gently. Wash the coated plate 3× with 1×PBS, pH 7.4, –0.05% Tween 20. Add 100 μl of rabbit anti-sheep IgG (1:2000 dilution in 1×PBS, pH 7.4, –0.05% Tween 20). Incubate at room temperature for 1 hour, rocking gently. Wash the coated plate 3× with 1×PBS, pH 7.4, –0.05% Tween 20. Add 100 μl of substrate (10 ml of distilled water, 100 μl of TMB (10 mg/ml), and 1 μl of hydrogen peroxide). Allow color to emerge and stop reaction with 25 ul of 8N sulfuric acid. Wells are read with MicroPlate Reader @ 450 nM. Graph accumulation of ApoB in media as a percentage of control for each sample and their concentration. A determination of $IC_{50}$ is obtained from the graph.

EXAMPLE 63

VCAM-1 Assay

Splitting the cells

Two to four confluent P150 plates are trypsinized and the cells transferred to a 50 mL conical centrifuge tube. The cells are pelleted, resuspended, and counted using the trypan blue exclusion method.

Cells are resuspended at a concentration of 36,000 cells/mL and 1 mL is aliquoted per well.

Cells are split into 24 well tissue culture plates. The cells in each well should be approximately 90–95% confluent by the following day. Cells should not be older than passage 8.

Preparation of Compounds

Water Soluble Compounds

Compounds are initially screened at 50 $\mu$M and 10 $\mu$M. A 50 mM stock solution for each compound is prepared in culture medium. The stock solution is diluted to 5 mM and 1 mM. When 10 $\mu$L of the 5 mM solution is added to the well (1 mL medium/well), the final concentration will be 50 $\mu$M. Adding 10 $\mu$L of the 1 mM solution to the well will give a final concentration of 10 $\mu$M.

Water Insoluble Compounds

Compounds which will not go into solution in culture medium are resuspended in DMSO at a concentration of 25 mM. The stock solution is then diluted to the final concentration in culture medium. The old medium is aspirated and 1 mL of the new medium with the compound is added. For example, if the final concentration is 50 $\mu$M, the 2 $\mu$L of the 25 mM stock is added per mL of culture medium. The 50 mM solution is diluted for lower concentrations.

Adding the Compounds

The compounds are added to the plate (each compound is done in duplicate). One plate is done for VCAM expression and one plate is done for ICAM expression.

Immediately after the compounds are added, TNF is added to each well. 100 units/mL TNF is usually added to each well. Since each lot of TNF varies in the number of units, each new lot is titrated to determine the optimum concentration. Therefore this concentration will change. If 100 units/mL is bing used, dilute the TNF to 10 units/$\mu$L and add 10 $\mu$L to each well.

The plates are incubated at 37° C., 5% $CO_2$ overnight (approximately 16 hours). The next day the plates are checked under the microscope to see if there are any visual signs of toxicity. Records are made of any cell death, debris, or morphology changes, as well as insoluble compounds (particulate or turbity).

EXAMPLE 64

ELISA Assay

In order to assess MCP-1, the media (500 $\mu$L) is saved and frozen at −70° C. Wash cells once with roughly 1 ml/well of Hanks Balance Salt Solution (HBSS) or PBS. Gently empty the wash solution and then tap the plate onto paper towels. Add either 250 $\mu$L/well of HBSS +5% FCCS to the plank (no primary antibody wells) or 250 $\mu$L/well of primary antibody diluted in HBSS +5% FCS. Incubate for 30 minutes at 37° C. Wash the wells twice with 0.5 mL/well HBSS or PBS and gently tap the plates onto paper towels after the last wash. Add 250 $\mu$L/well of HRP-conjugated second antibody diluted in HBSS +5% FCS to every well including the blank wells (no primary antibody). Incubate at 37° C. for 30 minutes. Wash the wells four times with 0.5 mL/well HBSS or PBS and gently tap the plates onto paper towels after the last wash. Add 250 $\mu$L/well of substrate solution. Incubate at room temperature in the dark until there is adequate color development (blue). Note the length of time incubation was performed (typically 15–30 minutes). Add 75 $\mu$L/well stopper solution (8N sulfuric acid), and read A450 nm.

| Antibodies and solutions |
| --- |
| 1. Substrate solution is made immediately prior to use and contains:<br>    water                                                                          10 mL<br>    30% hydrogen peroxide                               1 $\mu$L<br>    TMB (3,3',5,5'-tetramethylbenzidine)           100 $\mu$L<br>TMB stock solution: To 10 mg TMB, add 1 mL acetone. Store at 4° C. protected from light.<br>2.   VCAM-1 Ab: stock .1 $\mu$g/$\mu$L                 final concentration 0.25 $\mu$g/mL<br>mix 25 $\mu$L stock VCAM-1 (Southern Biotechnology) and 10 mL HBSS + 5% FCS<br>3.   ICAM-1 Ab: stock .1 $\mu$g/$\mu$L                  final concentration 0.25 $\mu$g/mL<br>mix 25 $\mu$L stock ICAM-1 (Southern Biotechnology) and 10 mL HBSS + 5% FCS<br>4.   Secondary Ab: HRP-conjugated goat antimouse IgG diluted 1:500<br>mix 20 $\mu$L stock (Southern Biotechnology) and 10 mL HBSS + 5% FCS |

The degree of inhibition of the compounds of formulas (I) and (II) was determined by the assays described in Examples 62–64. The results are provided in Table 1.

TABLE 1

| Compound | VCAM-1 IC$_{50}$ or % inhibition at [µM] | LD$_{50}$ | ApoB/HepG2 IC$_{50}$ or % inhibition at [µM] |
|---|---|---|---|
| 2,6-di-tert-butyl-4-thio(4'(methyl)phenylacetic acid))phenol | 80 | 200 | 7% at 15 |
| 2,6-di-tert-butyl-4-thio(4'-nitrobenzyl)phenol | 10 | 200 | 27 |
| 2,6-di-tert-butyl-4-thio(4'-nitrophenethyl)phenol | 15 | 0.4 | NE |
| 2,6-di-tert-butyl-4-thio(butanoic acid)phenol | 75 | 200 | NE |
| 2,6-di-tert-butyl-4-thio(3',5'-ditert-butyl,4'-hydroxy butanedioic acid ester)phenol | 6 | 50 | NE |
| 2,6-di-tert-butyl-4-thio(4'(methyl)benzoic acid)phenol | NE | >100 | NE |
| 2,6-di-tert-butyl-4-thio(2'-acetoxy,2'-methylpropyl)phenol | 50 | | NE |
| 2,6-di-tert-butyl-4-thio(3'-nitrobenzyl)phenol | 13 | 200 | 20 |
| 2,6-di-tert-butyl-4-thio(2',4'-dinitrobenzyl)phenol | 8 | 400 | 32 |
| (2,6-di-tert-butyl-4-thio(4'-trifluoromethyl)benzyl)phenol | 5 | 300 | 16 |
| 2,6-di-tert-butyl-4-thio((2'-furancarboxylic acid)-5-methyl)phenol | 40 | 400 | NE |
| 2,6-di-tert-butyl-4-thio(4'-methyl-N,N-dimethylbenzenesulfonamide)phenol | 20 | 350 | 31 |
| 2,6-di-tert-butyl-4-sulfinyl(4'-nitrobenzyl)phenol | 50 | <100 | NE |
| 2,6-di-tert-butyl-4-(sulfonyl-(4'-nitrobenzyl))phenol | 40 | 100 | 25 |
| 2,6-di-tert-butyl-4-thio(4'-acetoxybenzyl)phenol | 18 | 75 | 40 |
| 2,6-di-tert-butyl-4-thio(4'-methylbenzyl)phenol | 75 | | 22 |
| 2,6-di-tert-butyl-4-thio(4'-fluorobenzyl)phenol | 35 | | 30 |
| 2,6-di-tert-butyl-4-thio(3'-propanesulfonic acid)phenol | 25% at 50 | | |
| 2,6-di-tert-butyl-4-thio(5'-methyl-2'-((dimethylamino)methyl)furan)phenol | 10 | | 19 |
| 2,6-di-tert-butyl-4-thio(3'-(dimethylamino)propyl))phenol | 30% at 50 | 100 | |
| 2,6-di-tert-butyl-4-thio((1'-(acetoxy))pentyl)phenol | 40% at 50 | 100 | 30 |
| 2,6-di-tert-butyl-1-methoxy-4-thio(4'-trifluoromethyl)benzyl)benzene | NE | | <10 |
| 2,6-di-tert-butyl-4-thio(4'-(methyl)phenylethyl alcohol))phenol | 15 | 50 | 53% at 15 |
| Phenol, 4-[[1-[3,5-bis(1,1-dimethylethyl)4-[(4-nitrophenyl)methoxy] | 30% at 50 | >100 | 17% at 15 |

TABLE 1-continued

| Compound | VCAM-1 IC$_{50}$ or % inhibition at [μM] | LD$_{50}$ | ApoB/HepG2 IC$_{50}$ or % inhibition at [μM] |
|---|---|---|---|
| phenyl]thio]-1-methylethyl]thio]2,6-bis(1,1-dimethylethyl)- | 5.6 | 23 | 65% at 15 |
| Butanedioic acid, mono [4-[[1-[[3,5-bis(1,1-dimethylethyl)-4-hydroxyphenyl]thio]-1-methylethyl]thio]2,6-bis(1,1-dimethylethyl)phenyl] ester | | | |
| 2-Furancarboxylic acid, 5-nitro-,4-[[1-[[3,5-bis(1,1-dimethylethyl)-4-hydroxyphenyl]thio]-1-methylethyl]thio]-2,6-bis(1,1-dimethylethyl)phenyl ester | 25 | 400 | 17% at 15 |
| Butanoic acid, 4-[4-[[1-[[3,5-bis(1,1-dimethylethyl)-4-hydroxyphenyl]thio]-1-methylethyl]thio]2,6-dimethylphenoxy]- | 19 | 75 | 41% at 15 |
| Phenol, 4-[[1-[[4-(4-aminobutoxy)-3,5-bis(1,1-dimethylethyl)phenyl]thio]-1-methylethyl]thio]2,6-bis(1,1-dimethylethyl)- | 8 | 25 | |
| Phenol, 4-[[1-[[4-(4-aminobutoxy)-3,5-bis(1,1-dimethylethyl)phenyl]thio]-1-methylethyl]thio]2,6-bis(1,1-dimethylethyl)- | 9 | 25 | |
| Butanoic acid, 4-hydorxy-, 4-[[1-[[3,5-bis(1,1-dimethylethyl)-4-hydroxyphenyl]thio]-1-methylethyl]thio]-2,6-bis(1,1-dimethylethyl)phenyl ester | 6 | 250 | 81% at 15 |
| Propanaic acid, 2,2-dimethyl-,[4-[[1-[[3,5-bis(1,1-dimethylethyl)-4-hydroxyphenyl]thio]-1-methylethyl]thio]-2,6-bis(1,1-dimethylethyl)phenoxy] methyl ester | 25% at 25 | | |
| Phenol,4-[[1-[[4-(4-aminobutoxy)phenyl]thio]-1-methylethyl]thio]-2,6-bis(1,1-dimethylethyl) | 5 | 12.5 | |
| Butanoic acid,4-[4-[[1-[[3,5-bis(1,1-dimethylethyl)-4-hydroxyphenyl]thio]-1-methylethyl]thio] phenoxy]- | 19 | >100 | 47% at 15 |
| Acetic acid,[4-[[1-[[3,5-bis(1,1-dimethylethyl)-4-hydroxyphenyl]thio]-1-methylethyl]thio]2,6-bis(1,1-dimethylethyl)phenoxy] | 10 | 50 | NE |
| Butanoic acid, 4-amino-4-oxo-,4-[[1-[[3,5-bis(1,1-dimethylethyl)-4-hydroxyphenyl]thio]-1-methylethyl]thio]-2,6-bis(1,1-dimethylethyl)phenyl ester | 8 | 25 | |
| Glycine, 4-[[1-[[3,5-bis(1,1-dimethylethyl)-4-hydroxyphenyl]thio]-1-methylethyl]thio]-2,6-dimethylphenyl ester | 10% at 20 | 35 | |
| Butanedioic acid, mono[4-[[1-[[3,5-bis(1,1-dimethylethyl)-4-hydroxyphenyl]thio)-1- | 8 | 20 | |

TABLE 1-continued

| Compound | VCAM-1 IC$_{50}$ or % inhibition at [μM] | LD$_{50}$ | ApoB/HepG2 IC$_{50}$ or % inhibition at [μM] |
|---|---|---|---|
| methylethyl}-2,6-dimethyiphenyl]ester | | | |
| Butanedioic acid, mono[4-[[1-[[3,5-bis(1,1-dimethylethyl)-4-hydroxyphenyl]thio)-1-methylethyl}thio-2,6-bis(1,1-dimethylethyl)phenyl methyl ester | 40% at 100 | | |
| Glycine, 4-[[1-[[3,5-bis(1,1-dimethylethyl)-4-hydroxyphenyl]-1-methylethyl]thio]-2,6-bis(1,1-dimethylethyl)phenyl ester | 5 | 25 | 30% at 5 |
| Pentanedioic acid, (1-methylethylidene)bis(thio{2,6-bis(1,1-dimethylethyl)-4,1-phenylene)]ester | NE | 25 | |
| Pentanedioic acid, mono[4-[[1-[[3,5-bis(1,1-dimethylethyl)-4-hydroxyphenyl]thio]-1-methylethyl]thio]-2,6-bis(1,1-dimethylethyl)phenyl] ester | 8.7 | 25 | 70% at 15 |
| Butanoic acid, 4-[4-[[1-[[3,5-bis(1,1-dimethylethyl)-4-hydroxyphenyl]thio]-1-methylethyl]thio]-2,6-bis(1,1-dimethylethyl)phenoxy]- | 11 | 25 | 77% at 15 |
| Butanedioic acid, (1-methylethylidine)bis[thio[2,6-bi(1,1-dimethylethyl)-4,1-phenylene}}ester, | NE | 25 | |
| Glycine, (1-methylethylidene)bis[bis [thio2,6-bis (1,1-dimethylthyl)-4,1-phenylene]]ester, dihydrochloride | NE | | |
| Oxiranemethanol, a-[[4-[[1-[[3,5-bis(1,1-dimethylethyl)-4-hydroxyphenyl]thio]-1-methylethyl]thio]-2,6-bis(1,1-dimethylethyl)phenoxy]methyl]-; | 45 | | |
| Oxiranemethanol, 3-[[4-[[1-[[3,5-bis(1,1-dimethylethyl)-4-hydroxyphenyl]thio]-1-methylethyl]thio]-2,6-bis(1,1-dimethylethyl)phenoxy]methyl]-; | >100 | | NE |
| Oxiranemethanol, a-[[[3-[[4-[[1-[[3,5-bis(1,1-dimethylethyl)-4-hydroxyphenyl]thio]-1-methylethyl]thio]-2,6-bis(1,1-dimethylethyl)phenoxy]methyl]oxiranyl]methoxy]methyl]- | 60 | | |
| Phenol, 4-[[1-[[3,5-bis(1,1-dimethylethyl)-4-(oxiranylmethoxy)phenyl]thio]-1-methylethyl]thio]-2,6-bis(1,1-dimethylethyl)- | NE at 50 | | |
| Glycine,N-[3-[4-[[1-[[3,5-bis(1,1-dimethylethyl)-4-hydroxyphenyl]thio]-1-methylethyl]thio]-2,6-bis(1,1-dimethylethyl)phenoxy] | 16 | 50 | 45% at 15 |

TABLE 1-continued

| Compound | VCAM-1 IC$_{50}$ or % inhibition at [μM] | LD$_{50}$ | ApoB/HepG2 IC$_{50}$ or % inhibition at [μM] |
|---|---|---|---|
| 1,2,3-Butanetriol, 4-[4-[[1-[[3,5-bis(1,1-dimethylethyl)-4-hydroxyphenyl]thio]-1-methylethyl]thio]-2,6-bis(1,1-dimethylethyl)phenoxy]-2-hydroxypropyl]- | 6 | 20 | 6% at 1 |
| Phenol, 4-[[1-[[3,5-bis(1,1-dimethylethyl)-4-(3-ethoxy-2-hydroxypropoxy)phenyl]thio]-1-methylethyl]thio]-2,6-bis(1,1-dimethylethyl)-; | 75 | | |
| 1,2-Propanediol, 3-[4-[[1-[[3,5-bis(1,1-dimethylethyl)-4-hydroxyphenyl]thio]-1-methylethyl]thio]-2,6-bis(1,1-dimethylethyl)phenoxy]- | 30 | | 40% at 15 |
| Phenol, 4-[[1-[[3,5-bis(1,1-dimethylethyl)-4-ethoxyphenyl]thio]-1-methylethyl]thio]-2,6-bis(1,1-dimethylethyl)- | NE at 50 | | |
| 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, ethyl ester, (E)- | NE at 50 | | |
| Butanedioic acid, mono[4-[[1-[[3,5-bis(1,1-dimethylethyl)-4-methoxyphenyl]thio]1-methylethyl]thio]-2,6-bis(1,1-dimethylethyl)phenyl] ester | NE | | 89% at 15 |
| Phenol, 4-[[1-[[4-[2-[4-(dimethylamino)phenyl]ethoxy]-3,5-bis(1,1-dimethylethyl)phenyl]thio]-1-methylethyl]thio]-2,6-bis(1,1-dimethylethyl)- | 55 | | |
| Benzenamine, 4,4'-[(1-methylethylidene)bis[thio[2,6-bis(1,1-dimethylethyl)-4,1-phenylene]oxy-2,1-ethanediyl]]bis[N,N-dimethyl- | NE | | |
| L-Arginine, mono[4-[[1-[[3,5-bis(1,1-dimethylethyl)-4-hydroxyphenyl]thio]-1-methylethyl]thio]-2,6-bis(1,1-dimethylethyl)phenyl butanedioate] | 15 | 50 | 93% at 15 |
| pentanedioic acid, 4-[[1-[[3,5-bis(1,1-dimethylethyl)-4-hydroxyphenyl]thio]-1-methylethyl]thio]-,6-bis(1,1-dimethylethyl)phenyl methyl ester | 80 | | NE |
| 2-Propenoic acid, 3-[4-[[1-[[3,5-bis(1,1-dimethylethyl)-4-hydroxyphenyl]thio]-1-methylethyl]thio]-2,6-bis(1,1-dimethylethyl)phenoxy]-, (E)- | 30 | | NE |
| α-D-Galactopyranose, 6-O-[4-[[1-[[3,5-bis(1,1-dimethylethyl)-4-hydroxyphenyl]thio]-1-methylethyl]thio]-2,6-bis | 45 | | |

TABLE 1-continued

| Compound | VCAM-1 IC$_{50}$ or % inhibition at [μM] | LD$_{50}$ | ApoB/HepG2 IC$_{50}$ or % inhibition at [μM] |
|---|---|---|---|
| (1,1-dimethylethyl)phenyl]-1,2:3,4-bis-O-(1-methylethylidene) | | | |
| Phenol, 4-[[1-[[4-[3-(dimethylamino)propoxy]-3,5-bis(1,1-dimethylethyl)phenyl]thio]-1-methylethyl]thio]-2,6-bis(1,1-dimethylethyl)- | 22% at 50 | | |
| Glycine,N-[[4-[[1-[[3,5-bis(1,1-dimethylethyl)-4-hydroxyphenyl]thio]-1,methylethyl]thio]-2,6-bis(1,1-dimethylethyl)phenoxy]acetyl] | 15 | 50 | 83% at 15 |
| Glutamic acid, N-[[4-[[1-[[3,5-bis(1,1-dimethylethyl)-4-hydroxyphenyl]thio]-1-methylethyl]thio]-2,6-bis(1,1-dimethylethyl)phenoxy]acetyl] | 75 | 100 | 94% at 15 |
| L-Glutamic acid, N-[3-[4-[[1-[[3,5-bis(1,1-dimethylethyl)-4-hydroxyphenyl]thio]-1-methylethyl]thio]-2,6-bis(1,1-dimethylethyl)phenoxy]2-hydroxypropyl]-di-, diethyl ester | 10 | 50 | |
| Glycine, N-[4-[4[[1-[[3,5-bis(1,1-dimethylethyl)-4-hydroxphenyl]thio]-1-methylethyl]thio]-2,6-bis(1,1-dimethylethyl)phenoxy]2,3-dihydroxybutyl]- | 50 | >100 | |
| L-Lysine,N$^6$-[3-[4-[[1-[[3,5-bis(1,1-dimethylethyl)4-hydroxyphenyl]thio]-1-methylethyl]thio]-2,6-bis (1,1-dimethylethyl)phenoxy]-2-hydroxypropyl]- | 75 | 100 | |
| 2-Propenoic acid,4-[4-[[1-[[3,5-bis(1,1-dimethylethyl)-4-hydroxyphenyl]thio]-1-methylethyl]thio]-2,6-bis(1,1-dimethylethyl)phenoxy]butyl ester | 75 | | |
| Phenol, 4-[[1-[[3,5-bis(1,1-dimethylethyl)-4-(4-hydroxybutoxy)phenyl]thio]-1-methylethyl]thio]-2,6-bis(1,1-dimethylethyl)- | 125 | | |
| β-D-Glucopyranose, 6-O-[4-[1-[[3,5-bis(1,1-dimethylethyl)-4-hydroxyphenyl]thio]-1-methylethyl]thio]-2,6-bis(1,1-dimethylethyl)phenyl]- | 30% at 50 | | |
| 1-H-Tetrazole-1-butanoic acid, 4-[[1-[[3,5-bis(1,1-dimethylethyl)-4-hydroxyphenyl]thio]-1-methylethyl]thio]-2,6-bis(1,1-dimethylethyl)phenyl ester | 25% at 50 | | |
| Phenol, 4-[[1-[[3,5-bis(1,1-dimethylethyl)-4-[[3-hydroxy-1-propenyl)oxy]phenyl]thio]-1-methylethyl]thio]-1-methylethyl]thio]-2,6-bis(1,1-dimethylethyl)- | 55 | | |
| L-Lysine,N$^6$-[[4-[[1-[[3,5-bis(1,1-dimethylethyl)-4-hydroxyphenyl]thio]-1-methylethyl]thio]-2, | 30% at 50 | NE | |

TABLE 1-continued

| Compound | VCAM-1 IC$_{50}$ or % inhibition at [μM] | LD$_{50}$ | ApoB/HepG2 IC$_{50}$ or % inhibition at [μM] |
|---|---|---|---|
| 6-bis(1,1-dimethylethyl)phenoxy]acetyl]- | | | |
| D-Glucopyranose,6-O-[4-[[1-[[3,5-bis(1,1-dimethylethyl)-4-hydroxyphenyl]thio]-1-methylethyl]thio]-2,6-bis(1,1-dimethylethyl)phenyl]- | 10 | 50 | |
| D-Glucitol,6-O-[4-[[1-[[3,5-bis(1,1-dimethylethyl)-4-hydroxyphenyl]thio]-1-methylethyl]thio]-2,6-bis(1,1-dimethylethyl)phenyl]- | 15 | 50 | |
| Butanoic acid,4-[[hydroxy(2-hydroxyphenoxy)phosphinyl]oxy]-4-[[1-[[3,5-bis(1,1-dimethylethyl)-4-hydroxyphenyl]thio]-1-methylethyl]thio]-2,6-bis(1,1-dimethylethyl)phenyl ester | 43 | 75 | |
| Butanoic acid,4-hydroxy-3,3-dimethyl-,4-[[1-[[3,5-bis(1,1-dimethylethyl)-4-hydroxyphenyl]thio]-1-methylethyl]thio]-2,6-bis(1,1-dimethylethyl)phenyl ester | 110 | | 90% at 15 |
| Butanoic acid,4-(sulfoxy)-,1-[4-[[3,5-bis 1,1-dimethylethyl)-4-hydroxyphenyl]thio]-1-methylethyl]thio]-2,6-bis(1,1-dimethylethyl)phenyl]ester | 20 | 50 | NE |

Pharmaceutical Compositions

Mammals, and specifically humans, suffering from any of the above-described conditions can be treated by the topical, systemic or transdermal administration of a composition comprising an effective amount of the compound of formula (I) or formula (II) or a pharmaceutically acceptable salt thereof, optionally in a pharmaceutically acceptable carrier or diluent.

The composition is administered subcutaneously, intravenously, intraperitoneally, intramuscularly, parenterally, orally, submucosally, by inhalation, transdermally via a slow release patch, or topically, in an effective dosage range to treat the target condition. An effective dose can be readily determined by the use of conventional techniques and by observing results obtained under analogous circumstances. In determining the effective dose, a number of factors are considered including, but not limited to: the species of patient; its size, age, and general health; the specific disease involved; the degree of involvement or the severity of the disease; the response of the individual patient; the particular compound administered; the mode of administration; the bioavailability characteristics of the preparation administered; the dose regimen selected; and the use of concomitant medication. Typical systemic dosages for all of the herein described conditions are those ranging from 0.1 mg/kg to 500 mg/kg of body weight per day as a single daily dose or divided daily doses. Preferred dosages for the described conditions range from 5–1500 mg per day. A more particularly preferred dosage for the desired conditions ranges from 25–750 mg per day. Typical dosages for topical application are those ranging from 0.001 to 100% by weight of the active compound.

The compound is administered for a sufficient time period to alleviate the undesired symptoms and the clinical signs associated with the condition being treated.

The active compound is included in the pharmaceutically acceptable carrier or diluent in an amount sufficient to deliver to a patient a therapeutic amount of compound in vivo in the absence of serious toxic effects.

The concentration of active compound in the drug composition will depend on absorption, inactivation, and excretion rates of the drug as well as other factors known to those of skill in the art. It is to be noted that dosage values will also vary with the severity of the condition to be alleviated. It is to be further understood that for any particular subject, specific dosage regimens should be adjusted over time according to the individual need and the professional judgment of the person administering or supervising the administration of the compositions, and that the dosage ranges set forth herein are exemplary only and are not intended to limit the scope or practice of the claimed composition. The active ingredient may be administered at once, or may be divided into a number of smaller doses to be administered at varying intervals of time.

A preferred mode of administration of the active compound for systemic delivery is oral. Oral compositions will generally include an inert diluent or an edible carrier. They may be enclosed in gelatin capsules or compressed into tablets. For the purpose of oral therapeutic administration, the active compound can be incorporated with excipients and used in the form of tablets, troches, or capsules. Pharmaceutically compatible binding agents, and/or adjuvant materials can be included as part of the composition.

The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

When the dosage unit form is a capsule, it can contain, in addition to material of the above type, a liquid carrier such as a fatty oil. In addition, dosage unit forms can contain various other materials which modify the physical form of the dosage unit, for example, coatings of sugar, shellac, or other enteric agents.

The compound or its salts can be administered as a component of an elixir, suspension, syrup, wafer, chewing gum or the like. A syrup may contain, in addition to the active compounds, sucrose as a sweetening agent and certain preservatives, dyes and colorings and flavors.

The compound can also be mixed with other active materials which do not impair the desired action, or with materials that supplement the desired action. The active compounds can be administered in conjunction with other medications used in the treatment of cardiovascular disease, including lipid lowering agents such as probucol and nicotinic acid; platelet aggregation inhibitors such as aspirin; antithrombotic agents such as coumadin; calcium channel blockers such as varapamil, diltiazem, and nifedipine; angiotensin converting enzyme (ACE) inhibitors such as captopril and enalopril, and β-blockers such as propanalol, terbutalol, and labetalol. The compounds can also be administered in combination with nonsteroidal antiinflammatories such as ibuprofen, indomethacin, fenoprofen, mefenamic acid, flufenamic acid, sulindac. The compound can also be administered with corticosteriods.

Solutions or suspensions used for parenteral, intradermal, subcutaneous, or topical application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic.

If administered intravenously, preferred carriers are physiological saline, bacteriostatic water, Cremophor EL™ (BASF, Parsippany, N.J.) or phosphate buffered saline (PBS).

In a preferred embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) are also preferred as pharmaceutically acceptable carriers. These may be prepared according to methods known to those skilled in the art, for example, as described in U.S. Pat. No. 4,522,811 (which is incorporated herein by reference in its entirety). For example, liposome formulations may be prepared by dissolving appropriate lipid(s) (such as stearoyl phosphatidyl ethanolamine, stearoyl phosphatidyl choline, arachadoyl phosphatidyl choline, and cholesterol) in an inorganic solvent that is then evaporated, leaving behind a thin film of dried lipid on the surface of the container. An aqueous solution of the compound is then introduced into the container. The container is then swirled by hand to free lipid material from the sides of the container and to disperse lipid aggregates, thereby forming the liposomal suspension.

Suitable vehicles or carriers for topical application can be prepared by conventional techniques, such as lotions, suspensions, ointments, creams, gels, tinctures, sprays, powders, pastes, slow-release transdermal patches, suppositories for application to rectal, vaginal, nasal or oral mucosa. In addition to the other materials listed above for systemic administration, thickening 0agents, emollients, and stabilizers can be used to prepare topical compositions. Examples of thickening agents include petrolatum, beeswax, xanthan gum, or polyethylene, humectants such as sorbitol, emollients such as mineral oil, lanolin and its derivatives, or squalene.

Modifications and variations of the present invention relating to compounds that inhibit the suppression of VCAM-1 and methods of treating diseases mediated by the expression of VCAM-1 will be obvious to those skilled in the art from the foregoing detailed description of the invention. Such modifications and variations are intended to come with the scope of the appended claims.

What is claimed is:

1. A compound of the formula

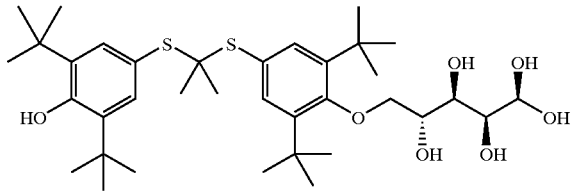

or a pharmaceutically acceptable salt or ester thereof.

2. A compound of the formula

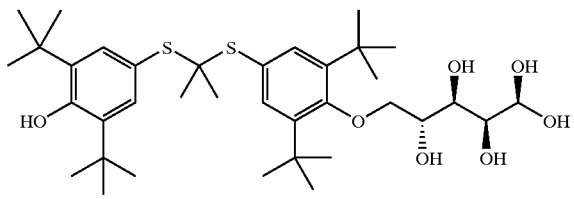

or a pharmaceutically acceptable salt thereof.

3. A pharmaceutical composition comprising a compound of the formula

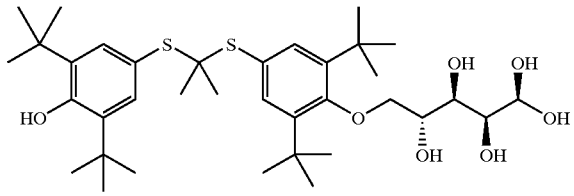

together with a pharmaceutically acceptable carrier.

4. The pharmaceutical composition of claim 3, wherein the pharmaceutically acceptable carrier is suitable for oral administration.

5. The pharmaceutical composition of claim 3, wherein the pharmaceutically acceptable carrier is suitable for topical administration.

6. The pharmaceutical composition of claim 3, wherein the pharmaceutically acceptable carrier is suitable for intravenous administration.

7. The pharmaceutical composition of claim 3, wherein the pharmaceutically acceptable carrier is suitable for subcutaneous administration.

8. The pharmaceutical composition of claim 3, wherein the pharmaceutically acceptable carrier is suitable for intraperitoneal administration.

9. The pharmaceutical composition of claim 3, wherein the pharmaceutically acceptable carrier is suitable for intramuscular administration.

10. The pharmaceutical composition of claim 3, wherein the pharmaceutically acceptable carrier is suitable for submucosal administration.

11. The pharmaceutical composition of claim 3, wherein the pharmaceutically acceptable carrier is suitable for inhalation administration.

12. The pharmaceutical composition of claim 3, wherein the pharmaceutically acceptable carrier is suitable for transdermal administration.

13. A method for the treatment of an inflammatory disorder, comprising administering to a host in need thereof an effective treatment amount of a compound of the formula

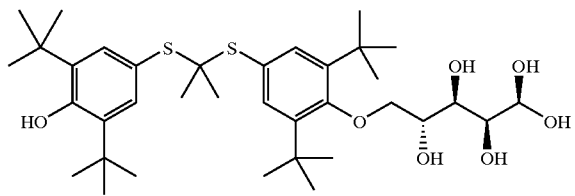

or a pharmaceutically acceptable salt thereof.

14. The method of claim 13, wherein the inflammatory disorder is arthritis.

15. The method of claim 13, wherein the inflammatory disorder is rheumatoid arthritis.

16. The method of claim 13, wherein the inflammatory disorder is osteoarthritis.

17. The method of claim 13, wherein the inflammatory disorder is asthma.

18. The method of claim 13, wherein the inflammatory disorder is dermatitis.

19. The method of claim 13, wherein the inflammatory disorder is multiple sclerosis.

20. The method of claim 13, wherein the inflammatory disorder is psoriasis.

21. A method for the treatment of a disorder mediated by VCAM-1, comprising administering to a host in need thereof an effective treatment amount of a compound of the formula

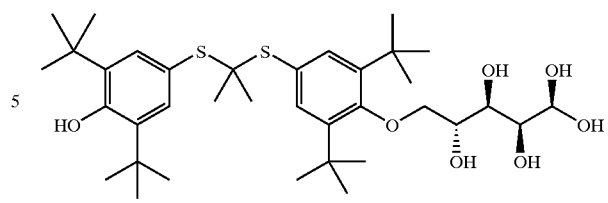

or a pharmaceutically acceptable salt thereof.

22. A method for the treatment of a cardiovascular disorder, comprising administering to a host in need thereof an effective treatment amount of a compound of the formula

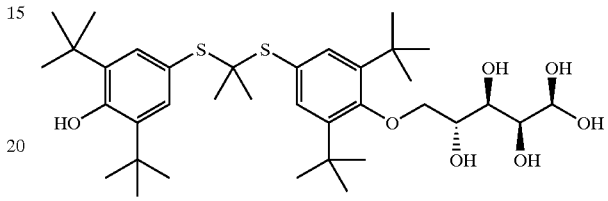

or a pharmaceutically acceptable salt thereof.

23. The method of claim 22, wherein the cardiovascular disorder is selected from the group consisting of atherosclerosis, post-angioplasty restenosis, coronary artery disease, angina and small artery disease.

24. A method for suppressing the expression of a redox-sensitive gene or activating a gene that is suppressed through a redox-sensitive pathway, comprising administering to a host in need thereof an effective treatment amount of a compound of the formula

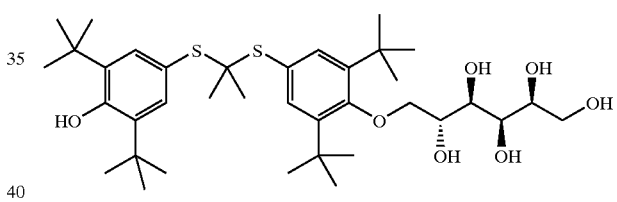

or a pharmaceutically acceptable salt thereof.

25. The method of claim 24, wherein the redox-sensitive gene expresses cytokines.

26. A method of treating an immune response, comprising administering to a host in need thereof an effective treatment amount of a compound of the formula

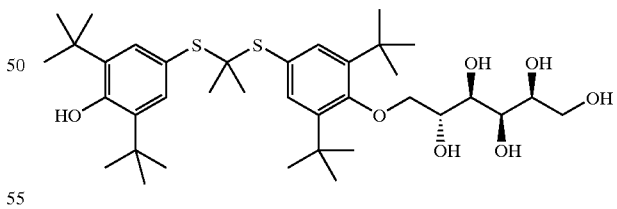

or a pharmaceutically acceptable salt thereof.

* * * * *